United States Patent
Cui et al.

(10) Patent No.: US 11,998,609 B2
(45) Date of Patent: Jun. 4, 2024

(54) SELF-ASSEMBLING ANTIVIRAL PRODRUGS

(71) Applicant: The Johns Hopkins University, Baltimore, MD (US)

(72) Inventors: Honggang Cui, Baltimore, MD (US); Charles Williams Flexner, Baltimore, MD (US); Maya Monroe, Baltimore, MD (US); Han Wang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/981,595

(22) Filed: Nov. 7, 2022

(65) Prior Publication Data
US 2023/0147365 A1    May 11, 2023

Related U.S. Application Data

(60) Provisional application No. 63/277,144, filed on Nov. 8, 2021.

(51) Int. Cl.
*A61K 47/64* (2017.01)
*A61P 31/18* (2006.01)
*A61P 31/20* (2006.01)

(52) U.S. Cl.
CPC .............. *A61K 47/64* (2017.08); *A61P 31/18* (2018.01); *A61P 31/20* (2018.01)

(58) Field of Classification Search
CPC ........... A61K 47/64; A61P 31/18; A61P 31/20
See application file for complete search history.

(56) References Cited

U.S. PATENT DOCUMENTS

2005/0059578 A1* 3/2005 Thorpe .............. A61K 47/6811
514/19.3

OTHER PUBLICATIONS

Cheetham et al., Linker-determined drug release mechanism of free camptothecin from self-assembling drug amphiphiles. Chem Commun (Camb). Jun. 7, 2014;50(45):6039-42.
Department of Health and Human Services: Panel on Antiretroviral Guidelines for Adults and Adolescents, Guidelines for the Use of Antiretroviral Agents in Adults and Adolescents with HIV, 2019. 454 pages.
Giesler et al., Next-Generation Reduction Sensitive Lipid Conjugates of Tenofovir: Antiviral Activity and Mechanism of Release. J Med Chem. Nov. 23, 2016;59(22):10244-10252.
Kull et al., Mixtures of Quaternary Ammonium Compounds and Long-chain Fatty Acids as Antifungal Agents. Appl Microbiol. Nov. 1961; 9(6): 538-541.
Ladner et al., Inducible expression of human hepatitis B virus (HBV) in stably transfected hepatoblastoma cells: a novel system for screening potential inhibitors of HBV replication. Antimicrob Agents Chemother. Aug. 1997;41(8):1715-20.
Pradere et al., Synthesis of Nucleoside Phosphate and Phosphonate Prodrugs. Chem. Rev. 2014, 114, 18, 9154-9218.
Remington: The Science and Practice of Pharmacy Lippincott, Williams and Wilkins. 2005 TOC only. 13 pages.
Terrault et al., Update on prevention, diagnosis, and treatment of chronic hepatitis B: AASLD 2018 hepatitis B guidance. Hepatology. Apr. 2018;67(4):1560-1599.

* cited by examiner

*Primary Examiner* — Li N Komatsu
(74) *Attorney, Agent, or Firm* — Casimir Jones, S.C.; Thomas A. Isenbarger

(57) ABSTRACT

Disclosed are therapeutic self-assembling molecules including a peptide sequence conjugated to one or more antiviral therapeutics to form a peptide-based antiviral prodrug capable of self-assembly into supramolecular structures with varying morphology in aqueous solutions, which can be injected subcutaneously or intramuscularly for the long-acting treatment of chronic viral infections.

8 Claims, 20 Drawing Sheets

SELF-ASSEMBLING ANTIVIRAL PRODRUGS

This application claims the benefit of U.S. provisional patent application Ser. No. 63/277,144, filed Nov. 8, 2021, which is incorporated herein by reference in its entirety.

FEDERALLY SPONSORED RESEARCH OR DEVELOPMENT

This invention was made with government support under grant DMR-1255081 and DGE-1746891 awarded by the National Science Foundation. The government has certain rights in the invention.

BACKGROUND

A significant challenge in the advancement of antiviral therapies for chronic viral infections is the achievement of long-acting release to prolong dosing intervals. There is substantial patient interest in long-acting treatment strategies, including long acting injectable (LAI) formulations, for the treatment of chronic viral infections.

SUMMARY

In some aspects, the presently disclosed subject matter provides a composition comprising a peptide sequence conjugated to one or more antiviral (e.g., antiretroviral therapeutics (ARVs)) to form a peptide-based antiviral prodrug. In certain aspects, the one or more antiviral therapeutics is selected from a non-nucleoside reverse transcriptase inhibitor (NNRTI), an integrase strand transfer inhibitor (INSTI), and a nucleoside reverse transcriptase inhibitor (NRTI). In particular aspects, the one or more antiviral therapeutics is selected from lamivudine, tenofovir, nevirapine, efavirenz, rilpivirine, raltegravir, dolutegravir, emtricitabine, abacavir, cabotegravir, and GS-6207.

In yet more particular aspects, the peptide-based ARV prodrug is selected from:

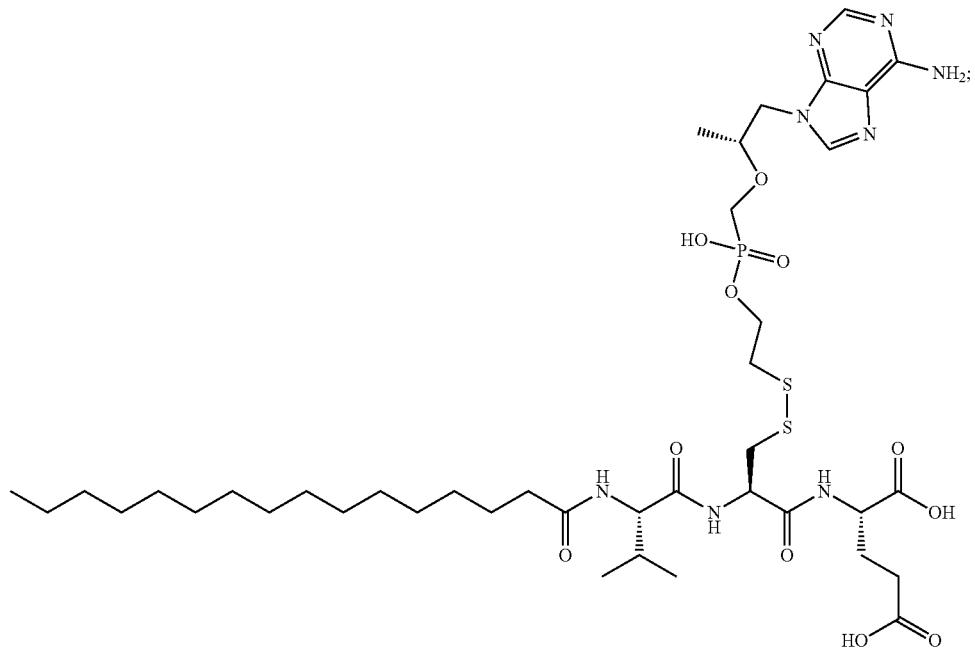

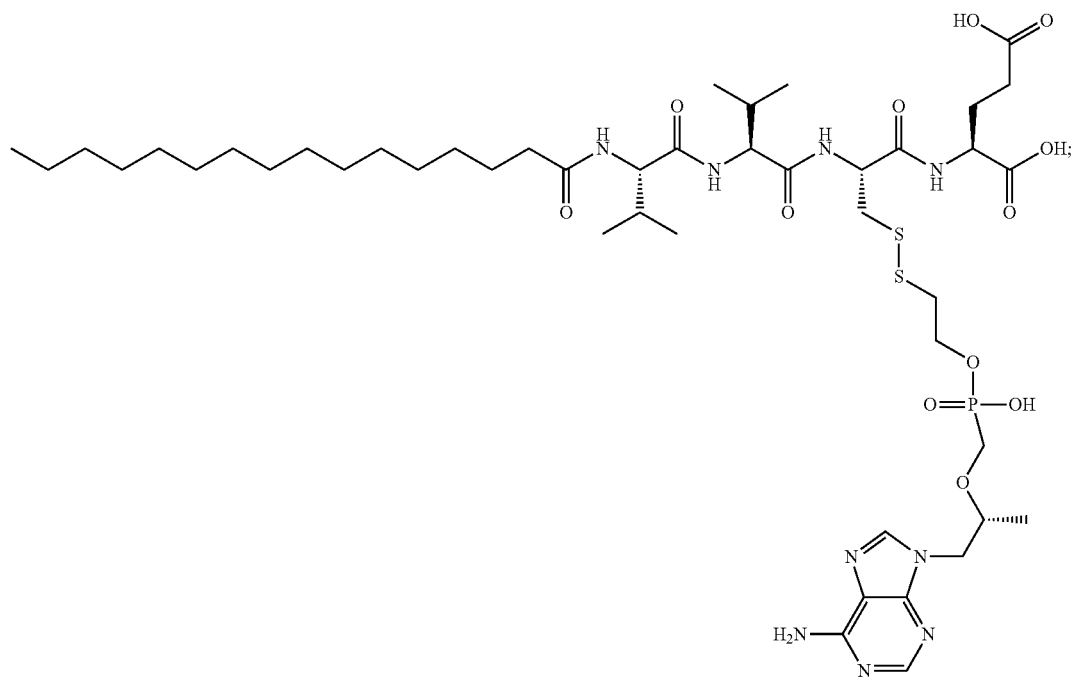
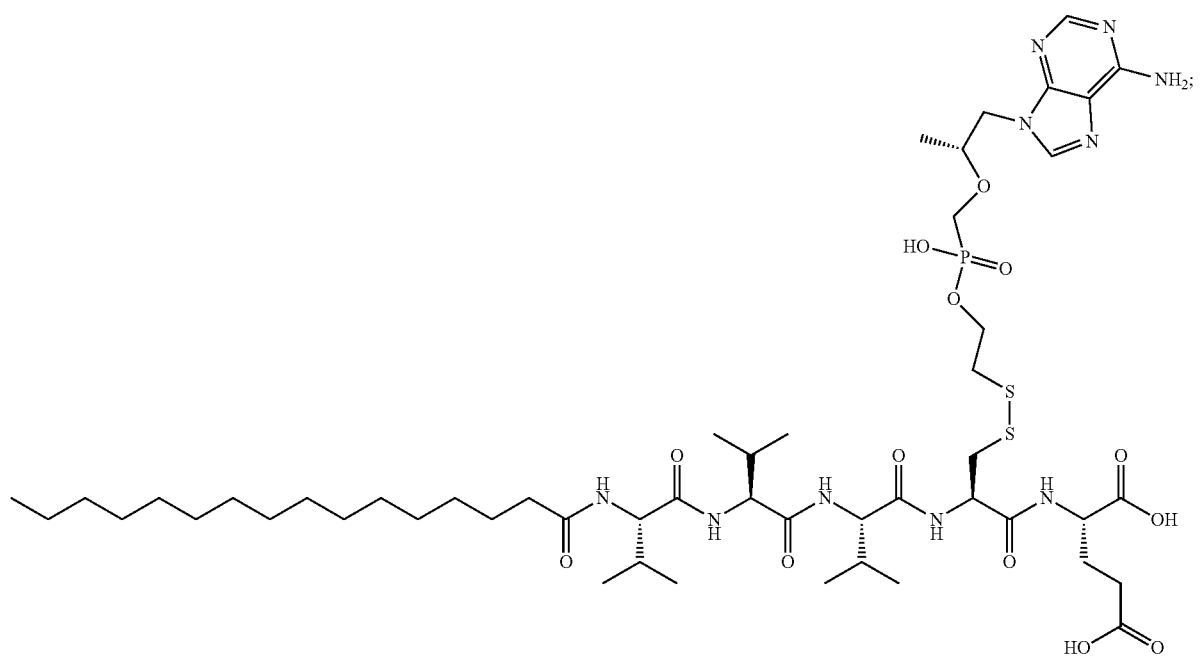

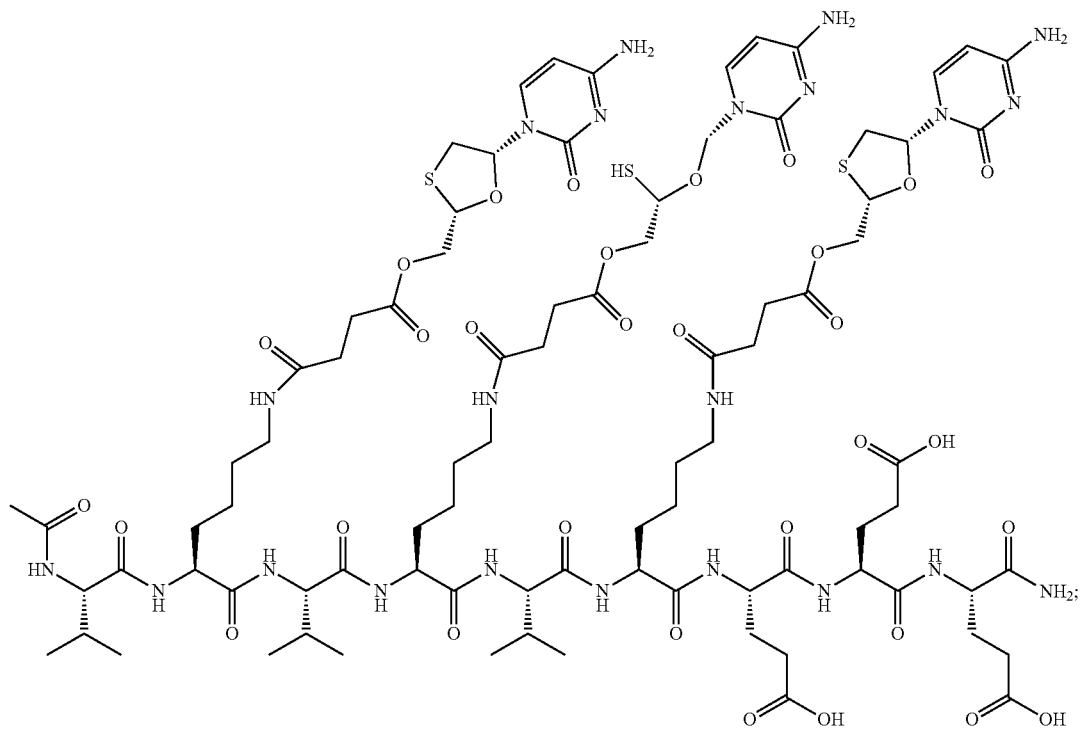
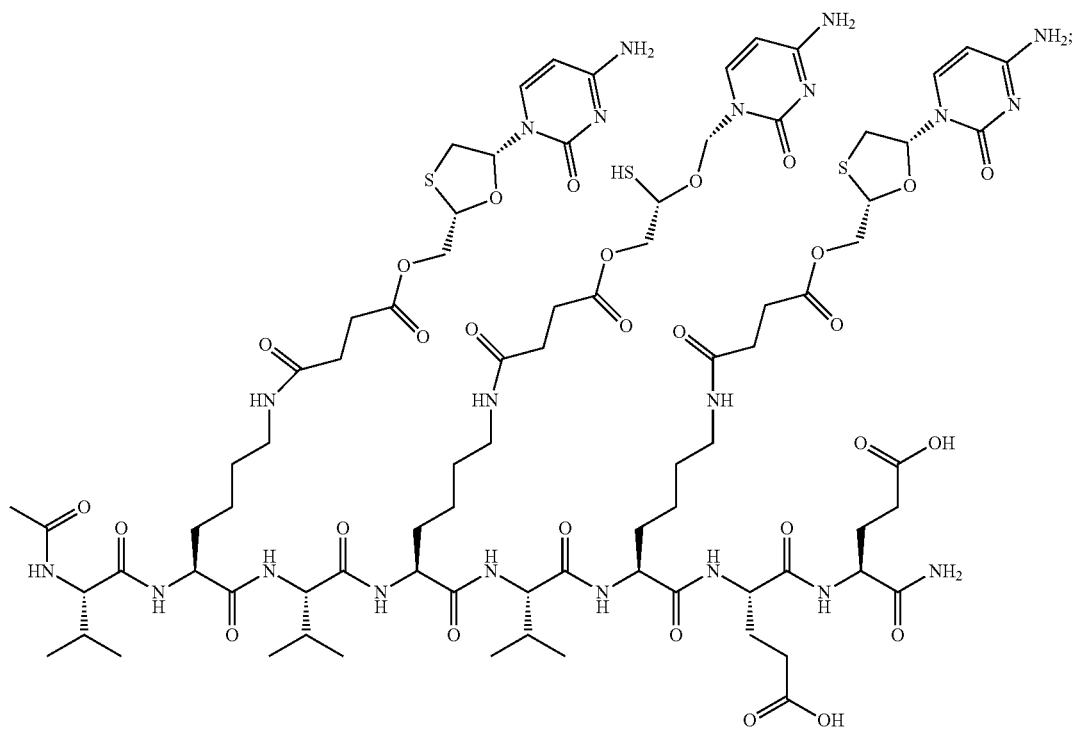

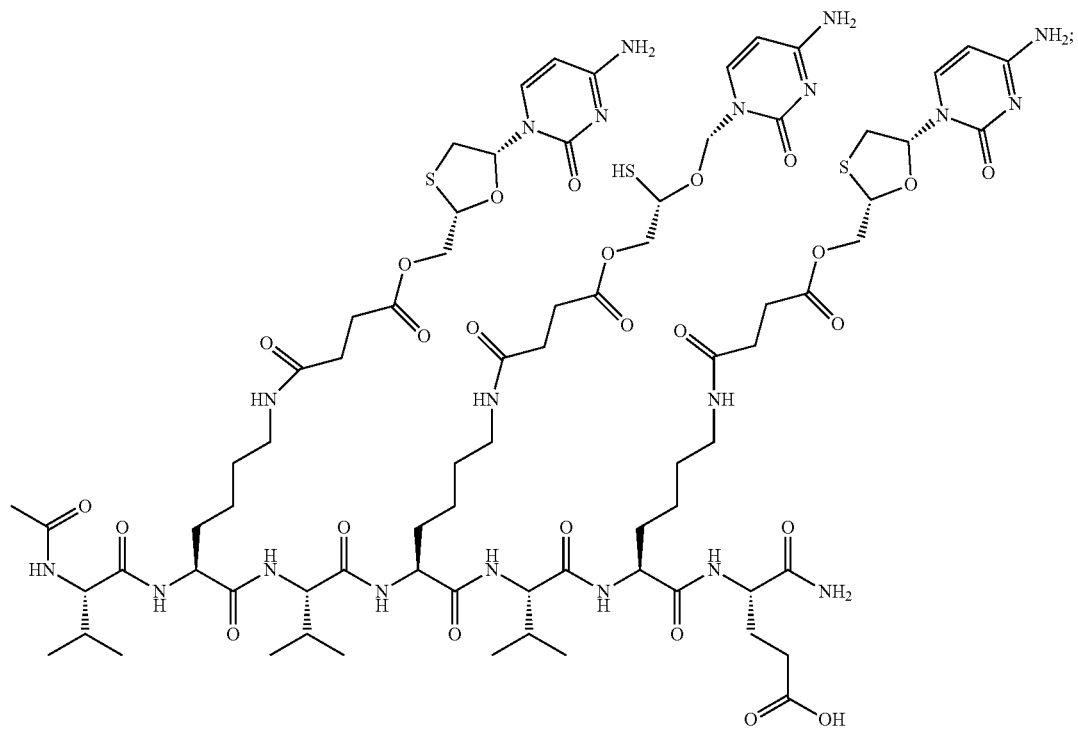
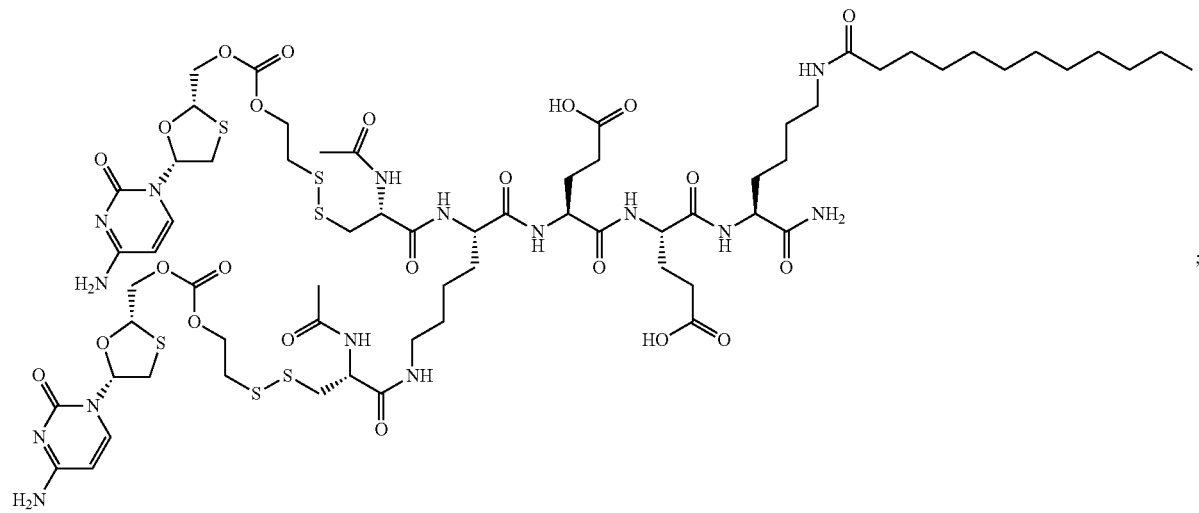
d3TC-E$_2$-C$_{12}$

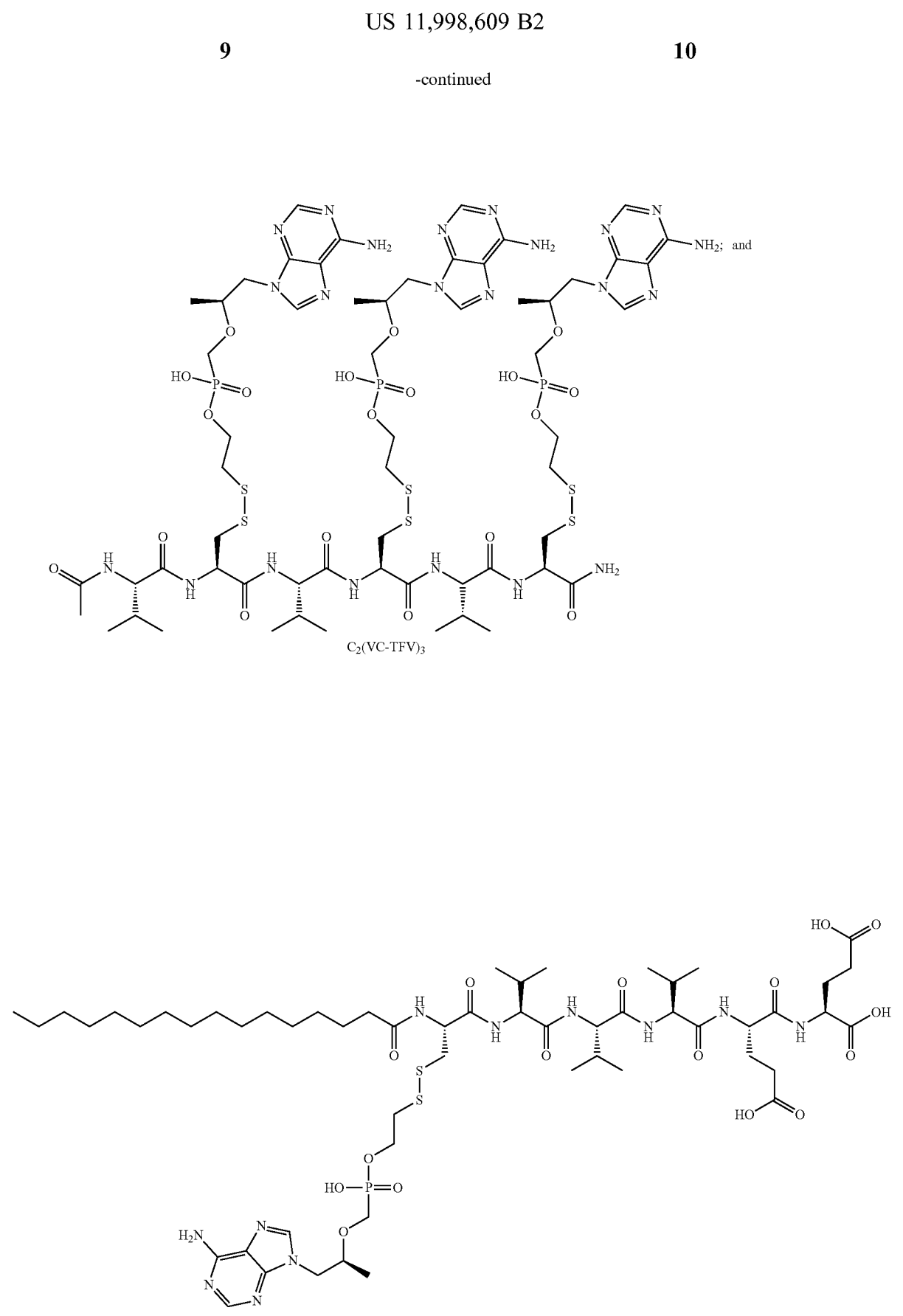

-continued

C₂(VC-TFV)₃

In certain aspects, the peptide-based antiviral prodrug comprises a compound designated by A(VC-TFV)₃B having the following chemical structure:

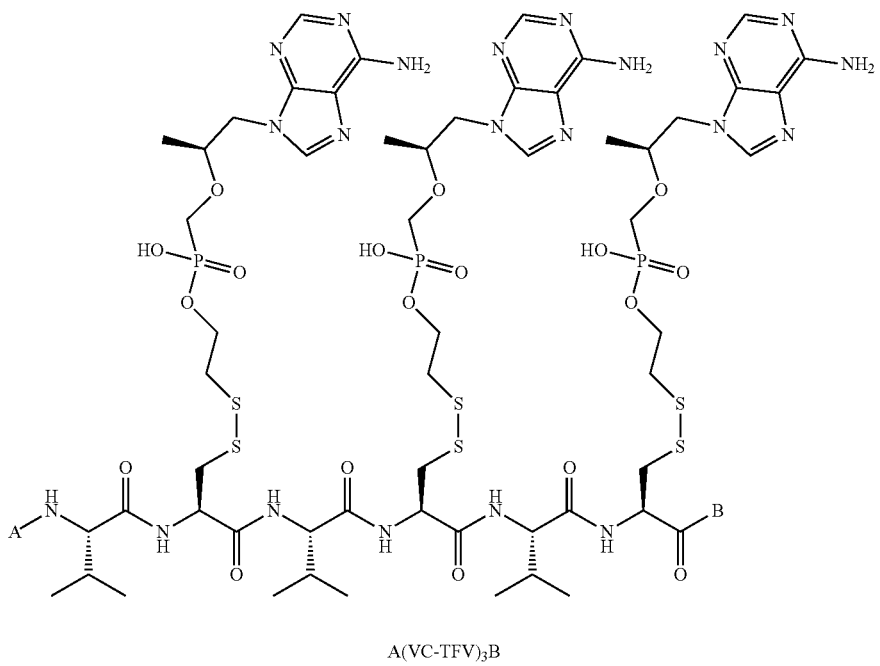

A(VC-TFV)₃B wherein: A is a terminal amino acid or a $C_1$-$C_{20}$ alkylene group; and B is an amino group or an amino acid-$NH_2$ group.

In particular aspects, A is an alkylene group selected from $C_2$, $C_6$, $C_8$, and $C_{12}$. In particular aspects, A is an amino acid. In more particular aspects, the amino acid is selected from Trp, Val, Leu, and Gly. In certain aspects, B is an amino group. In more certain aspects, B is selected from TrpNH₂, ValNH₂, and LeuNH₂, and GlyNH₂.

In some aspects, the peptide-based antiviral prodrug comprises a compound having a structure according to:

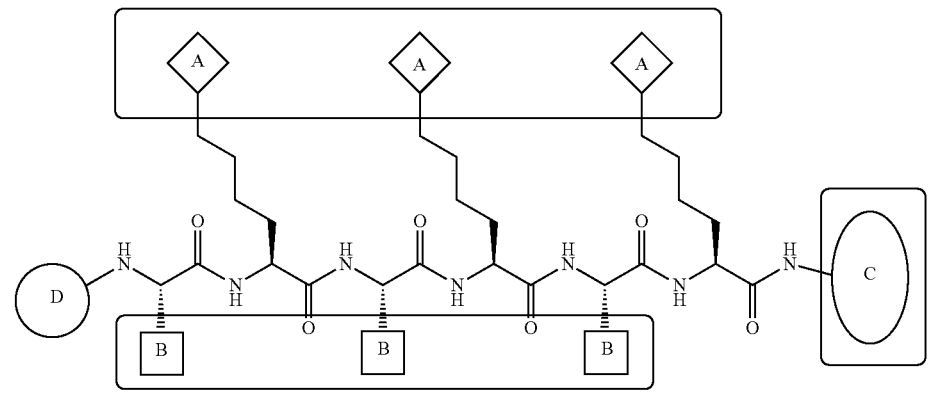

where A is an antiviral drug (e.g., lamivudine); B is an alkyl group (e.g., isopropyl); D is acetyl; and C comprises a number of (e.g., 1, 2, or 3) amino acids (e.g., glutamic acid).

In some aspects, the peptide-based antiviral prodrug comprises a compound having a structure according to:

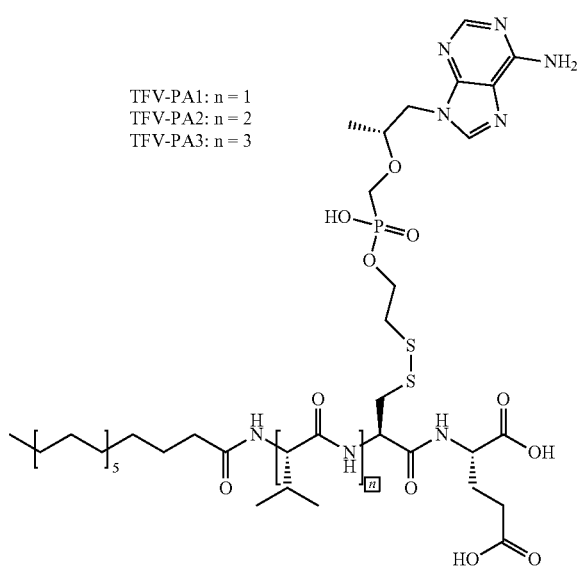

TFV-PA1: n = 1
TFV-PA2: n = 2
TFV-PA3: n = 3 where n is 1, 2, or 3.

In other aspects, the composition comprises two or more antiviral therapeutics and a targeting moiety.

In certain aspects, the composition further comprises a hydrophobic moiety encapsulated within a hydrophobic core of the composition comprising the peptide sequence conjugated to one or more antiviral therapeutics.

In other aspects, the presently disclosed subject matter provides a method for treating or preventing a viral infection, the method comprising administering to a subject in need of treatment thereof a therapeutic amount of any of the presently disclosed compositions.

In other aspects, the presently disclosed subject matter provides a method for treating or preventing a retroviral infection, the method comprising administering to a subject in need of treatment thereof a therapeutic amount of the presently disclosed composition.

In other aspects, the presently disclosed subject matter provides a method for treating or preventing a chronic retroviral infection, the method comprising administering to a subject in need of treatment thereof a therapeutic amount of the presently disclosed composition.

In particular aspects, the viral infection is infection by hepatitis B virus. In particular aspects, the viral infection is infection by human immunodeficiency virus.

In other aspects, the presently disclosed subject matter provides a method for treating or preventing a human immunodeficiency virus (HIV) infection, the method comprising administering to a subject in need of treatment thereof a therapeutic amount of the presently disclosed composition.

In certain aspects, the subject has or is suspected of having acquired immunodeficiency syndrome (AIDS). In more certain aspects, the subject is a mother who has or is suspected of having an HIV infection or AIDS. In yet more certain aspects, the subject is an infant of a mother who has or is suspected of having an HIV infection or AIDS.

In other aspects, the presently disclosed subject matter provides a method for treating or preventing a hepatitis B virus infection, the method comprising administering to a subject in need of treatment thereof a therapeutic amount of the presently disclosed composition.

In certain aspects, the subject has or is suspected of having hepatitis B.

In other aspects, the presently disclosed subject matter provides a method for treating or preventing a hepatitis virus infection, the method comprising administering to a subject in need of treatment thereof a therapeutic amount of the presently disclosed composition.

In certain aspects, the administering is by subcutaneous or intramuscular injection.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1A:
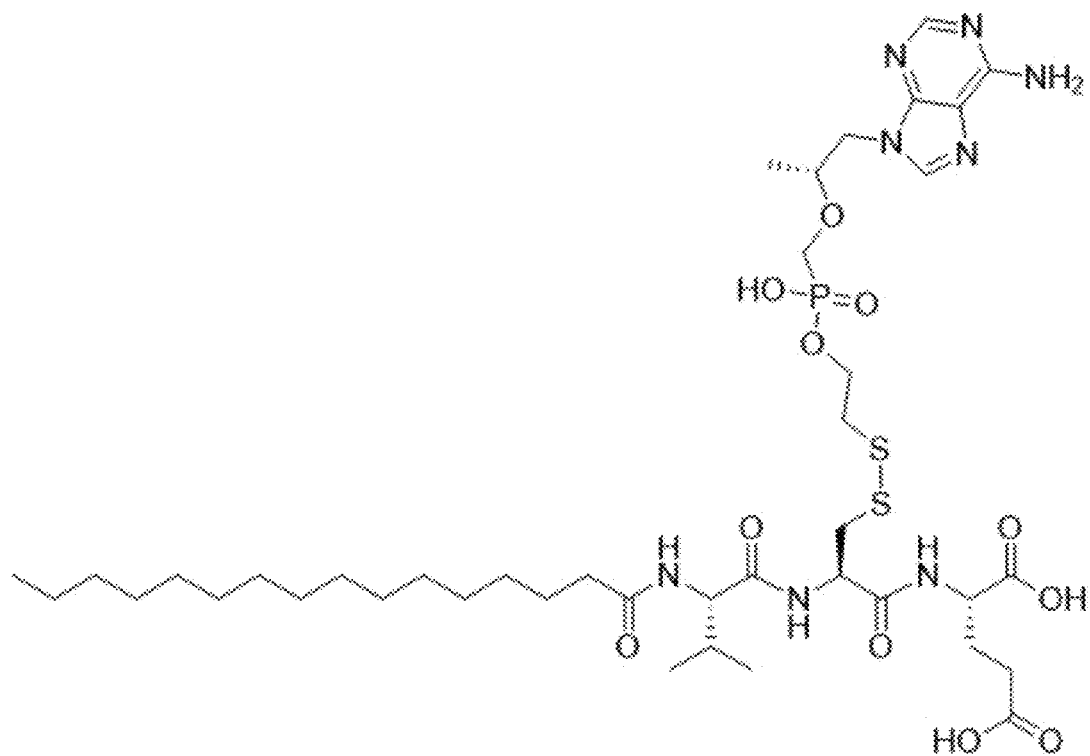
FIG. 1A shows a structure of an exemplary drug amphiphile TFV-PA1.

Having thus described the presently disclosed subject matter in general terms, reference will now be made to the accompanying Figures, which are not necessarily drawn to scale, and wherein:

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides therapeutic self-assembling molecules that are capable of self-formulation into supramolecular structures with varying morphology in aqueous solutions to be injected subcutaneously or intramuscularly for the long-acting treatment of viral (e.g., retroviral) infections, e.g., hepatitis B, HIV/human immunodeficiency virus/AIDS (acquired immunodeficiency syndrome), etc.

In some embodiments, the presently disclosed self-assembling molecules include a peptide sequence conjugated to one or more antiviral therapeutics (e.g., antiretroviral therapeutics) to form a peptide-based antiviral (e.g., antiretroviral) prodrug referred to herein as an "ARV drug amphiphile" (ARV DA). Without wishing to be bound to any one particular theory, the supramolecular self-assembly is driven by various non-covalent interactions, including hydrophobic interactions, pi-pi stacking, hydrogen bonding, and beta sheet formation. Both hydrophilic and hydrophobic drugs can be directly conjugated to the peptide sequence. Hydrophobic moieties also can be encapsulated within the hydrophobic core of the supramolecular structures. The peptide sequence can be altered to change the self-assembly behavior of the ARV DA or to target the ARV DA to specific immune cells using immune-receptor specific peptide sequences.

The supramolecular structures formed are soluble in aqueous environments. In the presence of ions at the concentrations found under physiological conditions, however, one-dimensional nanostructures entangle into hydrogels. Because the hydrogel formation is nearly instantaneous, it is possible to inject a solution of ARV DAs intramuscularly or subcutaneously to form a hydrogel drug depot without damaging the hydrogel structure.

The presently disclosed system allows for facile tuning of release and cellular accumulation because the pharmacokinetic distribution of the active drug is controlled by disassembly of the structures, the chemistry of the linker molecule used to conjugate the ARVs to the peptide, and the peptide sequence of the DA. The non-covalent nature of the interactions within the presently disclosed hydrogel system means that a dynamic equilibrium exists in the system between the hydrogel, assembled filamentous nanostructures, and disassembled ARV DAs. Changes in the critical assembly concentration (CAC) dictate disassembly of the structures and can be controlled by alterations to sequence design.

The local delivery of the supramolecular structures in a hydrogel depot can attain systemic circulation through the following mechanism: free ARV DAs diffuse out of the depot into the surrounding tissue, the filamentous nanostructures disassemble to maintain the free ARV DA concentration in the hydrogel, resulting in sustained, linear release. The free ARV DAs enter the lymphatic capillaries of nearby draining lymph nodes. The free ARV DAs then enter circulation from the lymph nodes and attain systemic distribution.

Circulating ARV DAs can be taken up by immune cells (it is possible to target the ARV DA to specific immune cells using immune-receptor specific peptide sequences). Once taken up by the cells, the linker molecule directly conjugating the ARVs to the peptide sequence is reduced in the presence of high intracellular concentrations of glutathione, releasing the free drug within the cell. Hydrophilic free ARVs are trapped within the cell because of their inability to pass through the cellular membrane.

Because the same ARVs are used for treatment and prevention of viral infections (e.g., HIV), the presently disclosed ARV prodrugs have the potential to be used in both therapeutic and preventative medicine. The overall goal of the supramolecular therapeutics is to improve targeted delivery to infected cells, reduce drug toxicity, and increase dosing intervals, thereby improving treatment outcomes and enhancing patient adherence.

Goals of the presently disclosed systems include an increase in patient compliance, a reduced necessary dose, an increased half-life of encapsulated ARV, an increased accumulation in viral reservoirs, and a decrease in off-site accumulation and drug toxicity. Such systems can be used both for systemic and local delivery but have experienced limited clinical success due to a failure to improve efficacy and cost efficiency.

Despite the potential for the application of self-assembling drug amphiphiles to ARV delivery, there has been no success at developing a long-acting formulation of an NRTI. Several ARVs exist as prodrug, including tenofovir (TFV): tenofovir disoproxil fumarate and tenofovir alafenamide; amprenavir (APV): fosamprenavir; and emtricitabine (FTC): multiple prodrugs have exhibited preclinical success. Representative structures of ARVs and their prodrugs are provided immediately herein below. Such compounds can be delivered locally for systemic release.

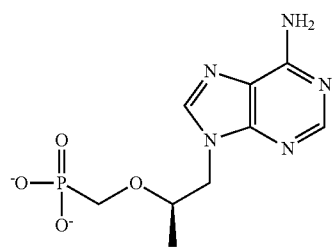

Tenofovir

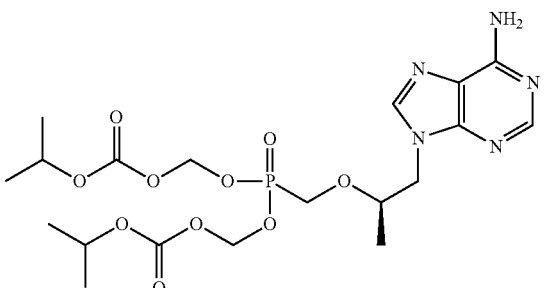

Tenofovir Disoproxil Fumarate

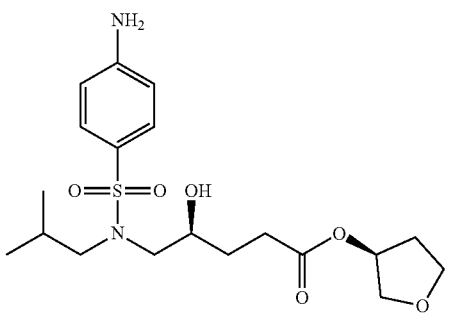

Amprenavir

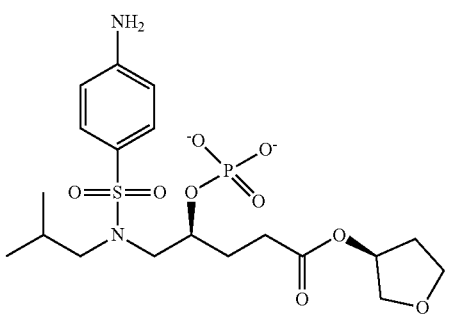

Fosamprenavir

Accordingly, in some embodiments, the presently disclosed subject matter provides a composition comprising a peptide sequence conjugated to one or more antiviral therapeutics (ARVs) to form a peptide-based ARV prodrug. In certain embodiments, the one or more antiviral therapeutics is selected from a non-nucleoside reverse transcriptase inhibitor (NNRTI), an integrase strand transfer inhibitor (INSTI), and a nucleoside reverse transcriptase inhibitor (NRTI). In particular embodiments, the one or more antiviral therapeutics is selected from lamivudine, tenofovir, nevirapine, efavirenz, rilpivirine, raltegravir, dolutegravir, emtricitabine, abacavir, cabotegravir, and GS-6207.

In yet more particular embodiments, the peptide-based ARV prodrug is selected from:

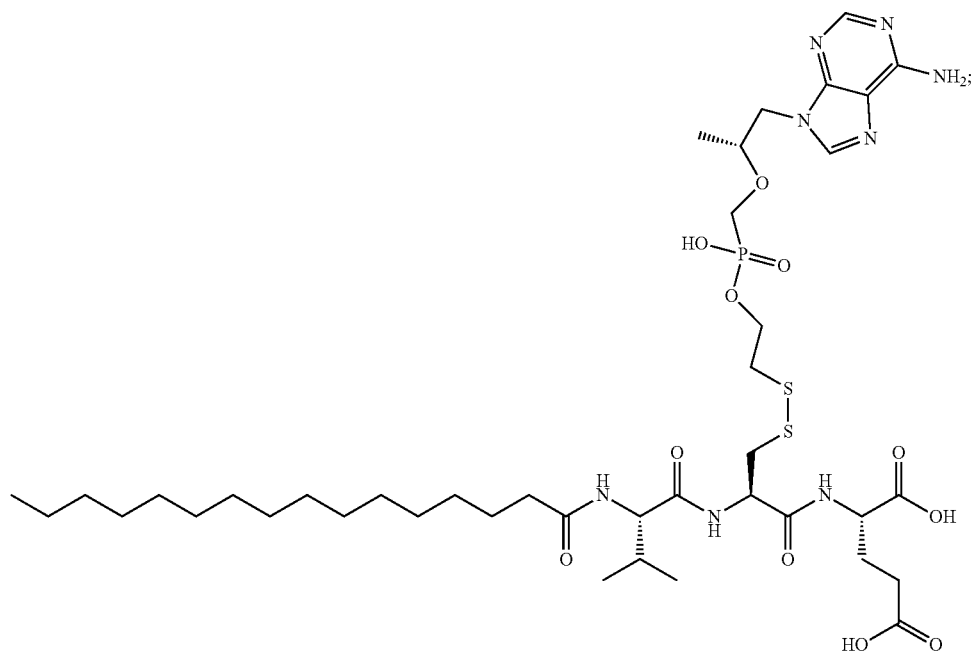
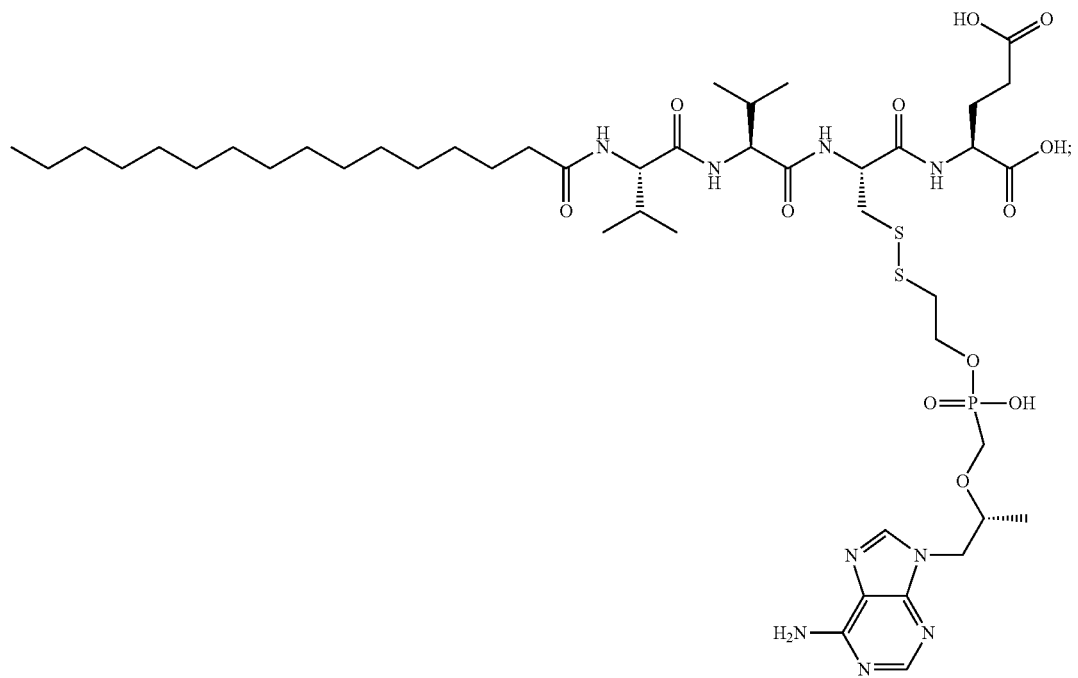

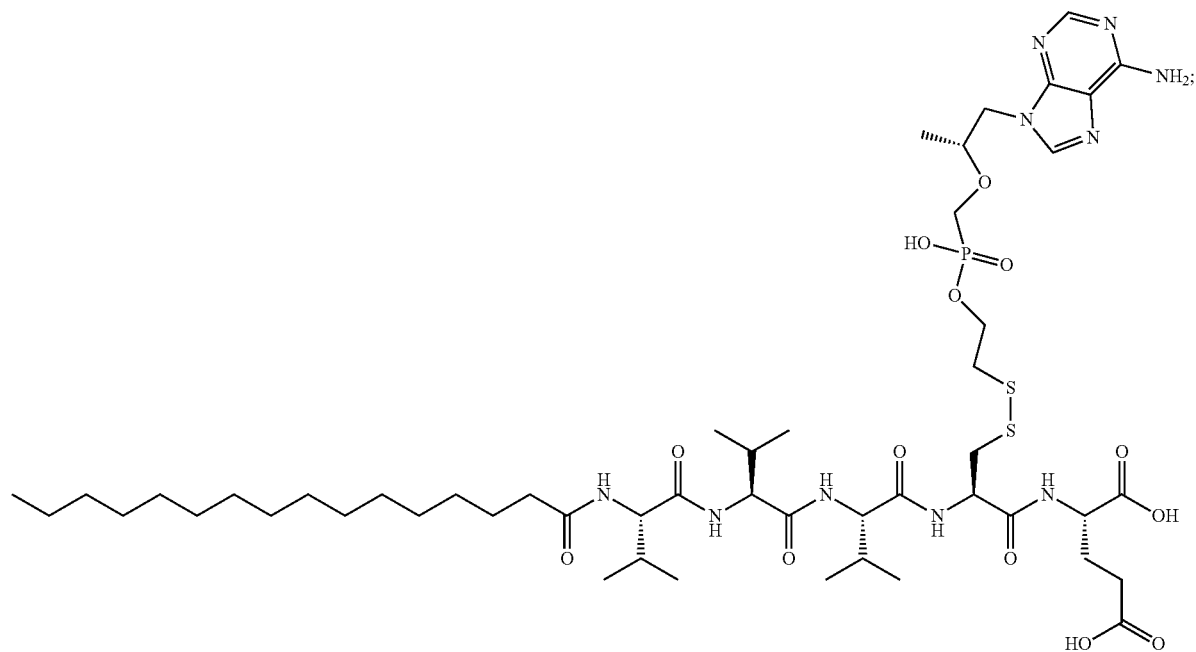
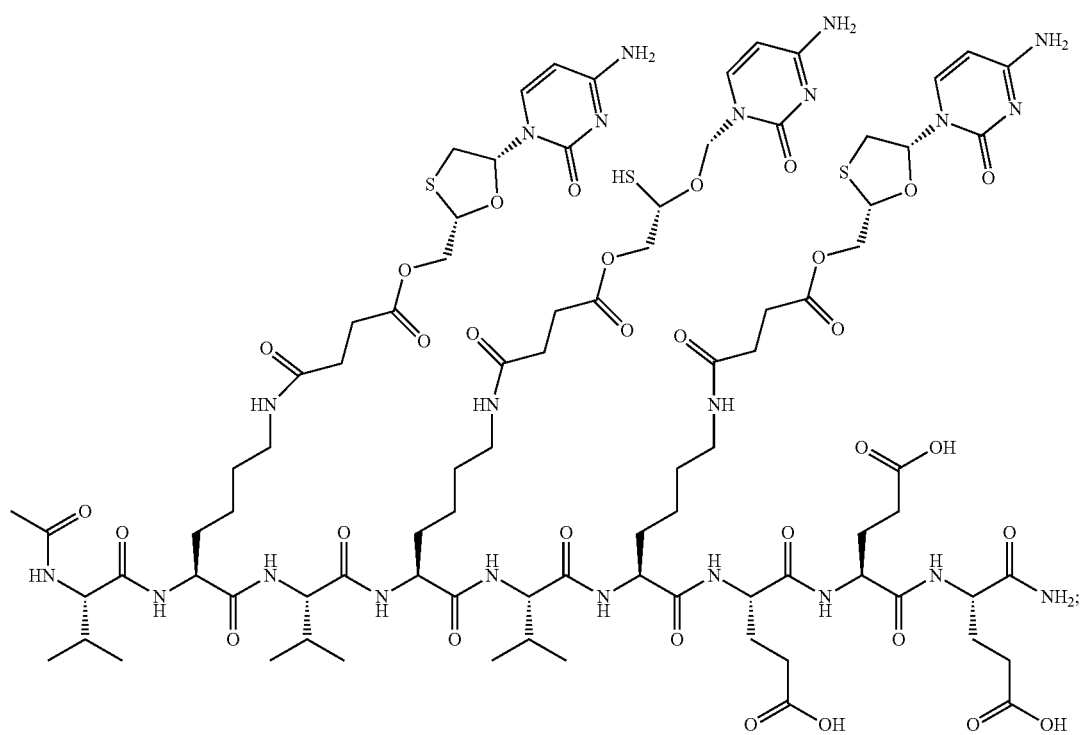

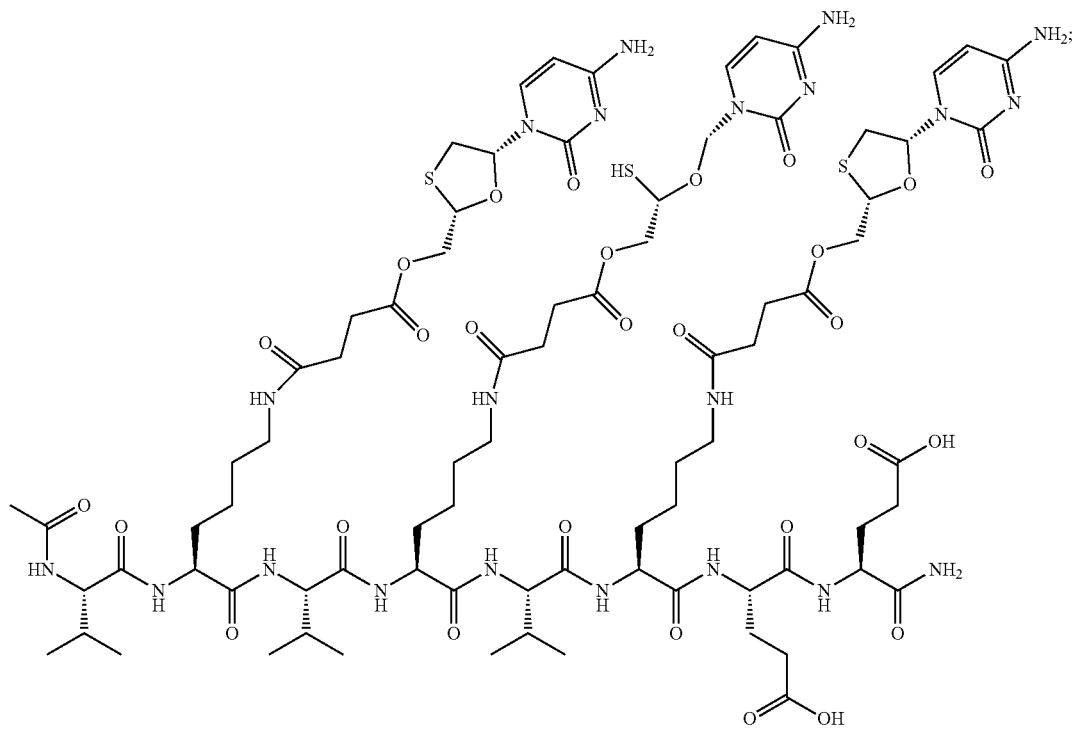
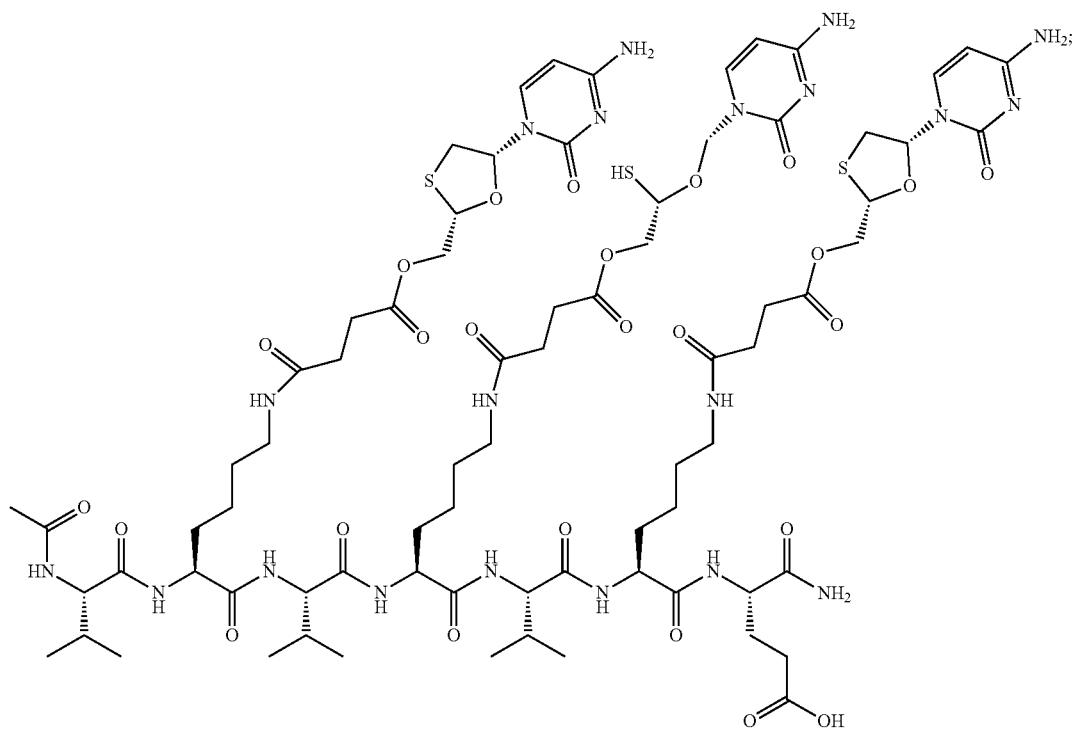

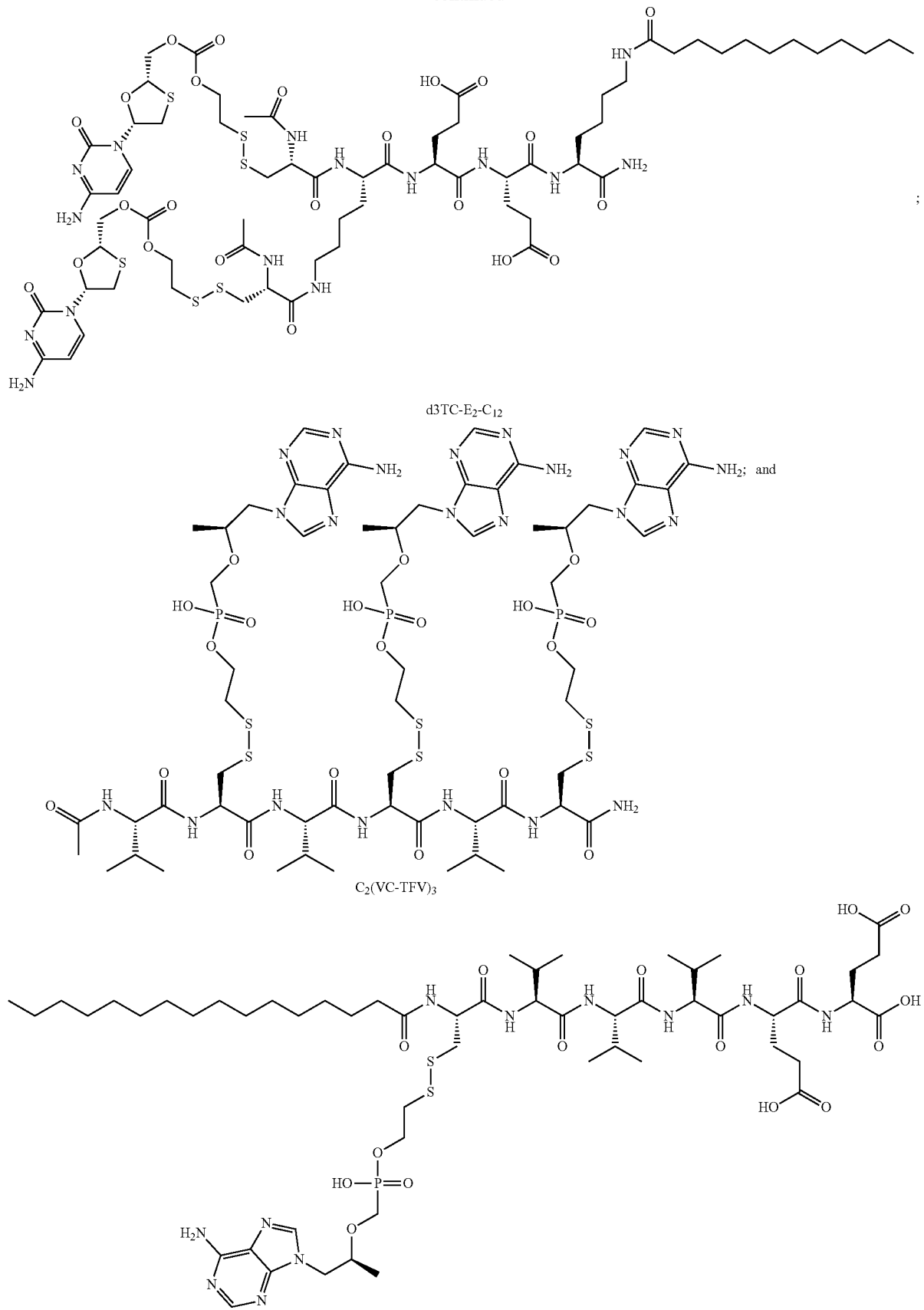

In certain embodiments, the peptide-based ARV prodrug comprises a compound designated by A(VC-TFV)$_3$B having the following chemical structure:

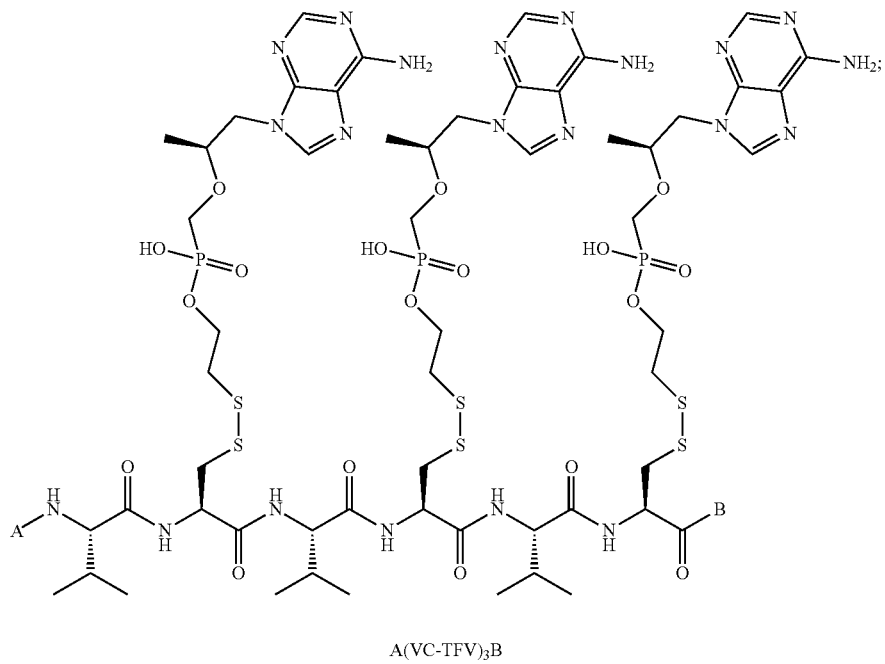

A(VC-TFV)$_3$B wherein: A is a terminal amino acid or a $C_1$-$C_{20}$ alkylene group, including $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, and $C_{20}$; and B is an amino group or an amino acid-NH$_2$ group.

In some embodiments, the peptide-based antiviral prodrug comprises a compound having a structure according to:

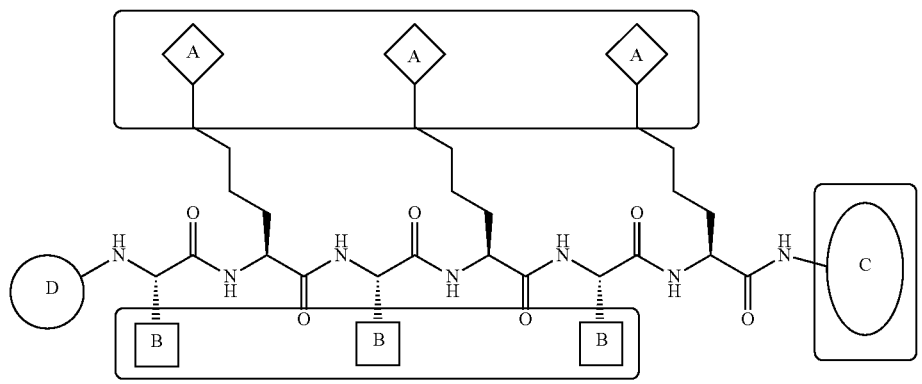

where A is an antiviral drug (e.g., lamivudine); B is an alkyl group (e.g., isopropyl); D is acetyl; and C comprises a number of (e.g., 1, 2, or 3) amino acids (e.g., glutamic acid).

In some embodiments, the peptide-based antiviral prodrug comprises a compound having a structure according to:

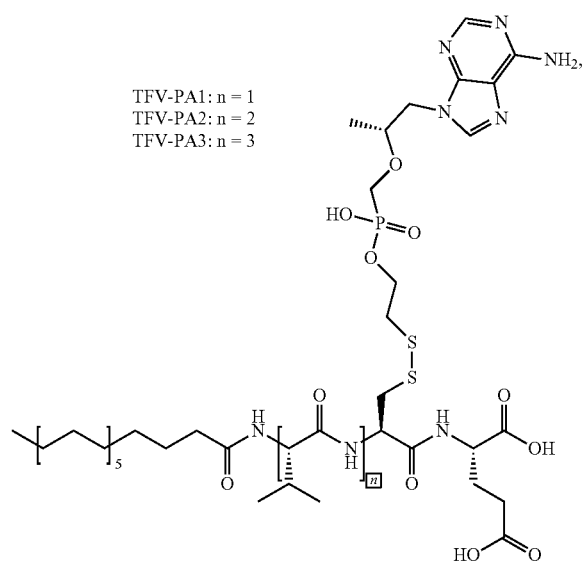

TFV-PA1: n = 1
TFV-PA2: n = 2
TFV-PA3: n = 3 where n is 1, 2, or 3.

During experiments conducted during the development of technologies described herein, an NRTI hydrogel delivery platform was produced by conjugating TFV to amphiphilic peptide sequences to provide antiviral prodrug hydrogelators. See Example 1. The technology provides an excipient-free, injectable delivery system for tenofovir. The peptide amphiphile system is capable of supramolecular assembly with an intact phosphonate group. Data collected during experiments indicated that modifying the number of valines in the peptide sequence impacted supramolecular assembly and gelation of the designs, which in turn affects release. Hydrogels formed from TFV-PA3 displayed near-linear release in vitro for more than a month, with more than 80% of prodrugs remaining at day 30. Furthermore, prodrug conversion did not negatively impact the antiviral activity of the TFV-PAs and free TFV is released under reducing conditions. Accordingly, the technology described herein provides an LAI TFV formulation. In particular, TFV-PA3 provides a molecule for further optimization for in vivo exploration and eventual clinical development, e.g., because it forms a hydrogel drug depot in situ capable of sustained release.

Further, during experiments conducted during the development of technologies described herein, self-assembling prodrugs were produced. See Example 2. In particular, supramolecular hydrogels were produced and data were collected indicating that the supramolecular hydrogels provide a long-acting formulation for hydrophilic antiretroviral drugs. The drug conjugates formed by the alternating hydrophilic-hydrophobic peptide provide multiple functional sites and a high drug loading rate, with terminal glutamic acids to tune their self-assembling and gelation properties. Triggered upon subcutaneous injection, this in situ formed hydrogel exhibited vastly improved stability and significantly extended the release profile of hydrophilic ARV agents. In vivo data revealed V-3TC-E3 hydrogel depot gradually degraded after administration.

As used herein, the term "amino acid" includes moieties having a carboxylic acid group and an amino group. The term amino acid thus includes both natural amino acids (including proteinogenic amino acids) and non-natural amino acids. The term "natural amino acid" also includes other amino acids that can be incorporated into proteins during translation (including pyrrolysine and selenocysteine). Additionally, the term "natural amino acid" also includes other amino acids, which are formed during intermediary metabolism, e.g., ornithine generated from arginine in the urea cycle.

The natural amino acids are alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), Methionine (Met), asparagine (Asn), proline (Pro), glutamine (Gln), arginine (Arg), serine (Ser), threonine (Thr), valine (Val), tryptophan (Trp), and tyrosine (Tyr).

In particular embodiments, A is an alkylene group selected from $C_2$, $C_6$, $C_8$, and $C_{12}$. In particular embodiments, A is an amino acid. In more particular embodiments, the amino acid is selected from Trp, Val, Leu, and Gly. In certain embodiments, B is an amino group. In more certain embodiments, B is selected from $TrpNH_2$, $ValNH_2$, and $LeuNH_2$, and $GlyNH_2$.

In other embodiments, the composition comprises two or more antiviral (e.g., antiretroviral) therapeutics and a targeting moiety.

In certain embodiments, the composition further comprises a hydrophobic moiety encapsulated within a hydrophobic core of the composition comprising the peptide sequence conjugated to one or more antiviral (e.g., antiretroviral) therapeutics.

In other aspects, the presently disclosed subject matter provides a method for treating or preventing a viral infection, the method comprising administering to a subject in need of treatment thereof a therapeutic amount of the presently disclosed composition.

In other aspects, the presently disclosed subject matter provides a method for treating or preventing a retroviral infection, the method comprising administering to a subject in need of treatment thereof a therapeutic amount of the presently disclosed composition.

In other aspects, the presently disclosed subject matter provides a method for treating or preventing a human immunodeficiency virus (HIV) infection, the method comprising administering to a subject in need of treatment thereof a therapeutic amount of the presently disclosed composition.

In certain aspects, the subject has or is suspected of having acquired immunodeficiency syndrome (AIDS). In more certain aspects, the subject is a mother who has or is suspected of having an HIV infection or AIDS. In yet more certain aspects, the subject is an infant of a mother who has or is suspected of having an HIV infection or AIDS.

In other aspects, the presently disclosed subject matter provides a method for treating or preventing a hepatitis virus (e.g., HBV) infection, the method comprising administering to a subject in need of treatment thereof a therapeutic amount of the presently disclosed composition.

In certain aspects, the administering is by subcutaneous or intramuscular injection.

The terms "subject" and "patient" are used interchangeably herein. The subject treated by the presently disclosed methods, uses, self-assembling antiviral (e.g., antiretroviral) prodrugs and compositions comprising those self-assembling antiviral (e.g., antiretroviral) prodrugs in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease, e.g., a viral infection (e.g., a retroviral infection). In some embodiments, the viral infection is an HIV infection. In some embodiments, the subject has AIDS. In some embodiments, the viral infection is a hepatitis virus infection (e.g., HBV)

The terms "decrease," "reduced," "reduction," "decrease," or "inhibit" are all used herein generally to mean a decrease by a statistically significant amount. However, for avoidance of doubt, "reduced," "reduction," "decrease," or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, where the decrease is less than 100%. In one embodiment, the decrease includes a 100% decrease (e.g., absent level as compared to a reference sample), or any decrease between 10-100% as compared to a reference level.

The terms "increased," "increase," "enhance," or "activate" are all used herein to generally mean an increase by a statically significant amount; for the avoidance of any doubt, the terms "increased," "increase," "enhance," or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

In general, the presently disclosed methods result in a decrease in the severity of a condition, disease, or disorder (e.g., a viral (e.g., retroviral) infection such as, e.g., HIV infection or AIDS; or a viral infection that causes hepatitis) in a subject. The term "decrease" is meant to inhibit, suppress, attenuate, diminish, arrest, or stabilize a symptom of the condition, disease, or disorder. As used herein, the terms "treat," "treating," "treatment," and the like refer to reducing or ameliorating a disease or condition, and/or symptoms associated therewith. It will be appreciated that, although not precluded, treating a disease or condition does not require that the disorder, condition or symptoms associated therewith be completely eliminated.

The term "preventing" refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

In general, the "effective amount", "amount effective to treat" or "therapeutically effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

It should be appreciated that the amount of at least one self-assembling antiviral prodrug effective to treat a viral infection comprises the maximal non-toxic dose that is sufficient for improving the health of a subject. It should be appreciated that the amount of at least one self-assembling antiretroviral prodrug effective to treat a retroviral infection comprises the maximal non-toxic dose that is sufficient for improving the health of a subject. It should be appreciated that the amount of at least one self-assembling antiretroviral prodrug effective to treat HIV/AIDS comprises the maximal non-toxic dose that sufficient for improving HIV/AIDS in a subject. It should be appreciated that the amount of at least one self-assembling antiviral prodrug effective to treat hepatitis B infection comprises the maximal non-toxic dose that is sufficient for improving hepatitis B in a subject.

The term "combination" is used in its broadest sense and means that a subject is administered at least two agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Further, the presently disclosed compositions can be administered alone or in combination with adjuvants that enhance stability of the agents, facilitate administration of pharmaceutical compositions containing them in certain embodiments, provide increased dissolution or dispersion, increase activity, provide adjuvant therapy, and the like, including other active ingredients. Advantageously, such combination therapies utilize lower dosages of the conventional therapeutics, thus avoiding possible toxicity and adverse side effects incurred when those agents are used as monotherapies.

The timing of administration of at least one self-assembling antiviral (e.g., antiretroviral) prodrug can be varied so long as the beneficial effects of the combination of these agents are achieved. Accordingly, the phrase "in combination with" refers to the administration of at least one self-assembling antiviral (e.g., antiretroviral) prodrug, and optionally additional agents either simultaneously, sequentially, or a combination thereof. Therefore, a subject administered a combination of at least one self-assembling antiviral (e.g., antiretroviral) prodrug, and optionally additional agents can receive at least one self-assembling antiviral (e.g., antiretroviral) prodrug, and optionally additional agents at the same time (i.e., simultaneously) or at different times (i.e., sequentially, in either order, on the same day or on different days), so long as the effect of the combination of all agents is achieved in the subject.

When administered sequentially, the agents can be administered within 1, 5, 10, 30, 60, 120, 180, 240 minutes or longer of one another. In other embodiments, agents administered sequentially, can be administered within 1, 2, 3, 4, 5, 10, 15, 20 or more days of one another. Where the agents are administered simultaneously, they can be administered to the subject as separate pharmaceutical compositions, each comprising at least one self-assembling antiretroviral prodrug, and optionally additional agents, or they can be administered to a subject as a single pharmaceutical composition comprising all agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of an agent and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index}(SI)$$

wherein:
Q$_A$ is the concentration of a component A, acting alone, which produced an end point in relation to component A;
Q$_a$ is the concentration of component A, in a mixture, which produced an end point;
QB is the concentration of a component B, acting alone, which produced an end point in relation to component B; and
Q$_b$ is the concentration of component B, in a mixture, which produced an end point.

Generally, when the sum of Q$_a$/Q$_A$ and Q$_b$/Q$_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

In another embodiments, the presently disclosed subject matter provides a pharmaceutical composition including at least one self-assembling antiviral (e.g., antiretroviral) prodrug, and optionally additional agents, alone or in combination with one or more additional therapeutic agents in admixture with a pharmaceutically acceptable excipient.

More particularly, the presently disclosed subject matter provides a pharmaceutical composition comprising at least one self-assembling antiviral (e.g., antiretroviral) prodrug, and optionally additional agents, and a pharmaceutically acceptable carrier. In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams and Wilkins (2000).

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, 100% in some embodiments ±50%, in some embodiments ±20%, in some embodiments ±10%, in some embodiments ±5%, in some embodiments ±1%, in some embodiments ±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration and are not to be construed as limiting in any manner to make compounds of the disclosure by other methods.

Example 1—Tenofovir Peptide Amphiphiles

During the development of embodiments of the technology provided herein, experiments were conducted to conjugate tenofovir (TFV) to peptide amphiphiles to provide an antiviral prodrug.

A significant challenge in the advancement of chronic antiviral therapeutics is the achievement of long-acting release to prolong dosing intervals. There is substantial patient interest in long-acting treatment strategies, including long acting injectable (LAI) formulations, for the treatment of chronic infections resulting from hepatitis B virus (HBV) and human immunodeficiency virus (HIV). Such therapeutic formulations would improve meeting the diverse needs of the patient population, thereby improving quality of life and treatment adherence.

Tenofovir (TFV) is a an antiviral treatment for both chronic HBV and HIV, successfully controlling viral replication and consequently slowing progression to severe disease. See, e.g., Terrault, Hepatology, 2018, 67, 1560-1599; and Department of Health and Human Services: Panel on Antiretroviral Guidelines for Adults and Adolescents, Guidelines for the Use of Antiretroviral Agents in Adults and Adolescents with HIV, 2019, each of which is incorporated herein by reference. Despite this medical need, there are no FDA approved long-acting formulations of TFV or any other HBV therapeutic because most antiviral LAI delivery strategies employ formulation of therapeutics into nanosuspensions. In particular, tenofovir is a highly hydrophilic (log P=−2.5) nucleotide reverse transcriptase inhibitor (NRTI) that is consequently difficult to provide in a nanosuspension formulation. As a result, previous LAI TFV technologies have attempted to mask the hydrophilicity of the parent drug to improve conversion of the drug into nanocrystals or semi-solid nanoparticles for a nanosuspension. However, the need for potentially irritating excipient materials in such nanosuspensions has led to frequent injection site reactions in both experimental and FDA-approved antiretroviral LAIs. While these reactions are less severe than the tissue necrosis associated with TFV implants, they are still significant enough to dissuade patient interest. Consequently, a novel formulation strategy is necessary that can form a drug depot in situ without the need for any excipient materials.

Self-assembling peptides form supramolecular polymeric hydrogels under physiological conditions with great biocompatibility and tunable biodegradability, thus providing a class of LAI biomaterials. Through encapsulation or covalent conjugation of therapeutics, these systems provide a drug depot upon injection for long-acting release. Peptide amphiphile-based systems are of particular interest for drug delivery due to their robust and consistent self-assembly into filamentous structures, well understood sequence surface display, and robust synthesis protocols. Furthermore, previous work has demonstrated that the morphology, stability, gelation, and release of these self-assembling platforms can be controlled through changes to the peptide sequence, number or type of hydrophobic moiety, linker chemistry, hydrogen bonding propensity, and surface charge. As changes to these supramolecular properties can impact drug delivery outcomes, drug-containing peptide amphiphile systems are especially well suited for adoption as highly tunable, long-acting injectable drug delivery platforms. Beyond being naturally biocompatible, biodegradable, and biomimetic, LAI systems have a fixed drug loading content if covalent conjugation is employed, can be applied to a variety of ARVs with differing physicochemical properties, and sequester prodrugs within the nanostructures, thereby attaining extremely high concentrations of therapeutic within the hydrogel depot while avoiding the toxicity issues observed in TFV implants. In this context, by conjugating TFV to an amphiphilic peptide sequence, the technology described herein provides a series of self-assembling prodrug hydrogelators that maximize prodrug loading (e.g., provide 100% prodrug loading), fast (e.g., instantaneous or nearly instantaneous) gelation, and sustained release without the need for excipient materials and that exhibit tunable properties for optimization of TFV delivery and release.

Fmoc amino acids and resins for peptide synthesis were obtained from Advanced Automated Peptide Protein Technologies (AAPPTEC, Louisville, KY). Tenofovir was purchased from Combi-Blocks (San Diego, CA). All other solvents and reagents were sourced from VWR (Radnor, PA), Thermo Fisher Scientific (Pittsburgh, PA), or MilliporeSigma (St. Louis, MO). HepAD38 cells were provided by Prof. Chloe Thio's lab of the Johns Hopkins University School of Medicine (Infectious Diseases Department, Baltimore, MD). Reverse phase high performance liquid chromatography (RP-HPLC) was performed using a Varian ProStar Model 325 HPLC (Agilent Technologies, Santa Clara, CA) equipped with a fraction collector. Preparative separations used a Varian PLRP-S column (100 Å, 10 µm, 150×25 mm) at a flow rate of 20 mL/min, with 10 mL injection volumes. Analytical HPLC used an Agilent Zorbax Extend-C18 RP column (5 µm, 150×4.6 mm) at a flow rate of 1 mL/min, with 25 µL injection volumes. Select analytical HPLC experiments (as denoted in protocol subsequent protocols) were carried out using a 1260 Infinity II LC system (Agilent Technologies, Santa Clara, CA) and the Agilent Zorbax Extend-C18 RP column (5 µm, 150×4.6 mm) at a flow rate of 1 mL/min, with 25 µL injection volumes. Acidic (0.1% v/v trifluoroacetic acid) and basic (0.1% v/v ammonium hydroxide) water and acetonitrile were used as the mobile phase. 220 nm and 260 nm wavelengths were monitored for all molecules during RP-HPLC. Molecules were lyophilized using a FreeZone −50° C. 4.5L freeze dryer (Labconco, Kansas City, MO). Mass spectrometry data was obtained using either a BrukerAutoflex III Smartbeam (Bruker, Billerica, MA) instrument for matrix-assisted laser desorption/ionization time of flight (MALDI-TOF) MS using sinapic acid as the matrix, or a Finnigan LCQ ion trap mass spectrometer (Thermo-Finnigan, Waltham, MA) for electron spray ionization (ESI) MS. Bruker Avance 300 or 400 MHz FT-NMR spectrometers were used to acquire 1H and 13C NMR spectra. Circular dichroism measurements were performed using a Jasco J-710 spectropolarimeter (JASCO, Easton, MD). Electron microscopy was performed on a FEI Tecnai 12 TWIN transmission electron microscope operating at an acceleration voltage of 100 kV or a FEI Talos 200SC FEG transmission electron microscope operating at an acceleration voltage of 200 kV. Negatively stained images obtained by the Tecnai were recorded using a SIS Megaview III wide-angle CCD camera and cryogenic images obtained by the Tecnai were recorded 16-bit 2K FEI Eagle bottom mount camera, all images obtained by the Talos were recorded using CETA direct detection CMOS camera. Fluorescence spectroscopy data was obtained using a Duetta fluorescence and absorbance spectrometer (Horiba Scientific, Irvine, CA). Quantitative polymerase chain reaction (qPCR) assays were conducted using a LightCycler 480 Real-Time PCR System (Roche Diagnostics, Rotkreuz, Switzerland).

Peptide amphiphiles (PAs) were synthesized using the standard 9-fluorenylmethoxycarbonyl (Fmoc) solid phase peptide synthesis technique. All peptides were synthesized on an Fmoc-Glu(OtBu)-Wang Resin. Fmoc deprotection was performed using 20% piperidine in N,N-dimethylformamide (DMF) for two fifteen-minute intervals. Following Fmoc removal, amino acids were coupled to the peptide chain at the molar ratio of 4:4:10 ratio of resin to Fmoc amino acid, hexafluorosphate benzotriazole tetramethyl uranium (HBTU), and N,N-diisopropylethylamine (DIEA) in DMF, the reaction was allowed to proceed for at least two hours. Palmitic acid was conjugated to the Fmoc-deprotected, N-terminus of the peptides at a ratio of 1:4:4:10 resin:palmitic acid:HBTU:DIEA in DMF and allowed to react for 12 hours. Completed peptide amphiphiles were cleaved from the resin and their side chains were deprotected through reaction in a solution of 92.5% trifluoroacetic acid (TFA), 5% triisopropylsilane (TIS), and 2.5% water for 3 hours. Following cleavage, the PA containing TFA was collected and the PA was precipitated through the addition of cold diethyl ether and centrifugation (repeated 2 more times). The precipitated PA was then allowed to dry in the fume hood overnight.

Following PA synthesis, PAs were dissolved in 0.1% v/v ammonium hydroxide (NH4OH) containing water and 0.1% v/v NH4OH containing acetonitrile (ACN). Molecules below 95% purity (as determined by analytical RP-HPLC) were purified using RP-HPLC in mobile phases of basic H2O and ACN. Collected fractions were subjected to matrix-assisted laser desorption/ionization time of flight (MALDI-TOF) or electron spray ionization (ESI) mass spectrometry to determine the fraction with the desired product. Correct fractions were combined and ACN was removed using rotary evaporation. PAs were then lyophilized and the purified powders were stored in a −20° C. freezer for future use.

Synthesis of 2-(Pyridyl-disulfanyl)ethanol (etpSS-Pyr) was adapted from a procedure described in Cheetham, Chem. Commun., 2014, 50, 6039-42, incorporated herein by reference. Briefly, 2-Aldrithiol (2.4 g, 10.89 mmol) was dissolved in MeOH (7 ml) and 2-mercaptoethanol (334 µl, 370 mg, 4.74 mmol) was added and allowed to react for three hours. The solution was diluted with 0.1% aq. TFA and purified by RP-HPLC. Product fractions were combined and solvents removed using rotary evaporation to give a pale yellow oil.

Figure 1B:
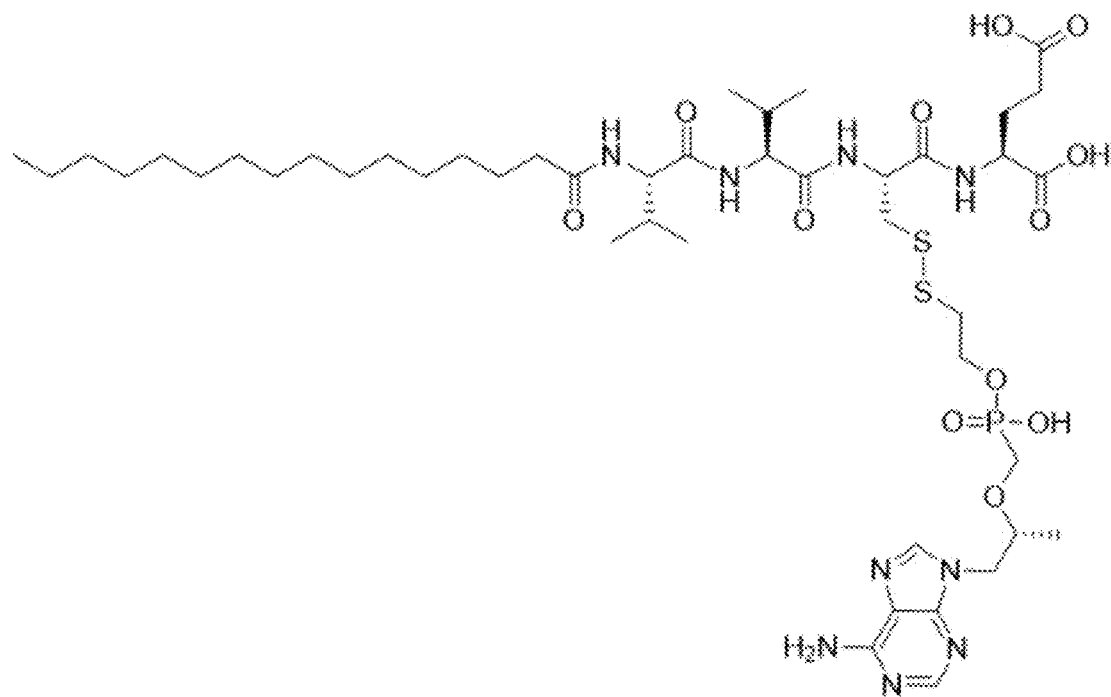
FIG. 1B shows a structure of an exemplary drug amphiphile TFV-PA2.
Figure 1C:
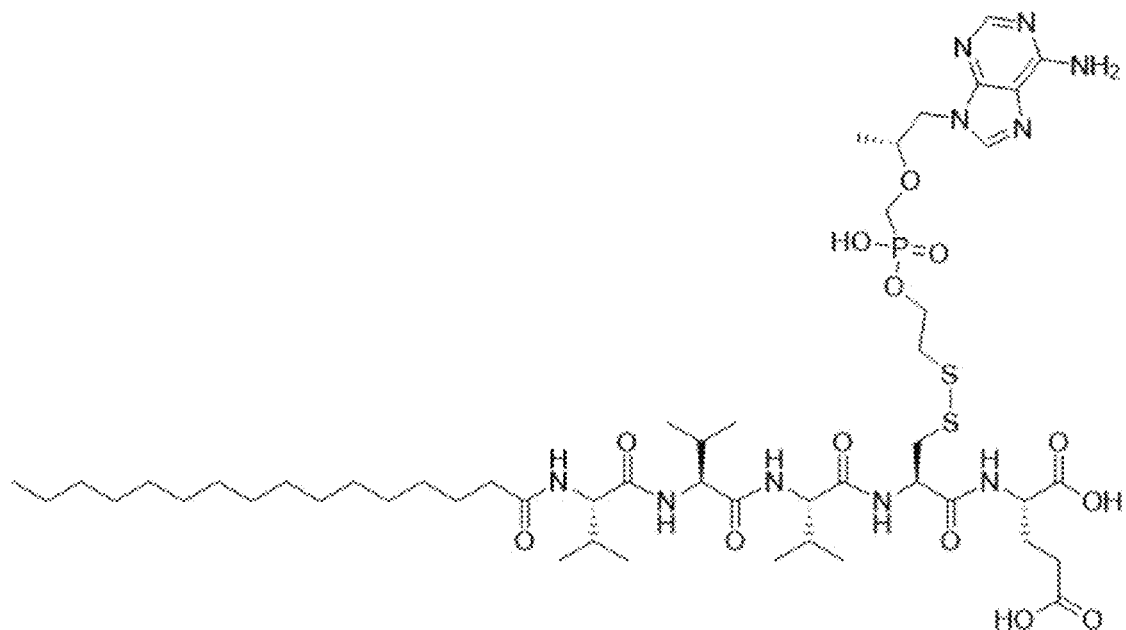
FIG. 1C shows a structure of an exemplary drug amphiphile TFV-PA3.
Figure 1D:
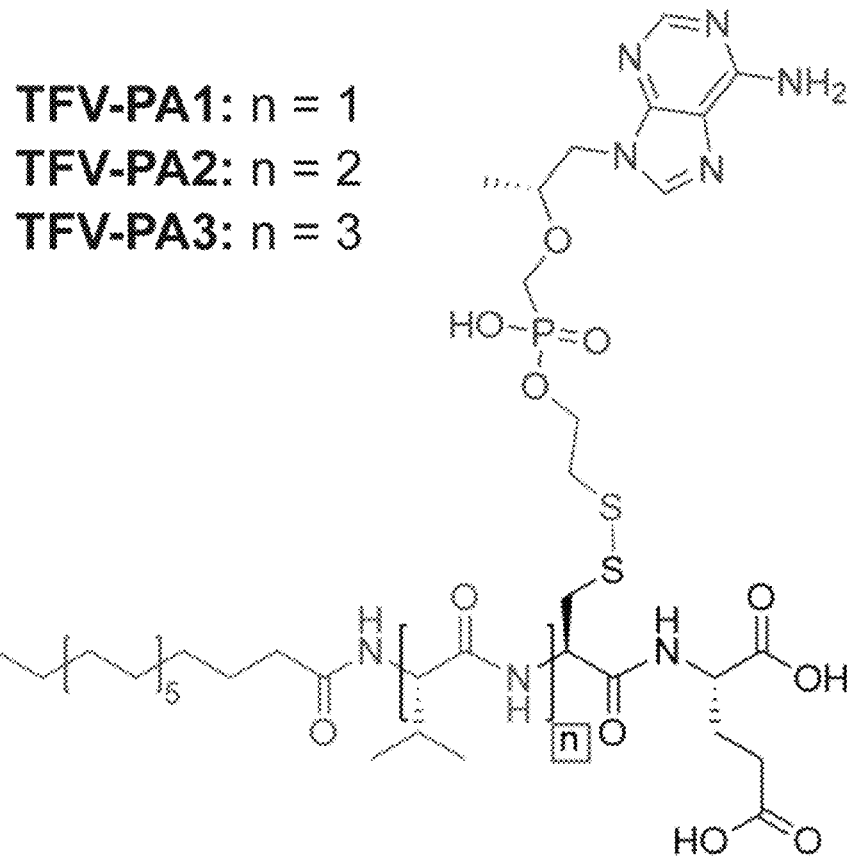
FIG. 1D shows a general structure of a class of drug amphiphiles.
Figure 2:
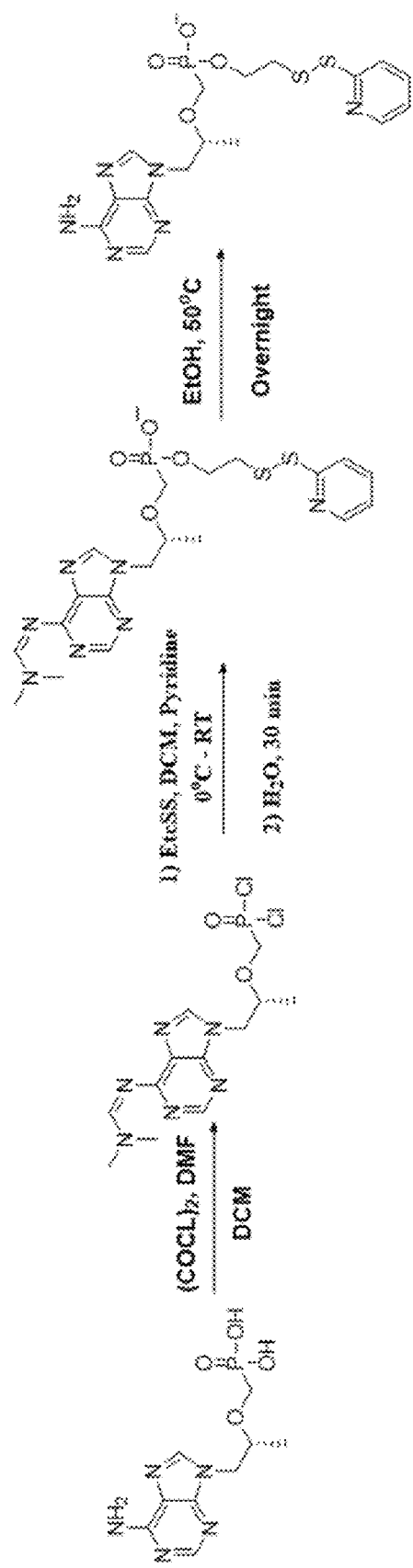
FIG. 2 shows a synthesis scheme for TFV-etpSS-Pyr.

Three TFV-PA were synthesized and studied during the experiments described herein. See FIG. 1A (TFV-PA1), FIG. 1B (TFV-PA2), and FIG. 1C (TFV-PA3). TFV-etpSS-Pyr was synthesized using an adaptation of a procedure described in Giesler, J. Med. Chem., 2016, 59, 10244-52, incorporated herein by reference. See FIG. 2 for the scheme. After evacuating the air and purging the reaction flask with argon, excess oxalyl chloride (0.9 mL, 10.52 mmol) was added dropwise to a stirring solution of DMF (160 µL, 2.09 mmol) and dry tenofovir (0.5 g, 1.74 mmol) dissolved in anhydrous dichloromethane (DCM, 20 mL) and allowed to react at RT under argon for 20 minutes. Excess solvent was then removed by rotary evaporation and the product was redissolved in anhydrous DCM (15 mL) and chilled to 0° C. using an ice bath and purged with argon. 1.1 equivalent of etpSS-Pyr (360 mg, 1.92 mmol) dissolved in anhydrous DCM (5 mL) was added to the chilled stirring solution, followed by the dropwise addition of pyridine (0.84 mL, 10.44 mmol) dissolved in anhydrous DCM (3 mL) under argon. The stirring solution was allowed to react at 0° C. for 15 minutes under inert conditions before being removed from the ice bath and allowed to warm naturally to RT and allowed to react closed to the atmosphere for an additional 3 hours. Water (470 µL, 26.09 mmol) was added to the stirring solution and the mixture was allowed to stir for an additional 30 minutes to quench the reaction. Solvent was removed via rotary evaporation and then the product was air dried for 30 minutes. The product was redissolved in EtOH (25 mL) and allowed to react at 50° C. overnight, vented to the atmosphere. Solvent was then removed by rotary evaporation and the product was redissolved in 0.1% aq. TFA (30 mL) for purification via acidic phase RP-HPLC. The desired product fractions were collected, subjected to rotary evaporation to remove ACN, and lyophilized to give TFV-etpSS-Pyr. 1H-NMR (400 MHz, CD3OD, 25° C., δ ppm) 8.39 (m, 2H), 8.34 (s, 1H), 7.84 (m, 2H), 7.22 (t, 1H), 4.28-4.48 (m, 2H), 4.12 (m, 2H), 3.98 (dd, 1H), 3.57-3.82 (m, 2H), 3.02 (t, 2H), 1.18 (s, 3H); MS (ESI): 457.2 [M+H]+, 912.9 [2M+H]+, 1368.7 [3M+H]+. The product was stored in a −20° C. freezer for future use.

TFV peptide amphiphiles (TFV-PAs) were synthesized by dissolving a 1:2 molar equivalent of PA (17.6-23.6 mg, 0.03 mmol) and TFV-etpSS-Pyr (27.4 mg, 0.06 mmol) in DMSO (1 mL), purging the reaction flask with nitrogen, and allowing the solution to stir for 5 days. The TFV-PAs were then dissolved in 20-30 mL of 70:30 0.1% v/v NH4OH H2O: ACN and purified via basic phase RP-HPLC (samples were run at a gradient of 5% to 55% ACN over 25 min). Collected fractions were analyzed using MALDI-TOF or ESI MS to determine the fraction containing the desired product. Correct fractions were combined, subjected to rotary evaporation, and lyophilized. TFV-PAs were then dissolved in deionized water and the pH of the solutions were tuned to 7.4 prior to aliquoting the solutions into cryo-vials. Purity and concentration of the TFV-PAs was assessed using analytical RP-HPLC. The aliquots were re-lyophilized and subsequently stored in a −20° C. freezer for future use.

Molecular weights of synthesized etpSS-Pyr and TFV-etpSS-Pyr were determined using ESI mass spectrometry. Molecular weights of synthesized PAs and TFV-PAs were also determined using ESI MS when MALDI-TOF MS analysis was unavailable. Samples were prepared for analysis by diluting 20 μL of aqueous sample solution (containing 0.1% v/v formic acid) with 200 μL methanol. Diluted samples were then diluted another 5 to 20 times using methanol within a 500 μL glass syringe to attain a final sample concentration of 0.1-1 μM. The samples were analyzed in positive ion mode.

Molecular weights of synthesized PAs and TFV-PAs were determined using MALDI-TOF mass spectrometry. Samples were prepared for analysis by depositing 2 μL of sinapic acid matrix (10 mg/mL in 1:1 v/v water/ACN with 0.05% v/v S4 TFA; Sigma-Aldrich, St. Louis, MO) onto a room temperature MTP 384 ground steel target plate (Bruker, Billerica, MA) and allowing the matrix to dry for 10 minutes. 1 μL of aqueous PA solution was then added to the spot of dried matrix followed by the immediate addition of 1 μL of sinapic acid matrix, which was mixed with the PA solution. The samples were then allowed to dry for 10-20 minutes. During MS analysis, the samples were irradiated with a 355 nm UV laser and analyzed in the reflectron mode.

Purity and concentration of TFV-PAs and intermediate products were confirmed using analytical RP-HPLC, monitoring the 220 and 260 nm wavelengths. To confirm purity, 25 μL of solution was injected into the HPLC and subjected to a gradient of 5% to 95% ACN over 15 minutes, in basic phase. Area under the curve (AUC) of the desired molecule's peak was compared to the sum of the AUCs for all peaks in the 220 and 260 nm RP-HPLC chromatographs to confirm product purity >95%. A calibration curve of TFV concentration was built by running different concentrations of TFV (ranging from 50 μM to 1 mM) on the HPLC in acidic phase at a gradient of 5% to 95% ACN over 15 minutes. The AUC of the peaks in the 260 nm (the absorbance of TFV) chromatograph were plotted against TFV concentration and the data was fit with a linear regression to give a TFV calibration curve. To determine the concentration of TFV-PA aliquots, a TCEP reduction assay was used as follows. 25 μL of solution was diluted with 25 μL of ACN and added to 3 mg of TCEP, the mixture was then vortexed and sonicated at 37° C. for twenty minutes to attain complete cleavage of the TFV from the peptide. 25 μL of the vortexed solution was subjected to HPLC analysis under acidic conditions and the 260 nm AUC of the TFV peak was used to calculate the concentration of the aliquot from the TFV calibration curve.

To confirm self-assembly of the TFV-PA, 1 mM aqueous TFV-PA solutions were prepared using deionized water and allowed to age for 48 hours at RT. Negative stained transmission electron microscopy (TEM) samples were prepared by depositing 5 μL of sample onto a 400 square mesh, carbon film copper grid (Electron Microscopy Services, Hatfield, PA). After 1 minute, excess sample was wicked away using filter paper, leaving a thin film of sample on the grid, which was allowed to dry for 2 hours. 7 μL of 2 wt % aqueous uranyl acetate was deposited on the grid and allowed to sit for 30 seconds before excess stain was wicked away with filter paper. The grids were allowed to dry for at least three hours before being imaged using the Tecnai 12 TEM. Nanobelt widths were measured using ImageJ software, 35 distinct structures were measured for each image. For cryogenic TEM, plasma cleaned 300-mesh lacey carbon-coated grids (Electron Microscopy Services, Hatfield, PA, USA) were mounted by the forceps on Vitrobot Mark IV (Thermo Fisher, Waltham, MA). 6 μL of 5 mM TFV-PA3 aqueous solutions were applied onto the grid, then blotted for 1 s at a blot force of 0. The grid was plunge-frozen into the liquid ethane reservoir in a Dewar precooled by liquid nitrogen. The vitrified samples were then transferred to a Gatan 626 cryo-holder on the cryo-transfer. The temperature of the cryo holder was maintained below −170° C. to prevent vitreous ice formation. The cryo-holder was transferred to the FEI Talos 200SC FEG transmission electron microscope for imaging. Cryogenic TEM images confirmed self-assembly.

A Nile Red encapsulation assay was used to determine the critical micellization concentration (CMC) of each design. TFV-PAs were treated with hexafluoroisopropanol (HFIP) and then excess HFIP was fully removed by evaporation. Aqueous solutions of the HFIP-treated TFV-PAs were prepared at various concentrations ranging from 0.1 to 500 μM. 10 μL of a 500 μM acetone-based solution of Nile Red was added to 1.5 mL microcentrifuge tubes and the acetone was allowed to evaporate off in the dark. 500 μL of each concentration for each TFV-PA was added to a tube with Nile Red. Solutions were aged for 2 days in the dark at RT. Samples were then run on the spectrofluorometer at an excitation wavelength of 550 nm, with three parallel emission spectra recorded from 580 to 720 nm. The emission intensity ratio of encapsulated versus free Nile red (635 nm/660 nm) was then plotted versus concentration and the CMC value was calculated using the point of transition from 660 nm to 635 nm emission (by calculating the intersection of the linear regressions fit to the two emission phases).

Circular dichroism was employed to determine the extent of intermolecular hydrogen bonding within the supramolecular assemblies. 1 mM concentration samples were prepared and allowed to age at room temperature for 48 hours.

Samples were then diluted to 100 μM concentration using deionized H$_2$O and 200 μL of sample was immediately loaded into a 0.1 cm path length quartz UV-vis absorption cell (Thermo Fisher Scientific, Pittsburgh, PA). Samples were analyzed using three repeated scans from 300 to 190 nm and high tension values for each spectrum were monitored to ensure they remained between 200 and 600 V. A background spectra of deionized water was acquired using the same run parameters. The three runs were averaged for each sample and the water background spectra was subtracted from the sample spectra. The averaged spectra was then normalized with respect to sample concentration and path length in order to convert from ellipticity (mdeg) to molar ellipticity (deg·cm$^2$·dmol$^{-1}$).

The critical gelation concentrations of the different TFV-PAs were assessed by preparing aqueous DA solutions at different concentrations (1, 2, 5, and 10 mM) and allowing them to age for 48 hours at RT. 100 μL of each solution was then transferred to a half dram glass vial and 10 μL of 10× phosphate-buffered saline (PBS) solution was added to trigger gelation via salt-screening and to give a final concentration of 1× PBS. Samples were subjected to an inversion test to assess formation of a self-supporting hydrogel.

Stability of the TFV-PAs and redox triggered release of free TFV was assessed by aging TFV-PA solutions in the presence and absence of 10 mM dithiothreitol (DTT). 200 M solutions of TFV-PA2 and TFV-PA3 solutions were prepared using deionized H$_2$O and allowed to age at RT for 24 hours. A 20 mM solution of DTT was prepared by diluting a stock 1 M DTT solution with 2× phosphate buffered solution (PBS). 500 μL of 2× PBS was added to an equal volume of each TFV-PA solution to give the DTT negative samples with a final TFV-PA concentration of 100 μM in 1× PBS. 500 μL of 20 mM DTT solution was added to an equal volume of each TFV-PA solution to give the DTT positive samples with a final TFV-PA concentration of 100 μM and 10 mM DTT in 1× PBS. Each experimental condition was prepared in triplicate. Solutions were allowed to age at 37° C. and 50 μL samples were collected at predetermined time points (0, 1, 2, 4, 8, 12, 24, 48, and 72 h), flash frozen in liquid nitrogen, and then stored in a −20° C. freezer. 2 μL of hydrochloric acid was added to the DTT positive samples upon collection to quench the reaction. Samples were thawed and immediately analyzed using the Agilent Infinity II RP-HPLC. The relative proportions of remaining TFV-PA were determined using the ratio of the AUC of the TFV-PA peak in the 260 nm chromatograph to that of the 0 hour samples. For select samples, 1 μL of solution was diluted in 900 μL MeOH and 100 μL 0.1% aq. formic acid and subjected to ESI MS to identify the molecules in the sample.

To study gel release, 5 mM and 10 mM solutions of TFV-PA2 and TFV-PA3 were prepared using deionized water and allowed to age at RT for 48 hours. 45 μL of each solution was aliquoted into three 0.5 mL microcentrifuge tubes and 5 μL of 10× PBS was added to each vial to form a hydrogel with a final concentration of 1× PBS. Gels were allowed to set for 5-10 minutes before 60 μL of 1× PBS was added to the surface as the release media. The vials were then allowed to age at 37° C. Every 2 days, 50 μL of gel release supernatant was collected and replaced with an equal volume of fresh 1× PBS. Samples were frozen and stored at −20° C. for future analysis by RP-HPLC. On select days, 5 μL of release supernatant was collected 24 hours after supernatant exchange and used to prepare a negatively stained transmission electron microscope grid for analysis with the Talos transmission electron microscope. The grid was prepared as described above, except the sample was blotted with 5 μL deionized water (wicked immediately) after the sample was wicked away to remove excess salts from the PBS. Once the release experiment was complete, samples were thawed and 1-2 mg of TCEP was added to 25 μL sample solution and an equal volume of acetonitrile, then vortexed and sonicated at 37° C. for 10 minutes to ensure complete cleavage of the TFV moiety from the TFV-PAs. 25 μL of the TCEP treated solution was run in acidic phase through the Varian ProStar analytical HPLC and the 260 nm AUC of the TFV peak was used to calculate the concentration of the aliquot from the TFV calibration curve.

Anti-HBV efficacy was evaluated on HepAD38 cells, using an adaptation of a procedure described in Ladner, Antimicrob. Agents Chemother. 41: 1715-20, 1997, incorporated herein by reference. HepAD38 cells were plated on collagen coated 96-well flat-bottomed plates at a density of 6×10$^4$ cells/well and grown for 3 days in the presence of 200 μL of Ham's F-12K (Kaighn's) Medium supplemented with 10% fetal bovine serum (FBS), 1% of an antibiotic solution (penicillin and streptomycin), and 0.3 mg/mL tetracycline at 37° C. in 5% carbon dioxide. On day zero the cells were washed with PBS and treated with tetracycline-free F-12K medium containing TFV, TFV-PA2, or TFV-PA3 (180 μL of medium supplemented with 20 μL of 10× concentration therapeutic solution to give 200 μL of medium at the final therapeutic concentration). Each therapeutic was screened at a minimum of five concentrations in quadruplicate. Water treated cells (180 μL of medium supplemented with 20 μL of H$_2$O) were used as the negative control. On day three the medium was removed and replaced with 200 μL of fresh tetracycline-free medium containing the test compound at the appropriate concentration. On day four, 150 μL of cell supernatant was collected and supplemented with 50 μL of nuclease free H2O, and DNA was extracted and eluted in 50 μL of nuclease-free water using QIAamp DNA blood mini kits (Qiagen, Germantown, MD) following the manufacturer provided spin protocol for DNA purification from blood or body fluids. HBV DNA was quantified by qPCR, using Integrated DNA Technologies PrimeTime Gene Expression Master Mix (Integrated DNA Technologies, Coralville, IA) and HBV TaqMan primer/probe (20×, Assay ID Vi03453405_s1, ThermoFisher Scientific, Pittsburgh, PA). A serial dilution of gBlocks Gene Fragments (Integrated DNA Technologies, Coralville, IA) of known HBV copy number was used as the standard for the absolute quantification of DNA copy number from cycle threshold values. All qPCR runs used the following cycling parameters for amplification of 2 μL of aqueous DNA: a preamplification cycle at 95° C. for 10 minutes, 50 cycles of 95° C. and 60° C., followed by a melt curve, in accordance with the manufacturer's protocol. Percent HBV production for each therapeutic concentration was determined based on average number of copies of HBV DNA produced by water treated cells and averaged between the three biological repeats of the assay before being plotted against concentration. GraphPad Prism software was used to calculate the IC50 values ("[Inhibitor] vs Normalized Response" non-linear regression equation).

TFV is hydrophilic. Accordingly, peptides were designed to have distinct hydrophilic and hydrophobic segments, a robust intermolecular hydrogen bonding sub-domain, and a relatively long alkyl tail. Thus, three molecules were designed that incorporate one to three valines at the N-terminus to balance increased TFV content with enhanced intermolecular associative interaction forming propensity. See FIGS. 1A, 1B, 1C, and 1D. The tenofovir moiety was covalently conjugated to a cysteine residue near the C-terminus of the peptide using a reducible disulfonyl-ethyl phosphonate linker (etpSS) to construct the TFV-bearing peptide amphiphiles (TFV-PAs, named TFV-PA1, TFV-PA2, and TFV-PA3, respective to the number of valines incorporated in the sequence). For all designs, palmitic acid was incorporated at the N-terminus as the hydrocarbon tail of the peptide amphiphile, and glutamic acid was included at the C-terminus to provide distinct amphiphilicity to the molecules. As confirmed by microscopy, the TFV-PAs self-assemble into filamentous structures in aqueous conditions. Self-assembly is driven be the hydrophobic collapse of the alkyl tails, with intermolecular hydrogen bonding of the peptide backbones driving axial growth. Experiments confirmed that the supramolecular structures physically entangle to form a hydrogel drug depot in situ in the presence of physiologically relevant salt-concentrations. These TFV-bearing peptide amphiphiles differ from previous drug amphiphiles because the therapeutic is not the hydrophobic component of the self-assembling system and is consequently not the major driving force behind supramolecular polymerization. While TFV still contributes to self-assembly behavior, by linking it to a peptide-amphiphile with strong self-assembling propensity, self-assembly is decoupled from therapeutic content. This provides a technology having modifiable design considerations (e.g., number and type of therapeutic moieties) without significantly impacting self-assembly, gelation, and release of the LAI drug delivery system. Such a coupling strategy results in a more general drug delivery platform that allows for future alterations so that the therapeutic-bearing peptide amphiphile design can be applied to other hydrophilic therapeutics.

Supramolecular morphology, stability, packing, and gelation are all relevant characteristics for clinical adaptation of the TFV prodrug hydrogelators. Accordingly, experiments were performed to characterize these features of the different TFV-PA designs. All three designs formed nanobelts more than 1 micron in length at 1 mM concentration, with structures increasing in width from 10.0±2.5, 11.8±1.3, to 18.9±3.0 nm for TFV-PA1, TFV-PA2, and TFV-PA3, respectively, as confirmed by cryogenic TEM images. This self-assembling propensity of all three TFV-PA designs is a surprising result because covalent conjugation of organophosphorus-based groups to peptide sequences has been used in conventional technologies to minimize or eliminate self-assembly or gelation, and cleavage of these groups in response to a trigger has been used previously to engineer controlled delivery systems.

Consequently, the construction of PAs that incorporate a phosphonate group and that also self-assemble and form gels in physiologically relevant conditions is a significant accomplishment. Without being bound by theory, it is hypothesized that the difference in width between the supramolecular structures is a result of hydrophobic interactions between valines that contributes to lateral growth of the filaments, with increased number of valines resulting in a corresponding increase in lateral growth and wider structures. This increase in nanobelt width also corresponded to an observable increase in persistence length of the filamentous structures. Surprisingly, despite an established correlation between flexibility of supramolecular structures and gelation propensity, the designs displayed improved visually confirmed gelation with increasing number of valines. The addition of phosphate buffered solution (PBS) (final concentration 1× PBS) to 5 mM concentration solutions of the three molecular designs resulted in only partial gel formation for TFV-PA1, weak gel formation for TFV-PA2, and robust gel formation for TFV-PA3. The critical gelation concentrations (CGCs) of the different designs were assessed by adding PBS (final concentration 1× PBS) to different concentrations of PA solutions and then performing a simple inversion test to demonstrate the formation of a gel by visual inspection. The CGCs of the different designs were determined to be between 5 and 10 mM for TFV-PA1, between 2 and 5 mM for TFV-PA2, and between 1 and 2 mM for TFV-PA3. Considering the desirability of instantaneous gelation for LAI formulation, 10 mM solutions of TFV-PA2 and TFV-PA3 were allowed to assemble in the presence of 10 mM Nile red and injected into 10× PBS. Both designs formed gels instantly upon injection; TFV-PA1 was not tested due to its inferior gelation properties.

Figure 3A:
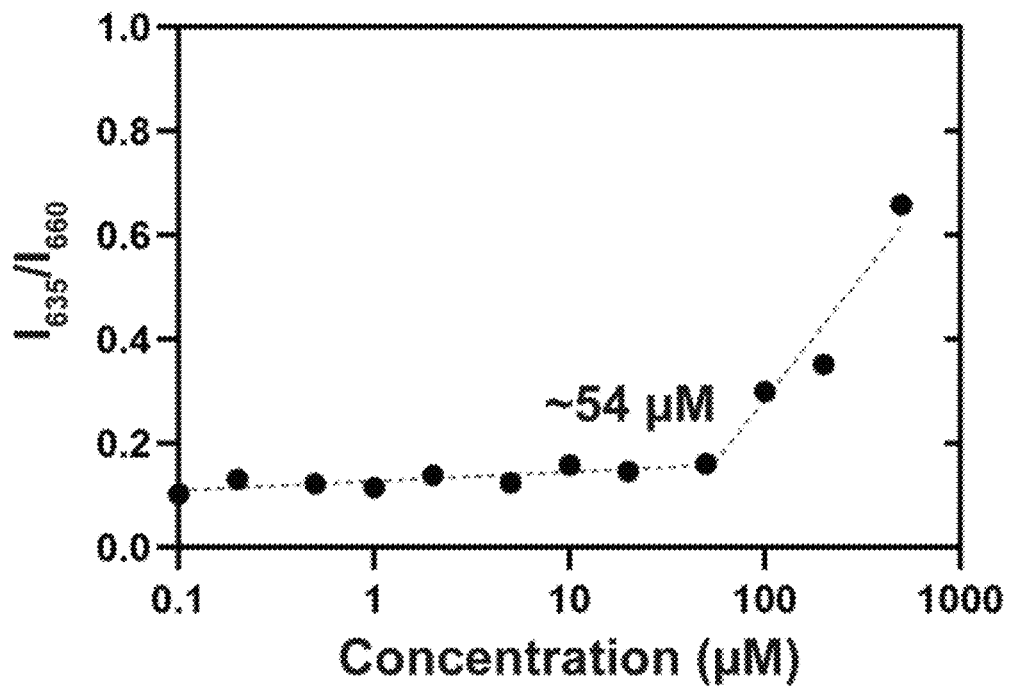
FIG. 3A is a plot of data showing the critical micellization concentration (54 μm) of TFV-PA1 as determined by a shift in the ratio of fluorescent intensity at 635 nm (indicating encapsulated Nile red) versus 660 nm (indicating free Nile red) (data are given as mean±SD, n=3).
Figure 3B:
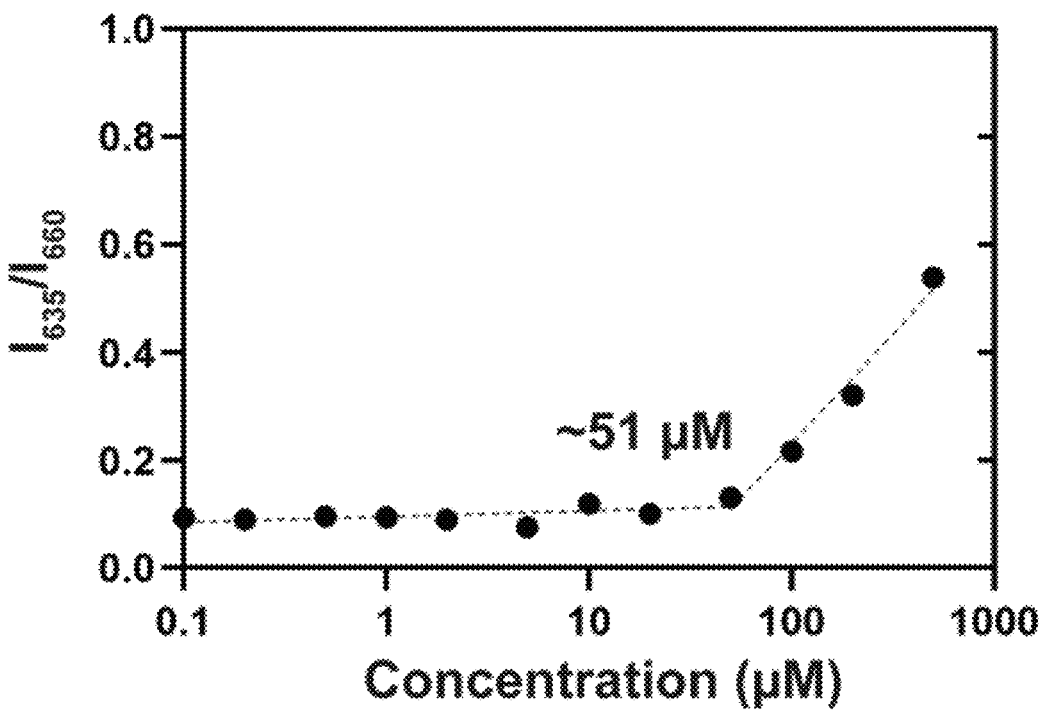
FIG. 3B is a plot of data showing the critical micellization concentration (51 μm) of TFV-PA2 as determined by a shift in the ratio of fluorescent intensity at 635 nm (indicating encapsulated Nile red) versus 660 nm (indicating free Nile red) (data are given as mean±SD, n=3).
Figure 3C:
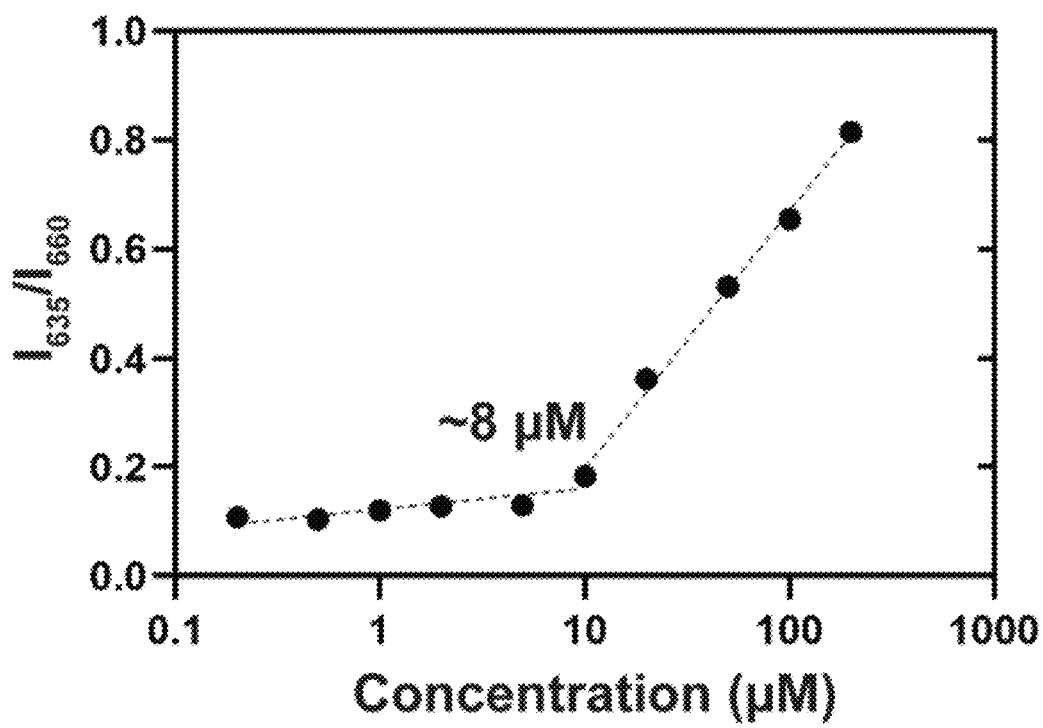
FIG. 3C is a plot of data showing the critical micellization concentration (8 μm) of TFV-PA3 as determined by a shift in the ratio of fluorescent intensity at 635 nm (indicating encapsulated Nile red) versus 660 nm (indicating free Nile red) (data are given as mean±SD, n=3).

To understand the unexpected trend of gelation propensity, experiments were conducted to evaluate the stability of the supramolecular structures. The critical micellization concentrations (CMCs) of the different designs were determined by a Nile red encapsulation assay, which uses a fluorometer to identify the differential fluorescence of encapsulated Nile red (635 nm) versus free Nile Red. An increase in the intensity at 635 nm indicates the presence of nanostructures. A lower CMC would correspond to enhanced stability of the structures and increased numbers of filaments, as more of the TFV-PAs are partitioned into supramolecular structures rather than existing as free monomers in solution, since the concentration threshold for supramolecular assembly is lower. Consequently, designs with a lower CMC are expected to have improved gelation propensity. In correspondence with the hypothesis that the lower CGC of the three-valine design was a result of its improved supramolecular stability, TFV-PA3 had the lowest CMC of the three designs, with the CMCs for TFV-PA1, TFV-PA2, and TFV-PA3 calculated as 54, 51, and 8 µM, respectively (See FIGS. 3A, 3B, and 3C). CMC differences between designs can be partially attributed to differences in the supramolecular packing/hydrogen bonding within the structures.

Figure 3D:
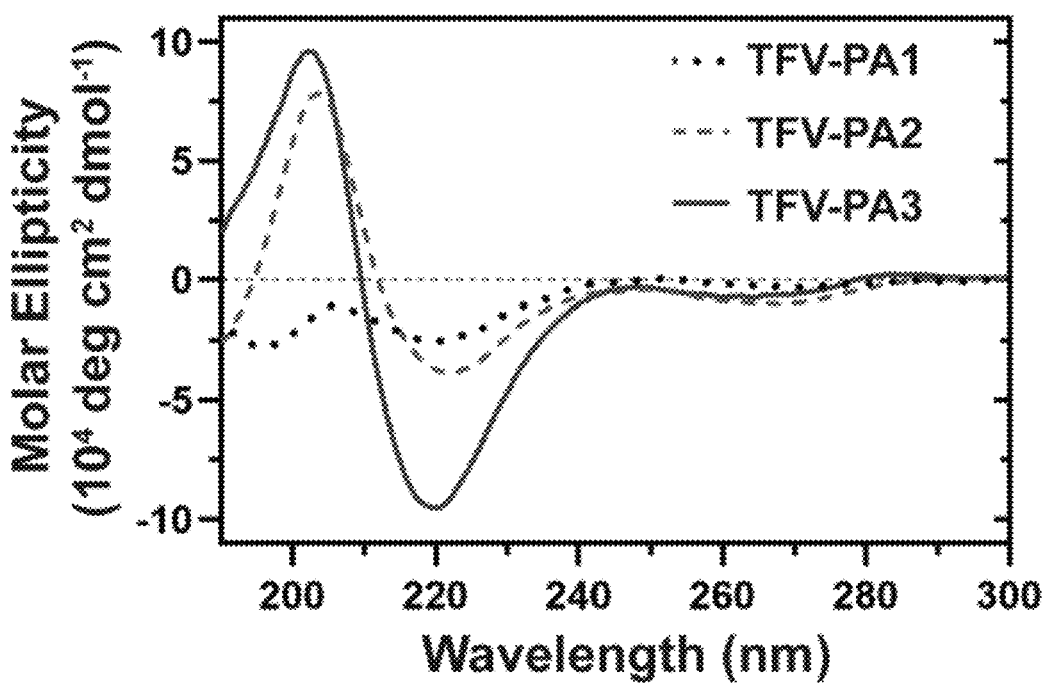
FIG. 3D shows circular dichroism spectra of assembled solutions for TFV-PA1, TFV-PA2, and TFV-PA3 (100 μM in $H_2O$), indicating the strength of associative hydrogen bonding between molecules.

Circular dichroism, which uses the differential absorption of left- and right-handed circularly polarized light, was used to characterize the secondary structure of the peptide portion of the TFV-PAs. The CD spectra for the different designs showed increasing hydrogen bonding with increased number of valines, as indicated by the increased depth of the negative peak in the 216 nm range (FIG. 3D). Further, valine is an amino acid having a high propensity to form associative interactions through hydrogen bonding. Without being bound by theory, it is speculated that the increased hydrogen bonding between TFV-PA1 and TFV-PA2 explains the different CGC values between the designs, despite their similar CMCs, because the intermolecular associations might influence gelation.

Consequently, adding hydrophobic amino acids increases the intermolecular interactions between the TFV-PAs, lowering the concentration of building units driving self-assembly and resulting in more stable supramolecular structures with slower release behavior. As anticipated, the design with the largest intermolecular hydrogen bonding peak, TFV-PA3, displayed the lowest CMC, indicating that the design could form nanostructures at lower concentrations and that are correspondingly more robust. These results suggest that the associative interactions between supramolecular building units can be manipulated by varying the number of hydrophobic amino acids, in this case valines, in the peptide sequences. The different assembly characteristics of the TFV-PA designs are significant for clinical development as previous work suggests that supramolecular stability has a significant impact on release, efficacy, and toxicity of self-assembling prodrugs. Monomer disassociation from supramolecular structures and diffusion of those monomers from the PA hydrogel into the surrounding medium partially governs the TFV-PA release rate; thus it is possible to prolong the release profile by modifying the CMC of the PA design. In this way, the technology provides for attaining and tuning long-acting release by simple design modifications of the TFV-PAs, such as increasing the number of valines.

During the development of embodiments of the technology described herein, in vitro gel release experiments were conducted to quantify release rates of free TFV-PAs from hydrogel depots. Hydrogels were formed at two different concentrations and then aged at 37° C. with a fixed volume of PBS solution to act as the release medium. The release supernatant was collected and exchanged at predetermined time points and sample concentrations were analyzed using RP-HPLC. Only the two and three valine designs were explored because the gels formed by TFV-PA1 solutions were not robust enough to last beyond a few days. As expected from the CMC of the designs, the TFV-PA2 hydrogels exhibited significantly faster release, with about 50% of the initial prodrugs released by day 14, than the TFV-PA3 hydrogels, which still retained more than 80% of the initial prodrugs on day 30 (See FIG. 4A). The TFV-PA2 percent release rate was independent of hydrogel concentration, with both the 5- and 10-mM gels showing similar percent release (48% and 56% on day 14 for the 10 and 5 mM gels respectively, FIG. 4A), and the 10 mM gels releasing twice the total number of nanomoles of prodrug released by the 5 mM gels (217-12 nanomoles and 126±7 nanomoles released on day 14, respectively). This, in combination with the observation that the average concentration in the release supernatant is significantly higher than the CMC calculated for the design (361±91 µM for 5 mM gels and 619±268 µM for 10 mM gels, versus 51 µM for the CMC), suggests that release from TFV-PA2 hydrogels is controlled by physical breakdown of the gel at the interface (surface erosion) rather than the CMC through disassociation of supramolecular structures and subsequent diffusion into the release media of the monomers (bulk erosion).

Figure 4A:
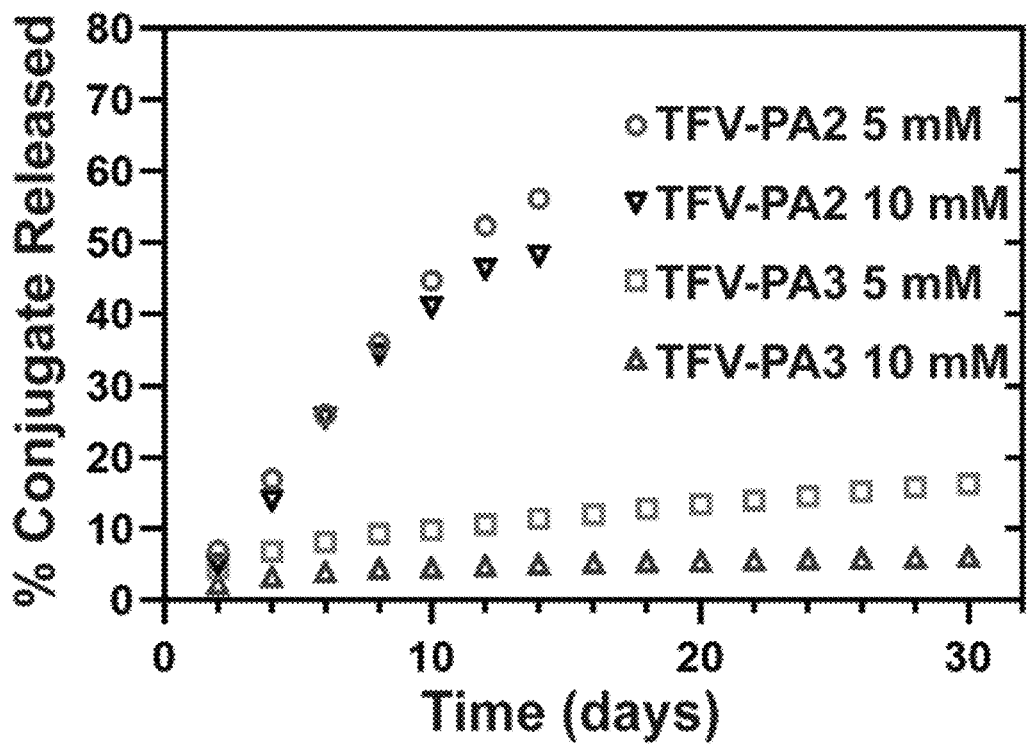
FIG. 4A shows plots of data showing the release behavior of prodrugs and hydrogels. Hydrogels were made from 5 mM and 10 mM solutions of TFV-PA2 and TFV-PA3 The in vitro prodrug release rate from hydrogels was measured by analytical HPLC. Prodrug release is represented as the percentage of conjugate contained in the original gels (data are given as mean±SD, n=3).

The dominance of surface erosion indicated that entire fibers are released from the gel rather than monomers of the conjugate. In accordance with this, TEM imaging of the release supernatant revealed dense networks of filaments >1 micron in length. In contrast, the percent release rate of the TFV-PA3 5 mM hydrogels was approximately twice that of the TFV-PA3 10 mM hydrogels, with 16.3±1.3% (36.7±3.0 nanomoles) of the 5 mM hydrogels and 6.1±0.5% (27.3±2.2 nanomoles) of the 10 mM hydrogels released on day 30 (FIG. 4A). TEM imaging of the release supernatant indicated short plaques of filaments for both the 5 and 10 mM TFV-PA3 hydrogels; thus, bulk erosion was more dominant than surface erosion for both concentrations. Additionally, the average concentration of release supernatant from day 8 onwards for the TFV-PA3 10 mM gels was 13.3±4.2 µM, which is only slightly higher than the calculated CMC of 8 µM. These results indicated that different mechanisms of gel dissolution are involved in release for the different designs, with the TFV-PA2 gels predominantly displaying surface erosion and the TFV-PA3 gels predominantly displaying bulk erosion. Accordingly, significant modulation of monomer release behavior can be attained by altering the number of hydrophobic amino acids in the TFV-PA designs.

Figure 4B:
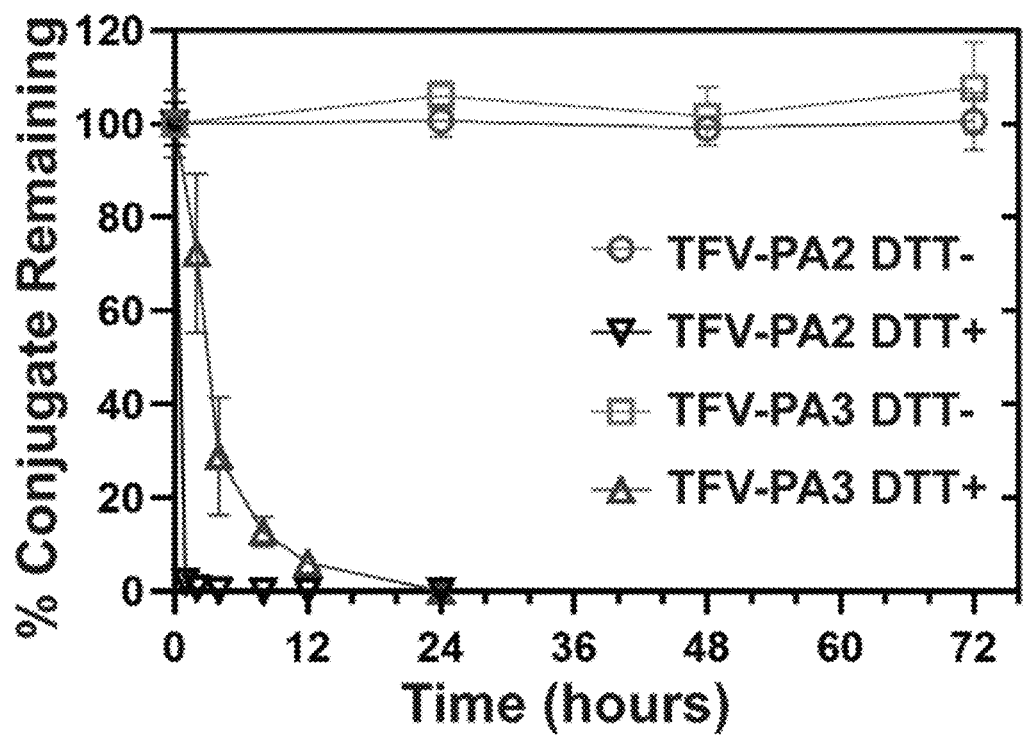
FIG. 4B is a plot of data showing the percent release of free TFV from 100 μM solutions of TFV-PA2 and TFV-PA3 in the presence and absence of 10 mM dithiothreitol (DTT) in 1× PBS (data are given as mean±SD, n=3).

During the development of the technology described herein, free drug release experiments were performed to demonstrate that TFV is cleaved from the peptide amphiphile under reductive conditions. Such studies demonstrate the ability of the TFV-PAs to provide an effective LAI delivery system in which the parent drug is released upon cellular uptake and then converted into its active diphosphate form by cellular enzymes, which is then incorporated into viral DNA via reverse transcription by viral enzymes. By incubating 100 µM 1× PBS solutions of TFV-PA2 and TFV-PA3 in the presence or absence of 10 mM of dithiothreitol (DTT), a known reducing agent, and then quantifying remaining prodrug using reverse-phase analytical HPLC, data indicated that the prodrugs are stable at 37° C. and in 1× PBS for 3 days and that TFV is quickly released in the presence of DTT, with more than 90% of TFV released after 1 hour for TFV-PA2, more than 70% of TFV released after 4 hours for TFV-PA3, and all TFV released by 24 hours for both designs (FIG. 4B).

ESI mass spectrometry was used to confirm the release of the parent drug; data indicated no prodrug remaining visible in the spectra of the 24-hour release samples. Instead, cleaved peptide was indicated in the spectra of all DTT positive samples, confirming the reduction of the disulfide bond. Intact prodrug was visible in the spectra of the 2- to 8-hour TFV-PA3 release samples, further indicating the incomplete conversion observed by RP-HPLC for samples incubated for less than 12 hours. Without being confined by any particular theory, the mechanism of free TFV release is believed to correspond to that previously reported by Pradere (Chem. Rev., 2014, 114, 9154-18).

Figure 5:
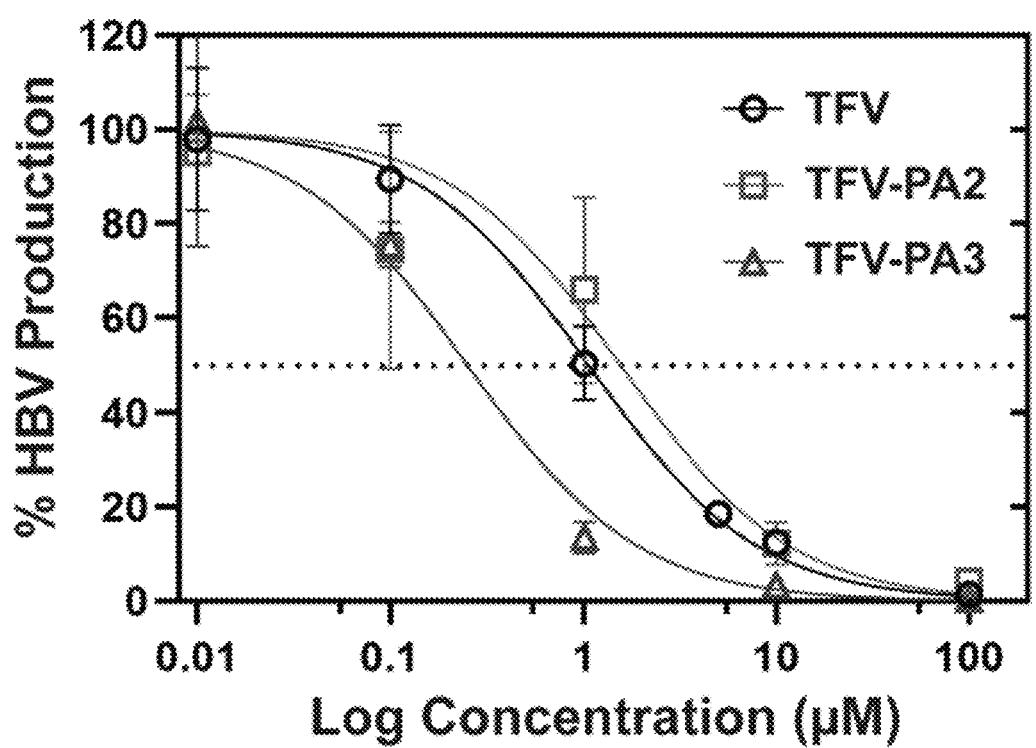
FIG. 5 is a plot of data collected from an in vitro antiviral efficacy assay. Data are the percent reduction of HBV production as quantified by qPCR of cellular supernatant for HepAD38 cells treated with varying concentrations of TFV and TFV prodrugs. Water treated cells were used as a negative control. Data are provided as mean±SD (p>0.05 one-way ANOVA, n=3). IC50 values were calculated as 1.1, 1.5, and 0.25 µM for TFV, TFV-PA2, and TFV-PA-3, respectively.
Figure 6A:
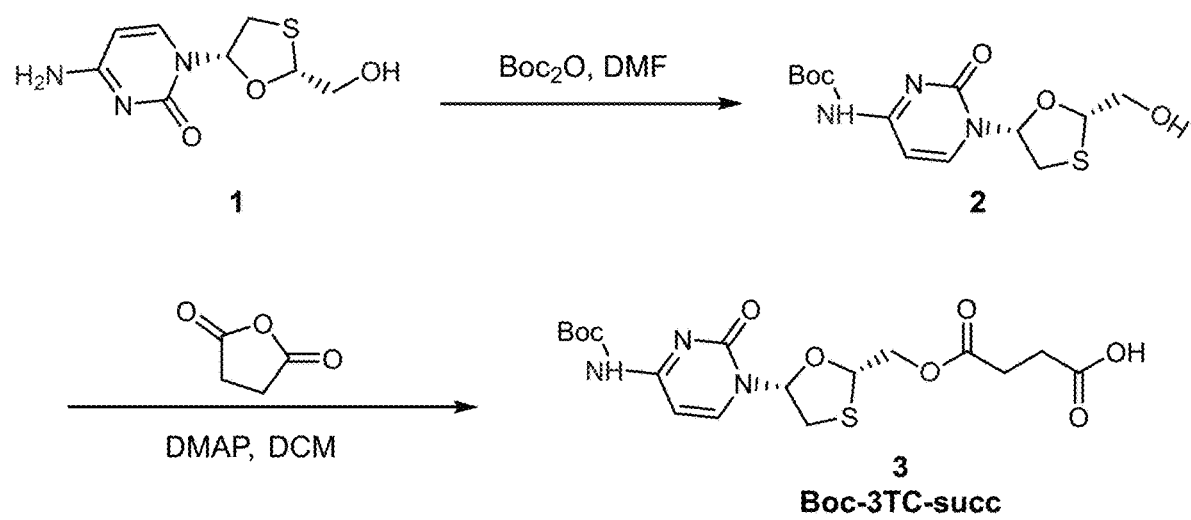
FIG. 6A shows a synthesis scheme for producing Boc-3TC succinate.
Figure 6B:
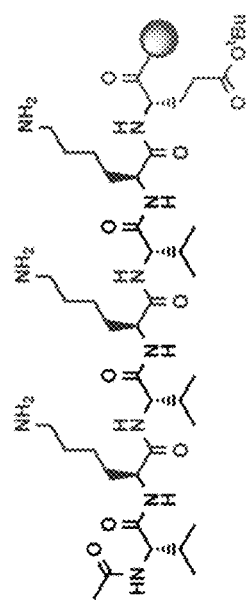
FIG. 6B shows a synthesis scheme for a conjugation reaction for synthesizing a lamivudine prodrug comprising a plurality of drug units.
Figure 6B:
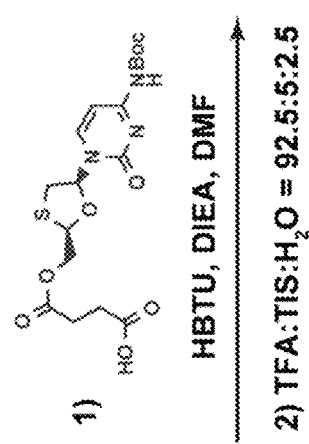
Figure 6B:
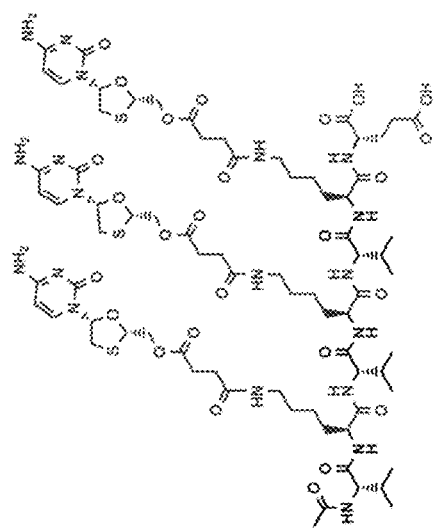
Figure 7:
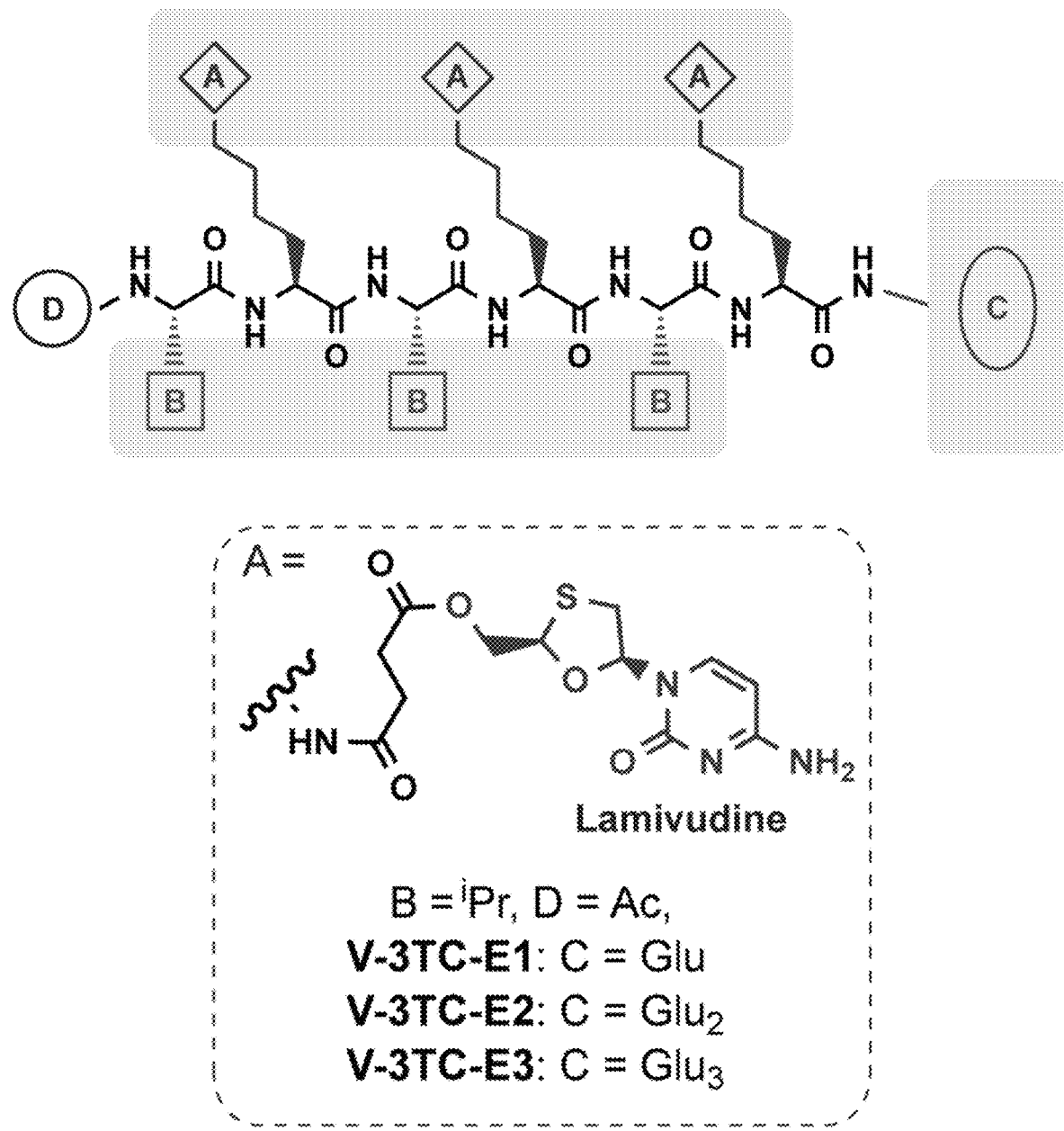
FIG. 7 shows a general structure of a class of drug amphiphiles.
Figure 8:
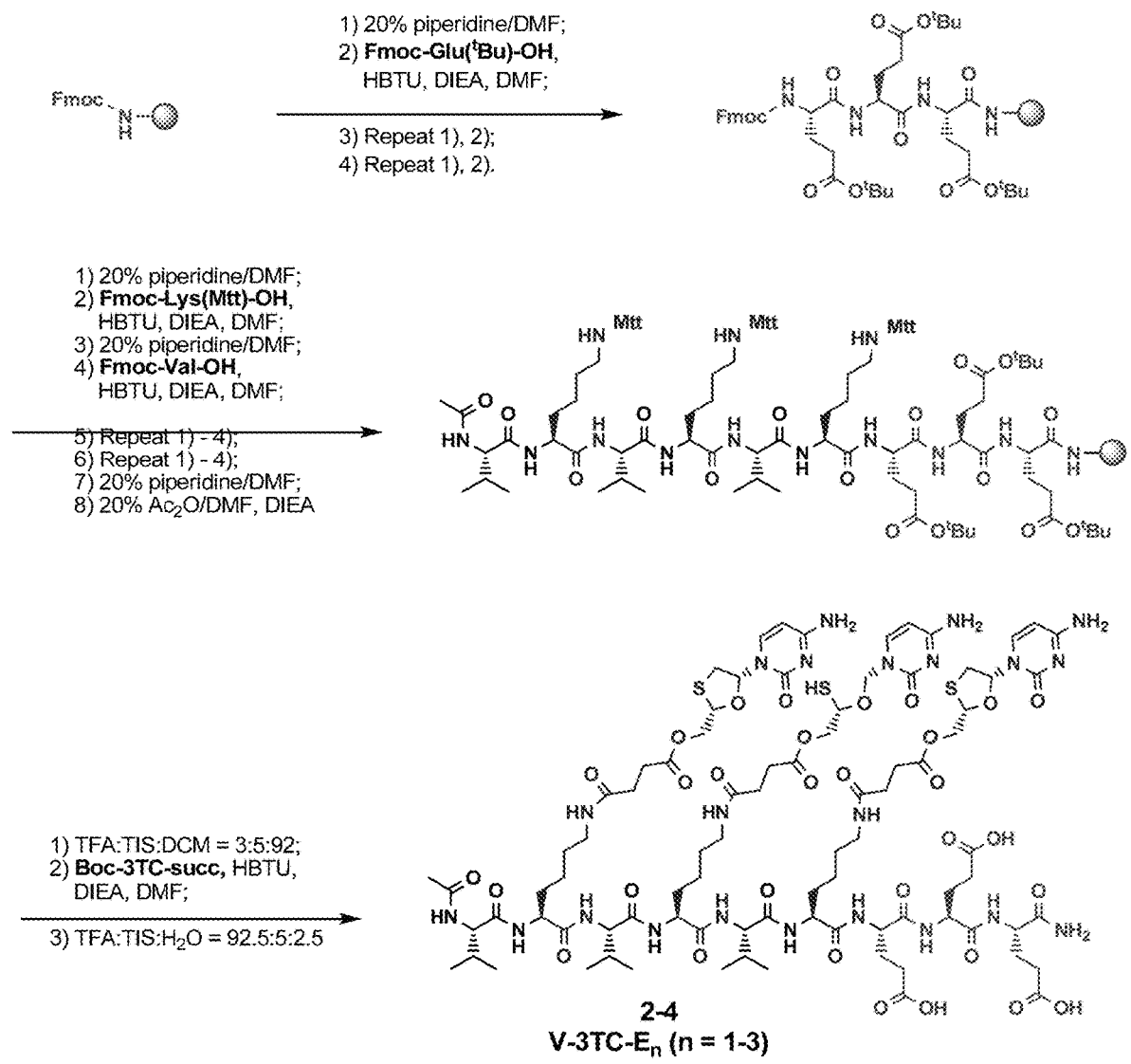
FIG. 8 shows a synthesis scheme for a solid phase synthesis of ARV DA prodrugs comprising a plurality of drug units.

Next, experiments were conducted to study the relationship of peptide conjugation with antiviral efficacy of the prodrug hydrogelators. To assess the anti-HBV efficacy of the prodrugs, HepAD38 cells (from an immortal cell line stably transfected with the HBV genome) were treated with varying concentrations of TFV, TFV-PA2, or TFV-PA3, using water treated cells as a negative control, following the established protocol for the cell-line as described in Ladner, supra. The cell supernatant was collected and subjected to qPCR analysis to quantify the copies of HBV DNA released from the cells. A dose response —inhibition curve was fit to the data to calculate the IC50 values for each therapeutic from the averaged biological repeats (FIG. 5). The extrapolated IC50 values for TFV, TFV-PA2, and TFV-PA3 were 1.1 (95% CI: 0.79-1.4), 1.5 (95% CI: 0.70-3.4), and 0.25 (95% CI: 0.16-0.41) M. The determined IC50 value for TFV falls within the range of values for the HepAD38 cell line reported in literature (0.14 to 5.46 µM). Critically, the antiviral studies indicated that peptide conjugation does not negatively impact antiviral efficacy. This is significant because previous work has demonstrated that filamentous self-assembly reduces cellular uptake of conjugates. Furthermore, there was a consistent trend in all biological repeats of lower IC50 values for TFV-PA3, indicating that conjugation of TFV to this peptide amphiphile improves efficacy. Without being bound by theory, it is speculated that the trend results from the increased hydrophobicity of the three-valine prodrug, which should improve membrane permeability. Accordingly, further experiments would confirm the mechanism of cellular entry and the membrane permeability of the TFV-PAs.

Example 2—Lamivudine Peptide Amphiphiles

During the development of embodiments of the technology provided herein, experiments were conducted to conjugate lamivudine (2',3'-Dideoxy-3'-Thiacytidine), also known as 3TC, to peptide amphiphiles to provide an antiviral prodrug (antiretroviral peptide drug amphiphile or ARV DA).

The technology provided herein relates to supramolecular hydrogelators formed by self-assembling drug amphiphiles, e.g., to provide a long-acting delivery system for lamivudine. In some embodiments, the drug amphiphiles comprise alternating hydrophilic-hydrophobic peptide conjugates that spontaneously associate into filamentous nanostructures in aqueous solution. With the ability to form stable hydrogels under physiological conditions, this supramolecular hydrogelator is well-tolerated and provides a linear, sustained release of a hydrophilic antiviral agent for up to 8 weeks in vivo following subcutaneous administration.

Rink Amide MBHA resin was purchased from Chem-Impex (Wood Dale, IL). Fmoc-protected amino acids and HBTU used for ARV DA synthesis were sourced from AAPPTec (Louisville, KY). Lamivudine (3TC) was purchased from Sigma-Aldrich. All other reagents were purchased from Sigma-Aldrich, TCI, Alfa Aesar or VWR and used as received. Reverse-phase HPLC was performed using a Varian PrepSstar SD-1 HPLC system (Agilent Technologies, Santa Clara, CA) with a Varian 440-LC collector. Purified fractions were lyophilized using a Labconco FreeZone 4.5L-50C Freeze Dryer (Kansas City, MO). The Mass Spectrometric data was obtained on a Thermo Scientific LCQ Fleet ion-trap mass spectrometer (Waltham, MA). 1H NMR spectra were recorded on a Bruker Avance 400 MHz NMR spectrometers.

Boc-3TC succinate was synthesized according to the scheme shown in FIG. 6. As shown in FIG. 6, 3TC (1, 2.00 g, 8.72 mmol) was mixed with Boc$_2$O (2.60 g, 12.2 mmol) in N,N-Dimethylformamide (DMF). The reaction was stirred at 50° C. for 24 h. After concentrating the resulting solution in vacuo, the residue was dissolved in 100 mL dichloromethane (DCM), washed with 100 mL saturated NaHCO$_3$, and then with 100 mL brine. After drying the organic layer with MgSO$_4$ anhydrous, the solvent was removed using a rotary evaporator, affording 2 used for next reaction without further purification.

Compound 2 (2.68 g, 8.14 mmol), succinic anhydride (1.22 g, 12.21 mmol), and 4-dimethylaminopyridine (DMAP, 74.5 mg, 0.60 mmol) were stirred in 40 mL anhydrous DCM. Diisopropylethylamine (DIEA, 2.10 mL, 12.2 mmol) were added to the reaction. The resulting solution was stirred at room temperature for 20 h. 40 mL of water was charged to the solution and stirred for 1 h. The solution was then acidified with 2 M HCl to pH=2. The crude mixture was collected by filtration and purified by flash column chromatography on silica gel to give Boc-3TC-succinate (3) as a white solid (1.72 g, 46% yield for the two steps). $^1$H-NMR (400 MHz, CDCl$_3$, 25° C., ppm): 7.98 (d, J=7.7 Hz, 1H), 7.22 (d, J=7.6 Hz, 1H), 6.20 (t, J=4.8 Hz, 1H), 5.43 (dd, J=7.7, 2.5 Hz, 1H), 4.69 (dd, J=12.2, 7.7 Hz, 1H), 4.36 (dd, J=12.2, 2.5 Hz, 1H), 3.60 (dd, J=12.1, 5.2 Hz, 1H), 3.08 (dd, J=12.1, 4.3 Hz, 2H), 2.68 (s, 4H), 1.51 (s, 9H). ESI-MS calculated for [M+H]+($C_{17}H_{24}N_3O_8S$): m/z=430.22, found: 430.30.

ARV DAs were synthesized on Rink Amide MBHA resin (0.5 mmol) using standard Fmoc-solid phase peptide synthesis. Fmoc deprotections were performed using 20% piperidine in DMF, and the reaction vessel was shaken for 15 min on a Burrel wrist-action shaker. This procedure was repeated one more time, and the resulting resin was washed 3 times with 10 mL DMF and 10 mL DCM. The coupling reaction was carried out by shaking the resin in a solution of HBTU (0.758 g, 2.0 mmol), Fmoc-protected amino acid (2.0 mmol), and DIEA (0.90 mL, 5.0 mmol) in 15 mL DMF for 2 h. Acetylation was performed 2 times after N-terminal Fmoc deprotection using 15 mL 20% Ac20 in DMF and 100 µL DIEA. The 4-methyltrityl (Mtt) group on the side chain of Lys(Mtt) was selectively deprotected by shaking the resin in 20 mL TFA/TIS/DCM (3:5:92) for 3 times. Then 3 was conjugated onto the deprotected lysine using the same method as amino acid coupling reaction described earlier. The peptide was cleaved with a solution of TFA/TIS/H$_2$O (92.5:5:2.5) for 3 h. The cleavage mixture was evaporated in vacuo reduced pressure and the crude peptide was precipitated in chilled dry diethyl ether. The crude peptide was purified using RP-HPLC with an Agilent Zorbax Extend-C18 Reverse-Phase column (5 µm, 150×21.2 mm). Product identity was analyzed by ESI-MS (Figure S3-S5) and lyophilized to obtain final products as white powders. The products were re-dissolved, aliquoted, re-lyophilized, weighed and stored at −20° C. The purity of ARV DAs was proven by analytical RP-HPLC using an Agilent Zorbax Extend-C18 RP column (5 µm, 150×4.6 mm) with 20 L injection volume. A linear ramping of 5-95% water/MeCN at a flow rate of 1.0 mL/min was used as the gradient condition.

The self-assembly of ARV DAs was promoted by dissolving the conjugates into deionized water at a concentration of 5 mM. The solutions were sonicated for 5 min and then aged for 1 day at room temperature. Stock solutions for TEM were prepared by diluting the solution above to 500 µM. Conventional TEM samples were prepared by adding a 7.5 µL droplet of stock solution onto a 400-mesh carbon-coated copper TEM grid. The excess solution was wicked away using filter paper. 7.5 µL of 2% uranyl acetate solution was then placed on the grid as a staining agent. The excess staining solution was removed after 30 s and the grid was left to dry before imaging. Conventional TEM images were obtained on a FEI Tecnai 12 TWIN TEM operating at 100 kV, equipped with a SIS Megaview III wide angle CCD camera and a 16-bit 2K FEI Eagle bottom mount camera.

All the 300-mesh lacey carbon-coated grids (Electron Microscopy Services, Hatfield, PA, USA) used for cryo-TEM imaging were pretreated with GLOQUBE Plus Glow Discharge System to render the lacey carbon surface hydrophilic. The lacey carbon grid was mounted by forceps on Vitrobot Mark IV (Thermo Fisher, Waltham, MA), and 6 µL of a 1 mM stock solution was loaded onto the grid. The grid was blotted and plunged into a liquid ethane reservoir in a Dewar precooled by liquid nitrogen. The vitrified samples were then transferred to a Gatan 626 cryo-holder on a cryo-transfer stage cooled by liquid nitrogen. The cryo-holder was transferred to the scope for imaging. The temperature of the cryo-holder was maintained below −170° C. to prevent sublimation of vitreous water. All images were recorded by the FEI Eagle camera.

Stock solutions of ARV DAs were diluted to 100 µM to obtain the CD spectra for each DA. The diluted solution was transferred to a 1 mm path length flat quartz cell. All CD spectra from 200 to 300 nm were recorded using a Jasco J-710 spectropolarimeter (JASCO, Easton, MD) at room temperature. Signals of the solvent were recorded to subtract solvent background from each sample. Data was normalized to DA concentration and path length.

The zeta potential measurements were performed on a Zetasizer Nano ZS90 (Malvern Instruments Ltd., UK). The solutions were prepared by diluting the stock solution to 200 µM. Samples were loaded in capillary cells and equilibrated for at least 5 min prior to measurement. The average values and their standard deviations are calculated from three replicate measurements. Variations of the zeta potential value over time were determined by measuring the solutions at different time points.

To measure the CMC of ARV DA, a Nile Red stock solution was prepared in acetone at 500 μM. 10 μL of the Nile Red solution was added to the bottom of 0.5 mL microcentrifuge tubes and allowed to dry in a dark area. 500 μL of each solution was subsequently added to the Nile Red containing vials and aged overnight. The emission spectra between 580 and 720 nm for each sample were recorded on an AVIV ATF 105 SpectroFluorimeter at an excitation wavelength of 550 nm. The CMC value was determined based on the ratio of emission intensity at 635 nm ($\lambda_{max}$ of Nile Red in hydrophobic environment) and 660 nm ($\lambda_{max}$ of Nile Red in aqueous environment).

20 μl of 10× PBS was added to 180 μl of ARV DA solution, followed by gentle mixing. Rheological experiments were performed using an Anton Paar rheometer using an 8-mm parallel-plate geometry. To measure the in vitro release profiles of ARV DA, 60 μL of PBS was placed onto the surface of 200 μL hydrogel and the sample was incubated at 37° C. At each time point, 50 μL of PBS was carefully collected from the surface of gel and replaced with the same volume of fresh buffer. The release study was repeated two times. The concentration of released ARV DA was determined using RP-HPLC using an Agilent Zorbax Extend-C18 RP column (5 μm, 150×4.6 mm) with 20 μL injection volume. A linear ramping of 5-95% water/MeCN at a flow rate of 1.0 mL/min was used as the gradient condition.

Experiments were conducted to evaluate in vivo hydrogel degradation. In these experiments, male Balb/cJ mice at 8-10 weeks of age were injected with the drug conjugate V3TCE3 (75 mg/kg 3TC-eq.) subcutaneously. The mice were photographed and sacrificed at different time intervals (Day 0, 1, 7, 14, 28, 35, 42). The remaining hydrogel sample was photographed, and carefully collected and dissolved in water/MeCN 8:2. The concentration of the remaining drug was determined using HPLC to calculate the remaining weights of the undegraded hydrogel.

In vivo pharmacokinetics and biodistribution were studied in male Balb/cJ mice at 8-10 weeks of age that were injected with 3TC or the drug conjugate V3TCE3 (75 mg/kg 3TC-eq.) subcutaneously. Whole blood samples were collected at 1, 3, 5, 7, 14, 21, 28, 35, 42, and 49 days after administration. At day 28 and 56, Animals were humanely euthanized, and tissues (liver, lung, lymph nodes, kidneys, and spleen) were collected for quantitative drug analysis.

For blood analysis, plasma was prepared by centrifugation of blood collected in heparinized tubes at 2000× g for 5 min. 3TC and V-3TC-E3 were extracted from plasma (20 μL) using 1 mL of acetonitrile. 10 μL of 500 ng/ml Emtricitabine solution was added to each sample as internal standard (IS), which gave a final IS concentration of 50 ng/mL after reconstitution. Samples were dried under a $N_2$ stream, reconstituted in 100 μl of 80% v/v LC-MS grade $MeOH/H_2O$. 10 μl of the sample solution was injected into Waters Acquity/Xevo-G2 UPLC/MS system (Milford, MA) for analysis.

For tissue analysis, an optimized amount of tissue sample was processed using a tissue homogenizer in 5 volumes of 90% v/v LC/MS grade $MeCN/H_2O$. 100 μL Tissue homogenate was mixed with 90 μL of 90% v/v LC/MS grade $MeCN/H_2O$, 10 μL of LC-MS-grade water, and 10 μL 500 ng/ml Emtricitabine solution (as IS). After extraction, 10 μl of the sample solution was injected into Waters Acquity/Xevo-G2 UPLC/MS system (Milford, MA) for analysis.

Standard curves of 3TC or V3TCE3 were prepared in blank mouse plasma in the range of 0.7-7000 ng/mL and 0.25-2500 ng/mL of corresponding compounds, respectively. Emtricitabine solution was added to each sample as internal standard (IS) to give a final IS concentration of 50 ng/mL. Quantitative analysis was performed based upon the ratio of 3TC peak area and IS peak area.

Three ARV DA were designed and studied. See FIG. 7. FIG. 8 shows a scheme for the solid-phase synthesis of ARV DA described herein (V-3TC-E1, V-3TC-E2, and V-3TC-E3). Each member of this series of supramolecular hydrogelators comprises an amphiphilic peptide segment and a hydrophilic NRTI moiety. The technology provided herein improves conventional technologies in which covalent linkage of hydrophobic drug moieties to various hydrophilic peptide segments provides drug amphiphiles that spontaneously associate into supramolecular filaments in water. As described herein, drug molecules were incorporated onto the sidechain of a hydrophilic-hydrophobic peptide to provide a drug-amphiphile that finds use for long-acting release of hydrophilic therapeutic agents.

As shown in FIG. 7, the molecules are designed to comprise an alternating valine-lysine (e.g., VKVKVK) peptide pattern, which provides: 1) multiple conjugation sites to improve drug loading efficiency; and 2) maintains two functional sites to tune supramolecular properties. Valine was chosen as the hydrophobic component because it forms or promotes the formation of β-sheet secondary structure. Lysine provides functional sites from its side chain for drug conjugation. A covalent linkage is formed between the hydrophilic NRTI, 3TC, and the side chain of lysine segments using a succinate linker. The hydrophilicity and the overall surface charge is manipulatable by the number of glutamic acids at the C-terminus. The N-terminus of the peptides was capped with an acetyl (—Ac) group and more potential functions can be incorporated by substituting the end —Ac.

In brief, the peptide segment of Ac-VKVKVK-$E_n$ (n=1-3) was synthesized using standard Fmoc solid-phase synthesis protocols. After the introduction of a tert-butyloxycarbonyl (Boc) protecting group, the 3TC-succinate prodrug was firstly synthesized and characterized by conjugating with succinate anhydride. The resulting prodrug molecule was further grafted onto the lysine side chains (FIG. 7 and FIG. 8). The peptide-3TC conjugates are obtained by cleaving from the peptide resin. The final product was purified using reversed-phase HPLC, and the products were confirmed using analytical HPLC and ESI mass spectrometry.

An intermolecular hydrogen bonding network can be formed between two or more peptide backbones. For instance, amyloid peptides form supramolecular nanostructure. Without being bound by theory, review of the molecular structure and molecular characteristics indicate that the hydrophobic valine faces pack one another to create facial amphiphiles, which consequently stabilize the fully extended conformation. Further, it is contemplated that the other face is thus lined with hydrophilic 3TC attached to the alternating lysine residues. To mitigate the poor water solubility caused by the hydrophobic packing, the glutamic acids in the C-terminus counteract the hydrophobic interactions by hydrogen-bonding and charge repulsion. By increasing the number of glutamic acids, the negative charge repulsion is designed to impact the packing pattern of the resulting drug conjugate. The expansion of the hydrogen-bonding network into lengthy fibers is reminiscent of natural and manufactured amyloid nanofiber mimics. Upon dissolution in water, the conjugates can spontaneously assemble into supramolecular 1D nanostructure.

To demonstrate the gelation properties of each molecule, experiments were conducted to study their self-assembly behavior and structural morphology in aqueous solution. The DAs were dissolved at 1 mM in water and aged for 24 h at room temperature before observing their assemblies. Samples were aged overnight at room temperature to eliminate kinetic effect. Transmission electron microscopy (TEM) images revealed V-3TC-E1, V-3TC-E2, and V-3TC-E3 formed one-dimensional nanostructures over several micrometers in length. The length of V-3TC-E2 and V-3TC-E3 are significantly longer than that of V-3TC-E1, indicating a closer lateral packing in V-3TC-E1. V-3TC-E2 and V-3TC-E3 assembled into filamentous morphologies, and widths of the filaments averaged approximately 7 nm and 12 nm. V-3TC-E1 exhibited a twisted ribbon morphology with an average width of approximately 60 nm. Data collected revealed the twisting tendency for V-3TC-E1 and V-3TC-E2 with varying degrees to form nanoribbons and interwound filaments, respectively, while no twisting was observed in V-3TC-E3. Without being confined by theory, this difference in twisting ability may attribute to the electrostatic repulsion from glutamic acids. To verify how glutamic acid moieties control the self-assembly of studied conjugates, the morphology of filament solutions was characterized after increasing pH to 7. The elevated pH exceeded the $pK_a$ of glutamic acid and effectively exposed negative charges on the peptides. Filament solutions at pH 7 maintained their filamentous nanostructures, while the length of filaments was significantly reduced. Charge repulsion is the primary force preventing facial aggregation from achieving long fiber length. DAs with more glutamic acids showed greater reduction in length than V-3TC-E1, which contains one glutamic segment. Parallel packing in low pH is also stronger than in high pH, as evidenced by the fact that fewer twisted filaments were found in PBS.

Next circular dichroism (CD) spectra were recorded for the three filament systems in the two different conditions (pH 4 and pH 7). All CD spectra predominantly showed a negative peak at −220 nm that was expected for #-sheets. The spectra of deprotonated conjugates were red-shifted related to those in typical beta-sheet. Previous works have shown that the redshift of beta-sheet signals is related to a larger hydrogen bonding distance. Without being bound by theory, it was contemplated that more negative charged filaments have a looser beta-sheet facial packing, which increased the redshift of the beta-sheet signal. Moreover, Filaments in deprotonated conjugate solutions showed a decreased intensity of the beta-sheet signal, which suggested the charge repulsion on glutamic acids weakened the hydrogen bonding of conjugate monomers within supramolecular assemblies. These results were also supported by the reduction in filament length observed in TEM images. This decrease in intensity was dependent upon the number of negative charges. Beta-sheet signal of V-3TC-E1 with one glutamic acid decreased slightly upon pH increase, while V-3TC-E3 with three glutamic acids displayed the greatest decrease. Taken together, the intermolecular hydrogen bonding and electrostatic repulsion are important for stabilizing the supramolecular assemblies.

Figure 9:
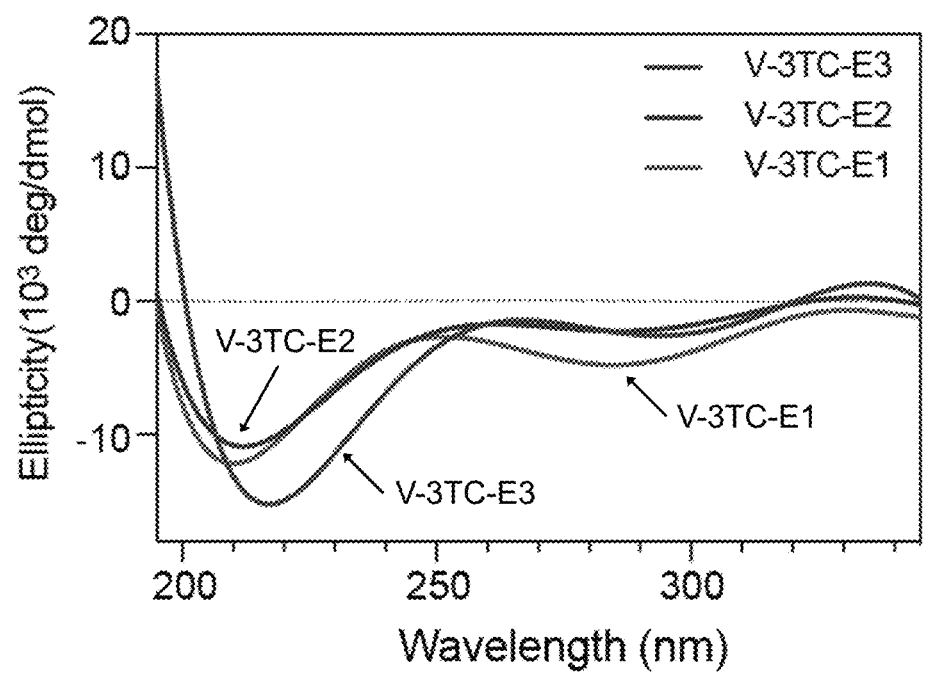
FIG. 9 shows normalized circular dichroism spectra collected between 200 nm and 360 nm of 3TC prodrug solutions of 200 µM after adding PBS.
Figure 10:
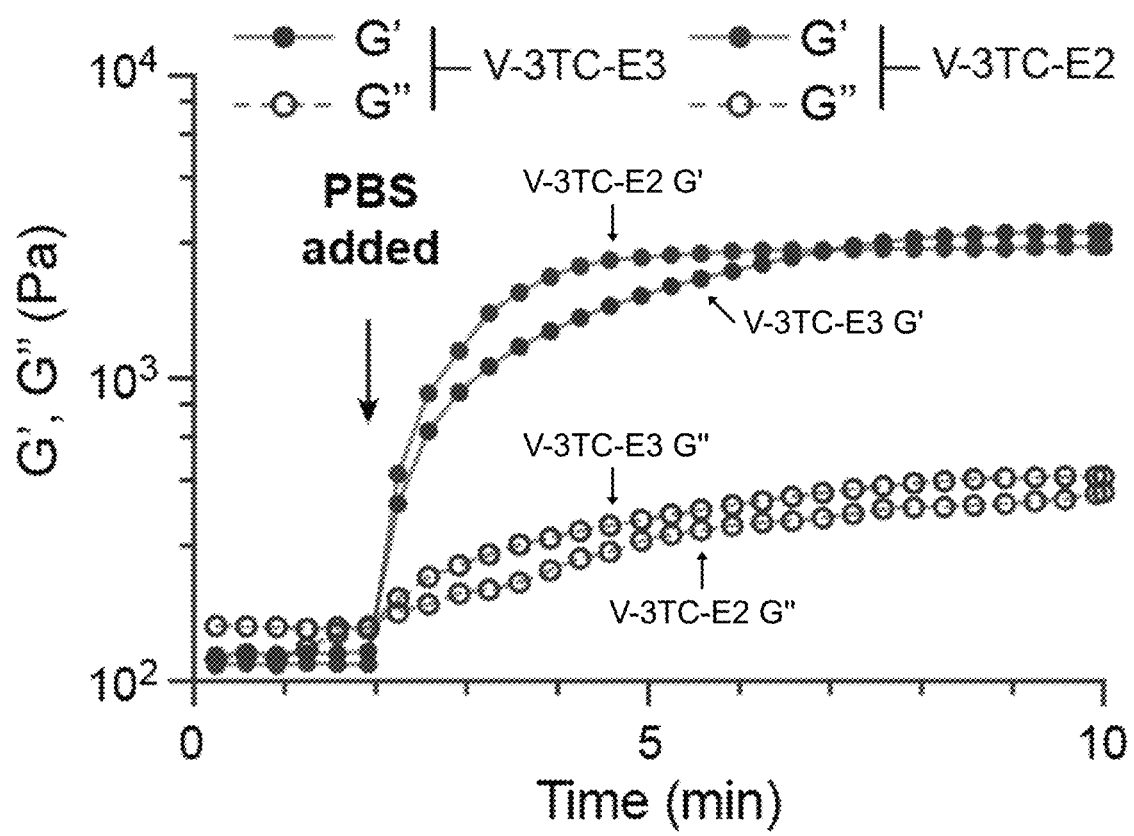
FIG. 10 shows plots of data from rheological experiments on the sol-gel transition process for V-3TC-E2 and V-3TC-E3.

After reviewing the data from TEM and CD studies that indicated supramolecular structures formed, experiments were conducted to evaluate hydrogel formation. Using a simple inversion test, data were collected to determine the critical gelation concentration of V-3TC-E3 and V-3TC-E2 to be between 1.5 mM and 2 mM in PBS. At concentrations of 2 mM and higher, V-3TC-E2 forms a hydrogel immediately upon the addition of PBS. V-3TC-E1 did not form hydrogel at 2 mM due to its low water solubility, potentially because its high affinity resulted in coagulation. Rheological measurements indicated that the DA solution undergoes sol-gel transition upon addition of PBS, at which the point storage modulus (G') increased dramatically to higher than loss modulus (G") (FIG. 10). The two filament solutions showed similar stiffness after gelation, whereas V-3TC-E2 transitioned faster. The data also indicated that the number of glutamic acids affected the mechanical properties of hydrogels formed (e.g., through controlling the morphology). Without being bound by theory, it is contemplated that the enhanced charge repulsion among glutamic acids decelerates assembly kinetics. Therefore, it was expected that increasing the number of glutamic acids in the peptide sequence would decrease gelation speed. In addition to direct observation of sol-gel transition, CD spectra were also used to collect data regarding how molecular packing affects hydrogel networks. CD spectra of the three conjugates after adding PBS showed negative bands at 254 nm corresponding to the chiral packing of Lamivudine (FIG. 9). V-3TC-E1 had a higher peak at 254 nm, indicating more lateral packing than the other two molecules. This indicates the lateral packing in V-3TC-E1 prevents network formation from individual filaments and results in precipitation.

Figure 11:
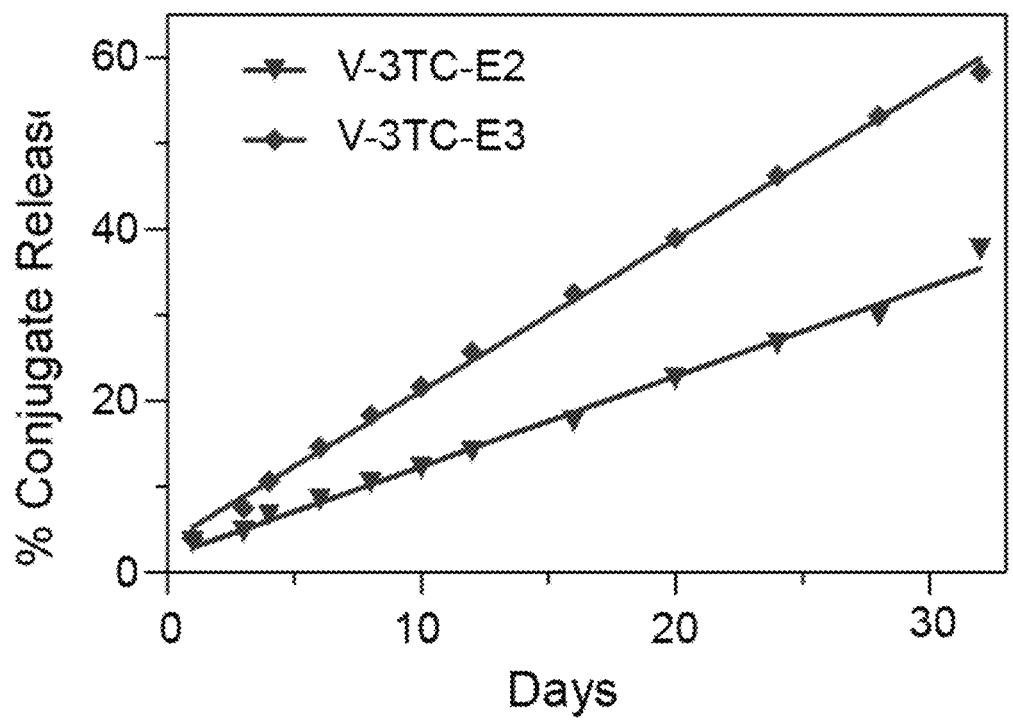
FIG. 11 shows plots of data showing the release profile of 3TC prodrugs from ARV hydrogels. Data were recorded every two days over a period of 1 month. Hydrogels were incubated at 37° C. Data are given as mean±SD (n=3).
Figure 12:
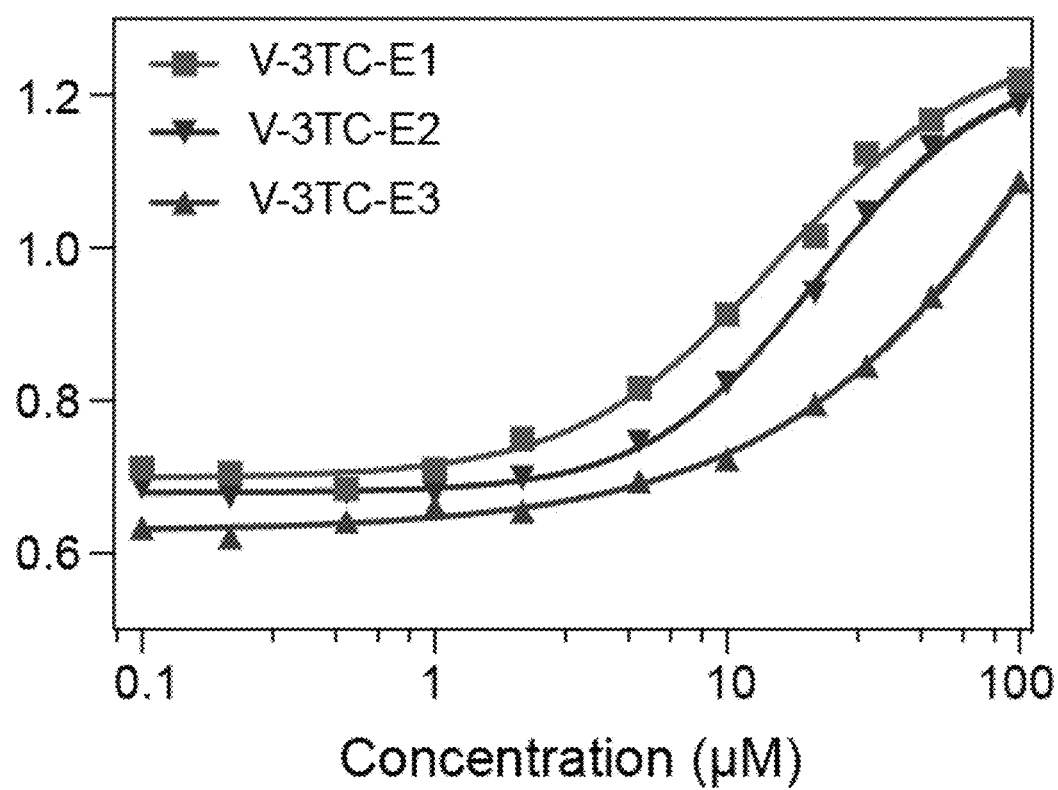
FIG. 12 shows plots of data from Nile Red assays to measure the CMCs of the three studied 3TC prodrugs.

To demonstrate the release profile of the drug conjugates, experiments were conducted to assess the release profiles of the supramolecular hydrogels in vitro. The collected medium solutions were analyzed using HPLC to determine the amount of drug conjugates released from hydrogel. Both E2 and E3 displayed a sustained linear release from the hydrogel. See FIG. 11. The release rates of both molecules stayed stable until the termination of the experiments. No significant burst release was observed in either hydrogel. Notably, E2 exhibited a relative shower in vitro release rate than V-3TC-E3. The daily release rates were 1.0% and 1.9% for E2 and E3, which released 29% and 52% of each conjugate over 28 days, respectively. At higher concentration, the hydrogels exhibited slower percentage release rates, though more drugs were released in absolute amount. Previous studies of supramolecular hydrogels showed a correlation between the hydrogel release rate of conjugates and the CMC value. The difference in CMC reflects the supramolecular stability of the conjugates, which largely determines the mechanical properties of resulting hydrogel. To verify this, the critical assembly concentrations of the three 3TC conjugates were measured using Nile Red as a fluorescent probe. The estimated CMC values are 5.3, 6.3, and 22.3 μM, respectively. See FIG. 12. V-3TC-E3 with higher CMC value also showed a faster release rate in vitro, which is consistent with our previous results.

Figure 13:
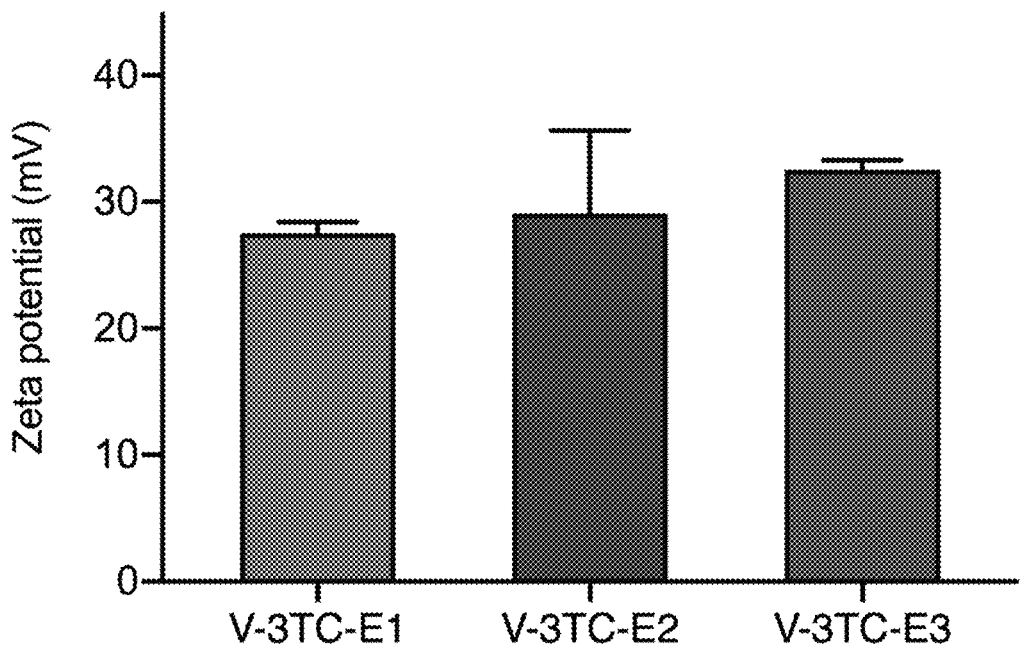
FIG. 13 shows bar plots of data from experiments measuring the zeta potential for V-3TC-E1, V-3TC-E2 and 3TC-V-E3.
Figure 14:
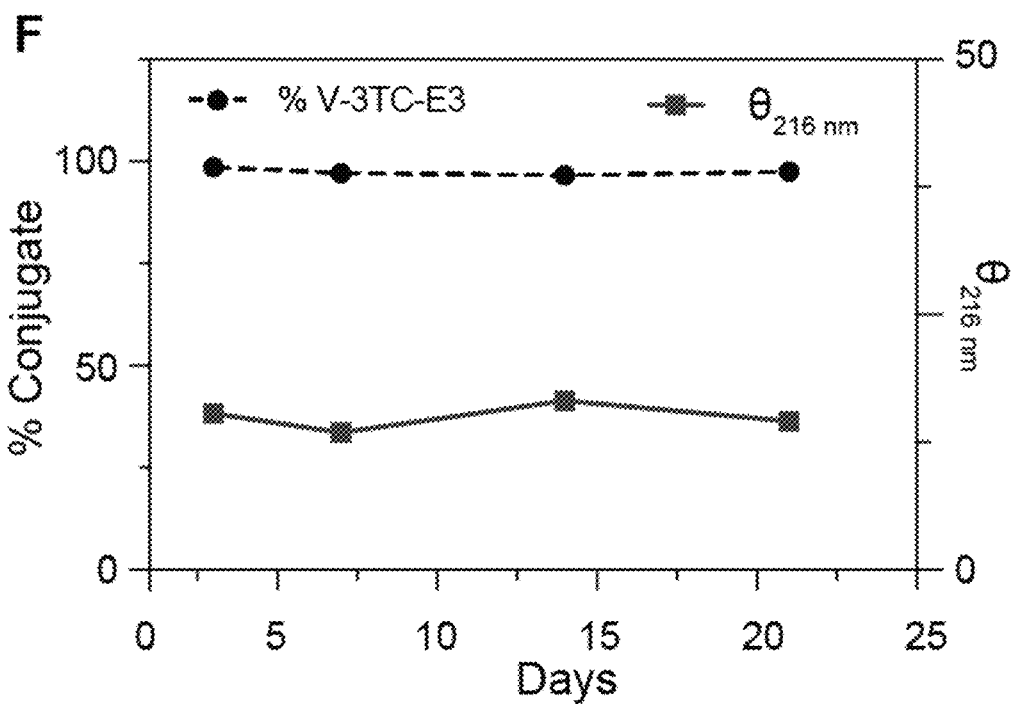
FIG. 14 shows data from stability tests using HPLC (dotted line) and CD (solid line). The data indicated that no noticeable in vitro chemical degradation was observed for the 3TC conjugates over 30 days.

Next, experiments were conducted to examine the stability of the conjugate within the hydrogel. A highly negative zeta potential of −30 mV suggested the electrostatic repulsion between filaments created by glutamic acid residues (FIG. 13). This repulsive interaction helps to stabilize the established supramolecular network and prevents fast degradation of the hydrogel. The stability of hydrogel was measured by its chemical composition using HPLC and molecular packing using CD. The conjugate peak areas and CD signals remained narrow over 30 days, which indicates minimal degradation (FIG. 14). Both the formulations remained stable for over one month, which signifies that the supramolecular hydrogels maintain their integrity under a range of dosing periods, reflective of the need in various therapeutical applications. Taken together, these results show that supramolecular hydrogel can effectively release 3TC for up to several weeks in vitro.

Prior to initiating pharmacokinetic studies, in vivo hydrogel retention profiles for the 3TC conjugate were studied.

Figure 15:
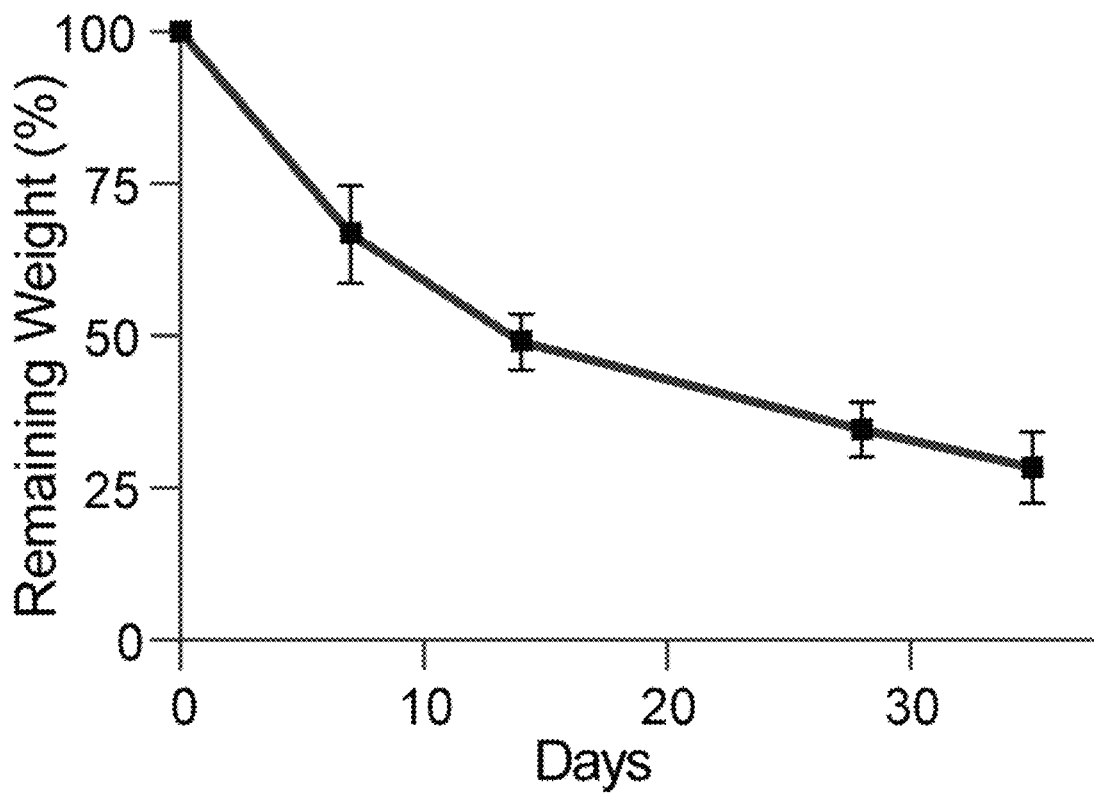
FIG. 15 is a plot of data from in vivo studies of hydrogel formation, local retention, and therapeutic release. Data were collected after in vivo gel formation by subcutaneous injection of a V-3TC-E3 aqueous solution in the backs of mice. The long-acting release of the ARV agent is indicated by the gradual reduction of hydrogels in the injection site as determined by the remaining weight.

V-3TC-E3 was chosen for in vivo gel retention study because it showed higher daily release rates. Although a slower release rate may indicate a more extended retention in the injected hydrogel, the higher daily drug release rate helps to maintain the plasma drug level above the effective concentration of lamivudine, which is especially important for fast clearing drugs. Adult Balb/cJ mice were injected subcutaneously with a solution containing 15 mM 3TC conjugate or PBS as a control. It was observed that a hydrogel depot formed within 5 min after injection, while the PBS control dissipated in less than 1 h. The in-situ formed hydrogel gradually degraded over 6 weeks as observed by visual observation of in vivo depots. To quantitatively determine the extent of degradation over time, the amount of the remaining hydrogel was evaluated using HPLC. The hydrogel exhibited a linear release profile, with approximately 25% gel remaining after 35 days. See FIG. 15. The degradation is faster at the beginning of the study. No notable differences were noted in all animals between mice after 3TC hydrogel treatment and the untreated control. Liver and kidney metabolic profiles were unchanged, which indicates that V-3TC-E3 did not adversely affect the functions of systemic organs. Total white cell, neutrophil, lymphocyte, and monocyte counts were also unchanged during the study period. Whole blood cell count. Overall, these results confirm the in vitro findings that the in-situ formed 3TC hydrogel could function as a delivery system for the sustained release of 3TC in vivo.

Figure 16:
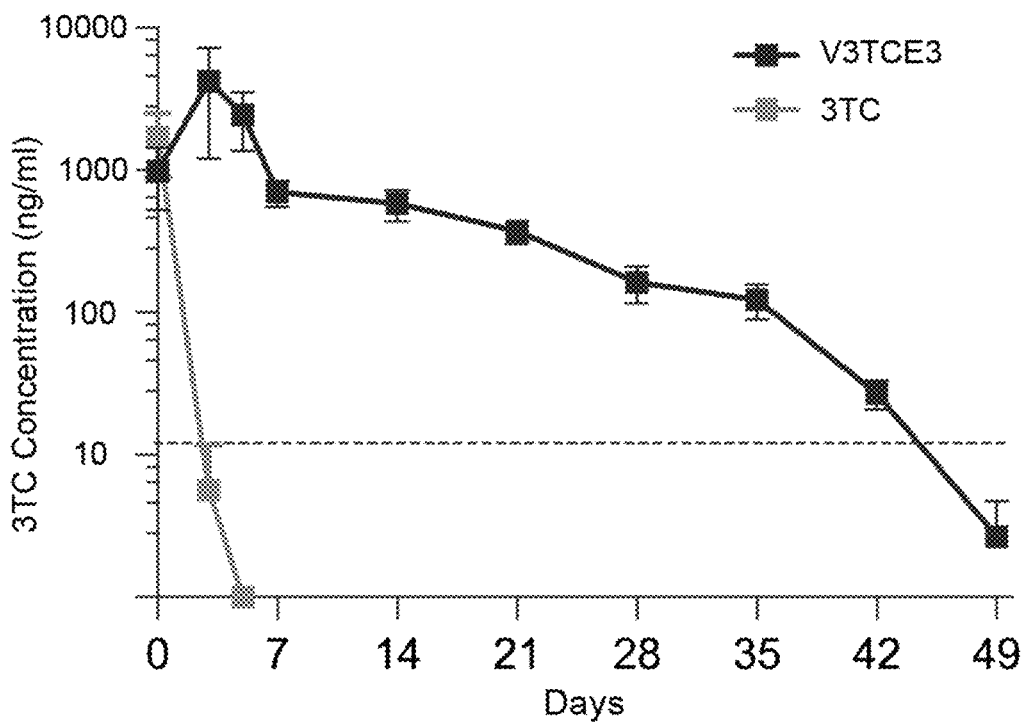
FIG. 16 is a plot of pharmacokinetic data. Experiments in Balb/cJ mice indicated that a high concentration of 3TC ARV was sustained in blood. Mice were administered 100 mg/kg equivalents of 3TC using 3TC or V-3TC-E3. Plasma was collected for drug analysis at days 1, 3, 5, 7, 14, 21, 28, 35, 42, and 49 after treatment. Plasma drug levels were measured from day 0 to day 49. 3TC levels were determined by UPLC-MS. Data are expressed as mean and SEM (n=5).

To evaluate the pharmacokinetic (PK) and biodistribution profile, male Balb/cJ mice were injected subcutaneously with a single dose of 75 mg/kg body weight 3TC equivalent of V-3TC-E3. Pharmaceutical standard 3TC was administrated at the same dosage and thus was used as a control. See FIG. 16. Whole blood and tissue samples were analyzed by ultra-performance liquid chromatography-tandem mass spectroscopy (UPLC-MS/MS) to determine drug (3TC) and conjugate prodrug (V-3TC-E3) levels. For free drug treatment, a fast decline in plasma 3TC concentration was detected compared with those of 3TC conjugates. FIG. 16. For conjugate treatment, the conjugate accumulated in the beginning days and reached its maxim concentration at days 3 to 7. The conjugates displayed a greatly slowed decay over the free drug control. For the 3TC conjugate (V-3TC-E3) treatment group, the 3TC concentrations were 5-fold above the EC-50 of 3TC for up to day 25. At day 40, the concentration was still above the EC50 value, whereas free 3TC was completely cleared after 3 days. See FIG. 16.

Figure 17:
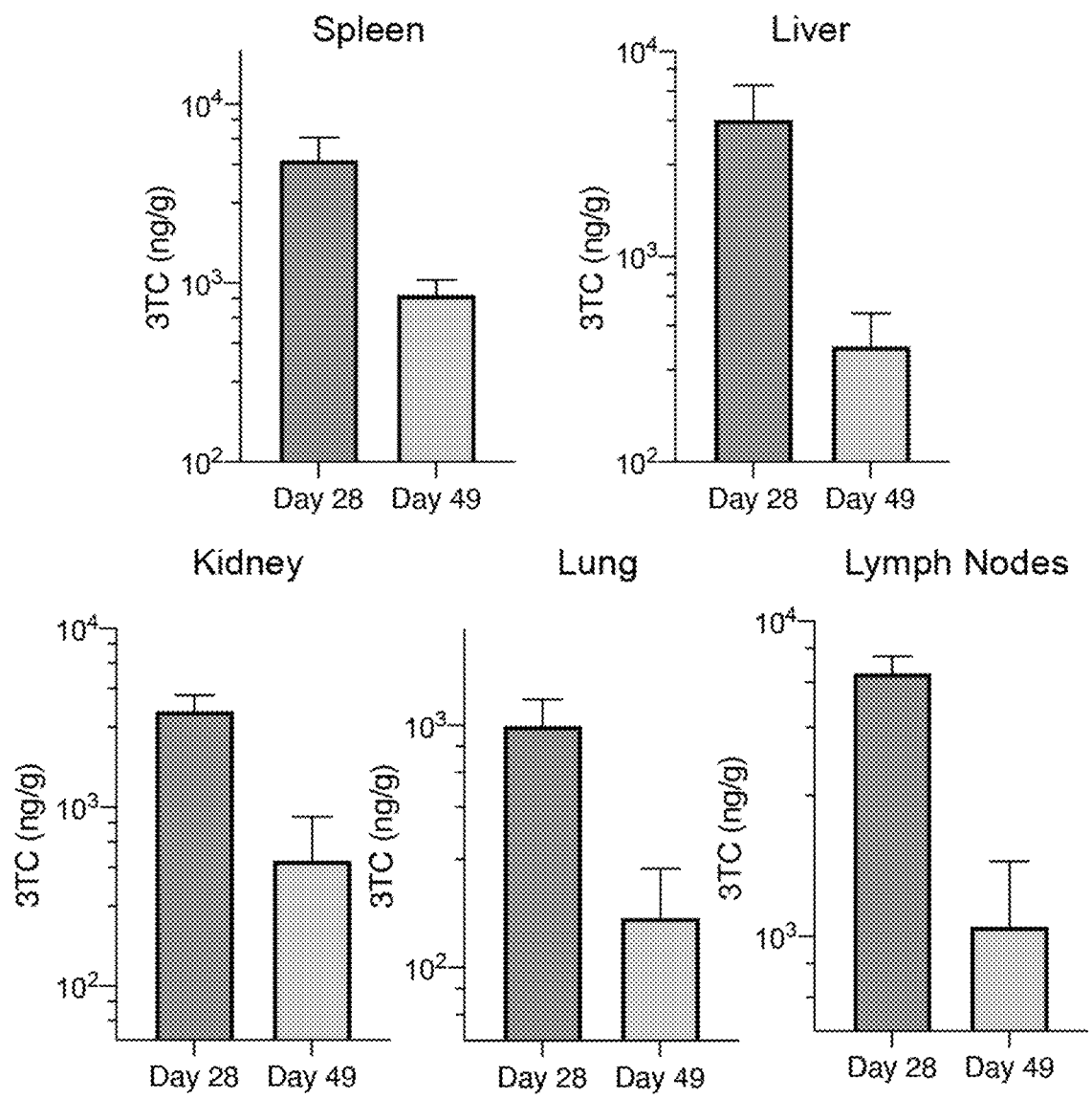
FIG. 17 shows drug levels in spleen, liver, kidney, lung, and lymph nodes on day 28 and day 49 after the treatment as described above for FIG. 16. 3TC levels were determined by UPLC-MS.
Figure 18A:
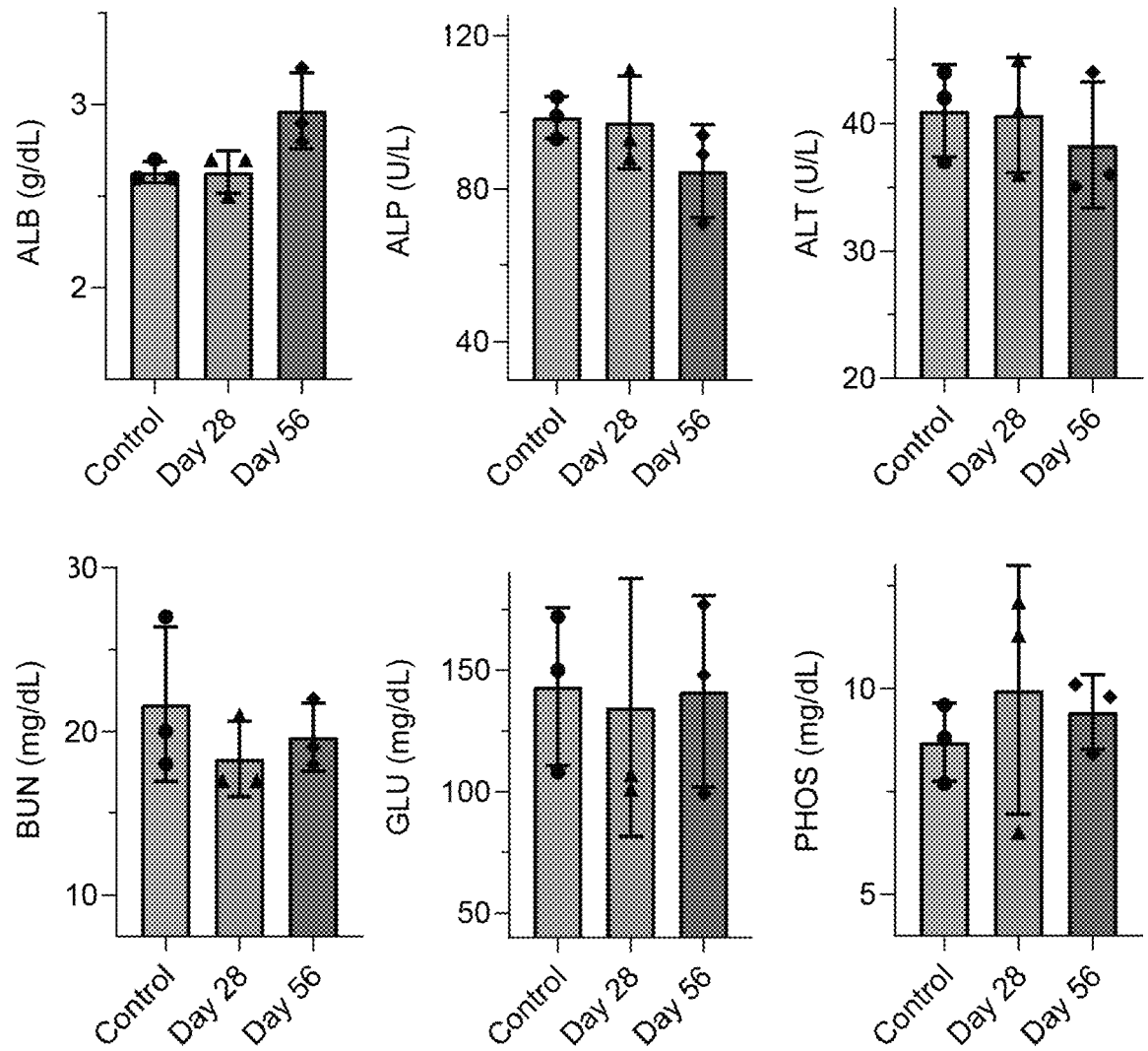
FIG. 18A is a series of bar plots showing the blood chemistry profile of Balb/cJ mice treated with V-3TC-E3 (as described above for FIG. 16) after sacrifice on day 28 and day 56. Albumin (ALB); Alkaline phosphatase (ALP); Alanine transaminase (ALT); blood urea nitrogen (BUN); Glucose (GLU); phosphate (PHOS). Data are presented as mean±sd; N=3 animals.
Figure 18B:
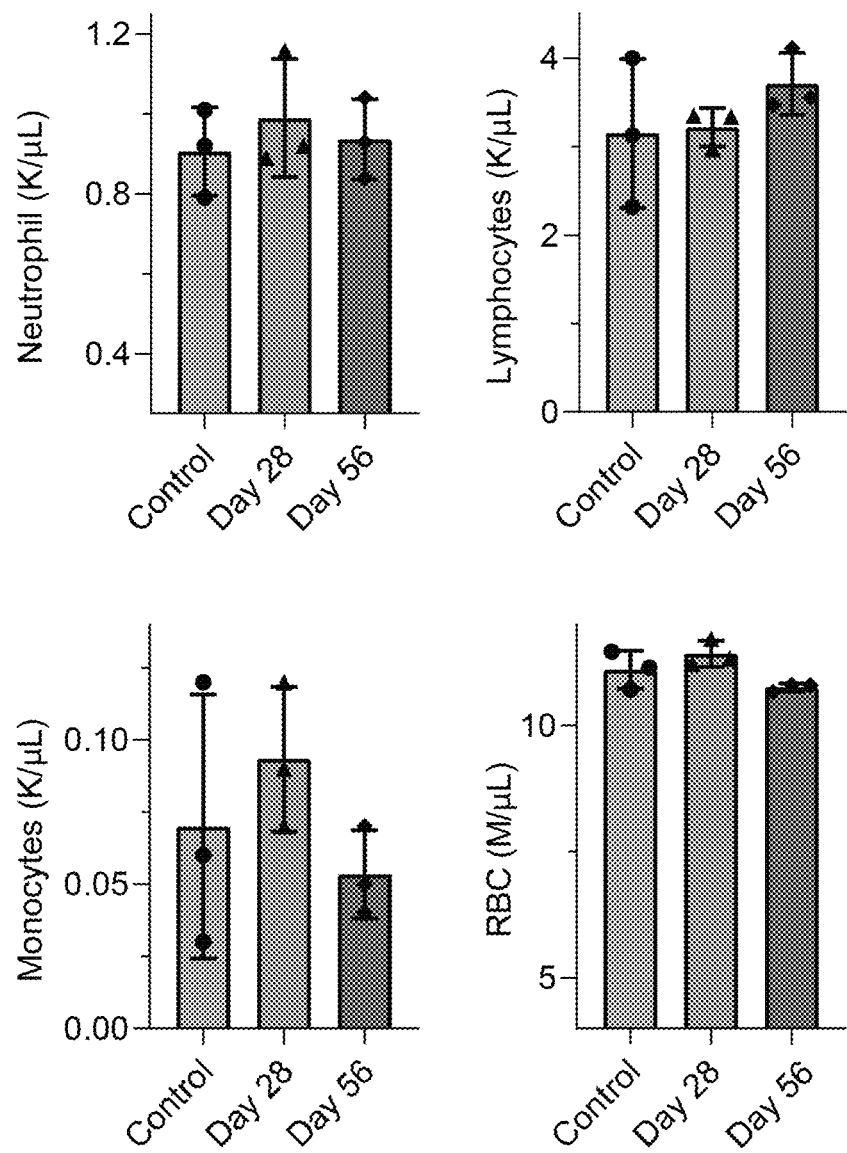
FIG. 18B is a series of bar plots showing the hematology profile of Balb/cJ mice treated with V-3TC-E3 (as described above for FIG. 16) after sacrifice on day 28 and day 56. Neutrophil; Lymphocytes; Monocytes; Red blood cells (RBC). Data are presented as mean±sd; N=3 animals.

PK parameters were determined using non-compartmental analysis for all treatment groups. The apparent 3TC half-life ($t_{1/2}$) after V-3TC-E3 treatment was 27 days, 15-fold longer than those of 3TC. Similarly, the 3TC mean residence time (MRT) of 3TC conjugate (38 days) was 10-fold longer than that of 3TC (2.1 days). 3TC conjugate also elicited significantly higher tissue levels than the free drug (FIG. 17). Of importance, V-3TC-E3 also elicited high 3TC tissue levels after treatment. As expected, 3TC free drug administration provided drug levels below detection after three days. Compared to 3TC free drug, the tissue 3TC levels for V-3TC-E3 at day 28 were 2337, 3453 and 4560 ng/g in liver, spleen, lymph node, lung, and kidney (FIG. 17). At day 49, high tissue 3TC levels were still detected. Collectively, the pharmacokinetics results confirmed a long-acting release profile for up to 8 weeks. Serum chemistry profiles and hematology results are shown in FIG. 18A and FIG. 18B.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A composition comprising a peptide-based antiretroviral therapeutic (ARV) prodrug selected from the group consisting of:

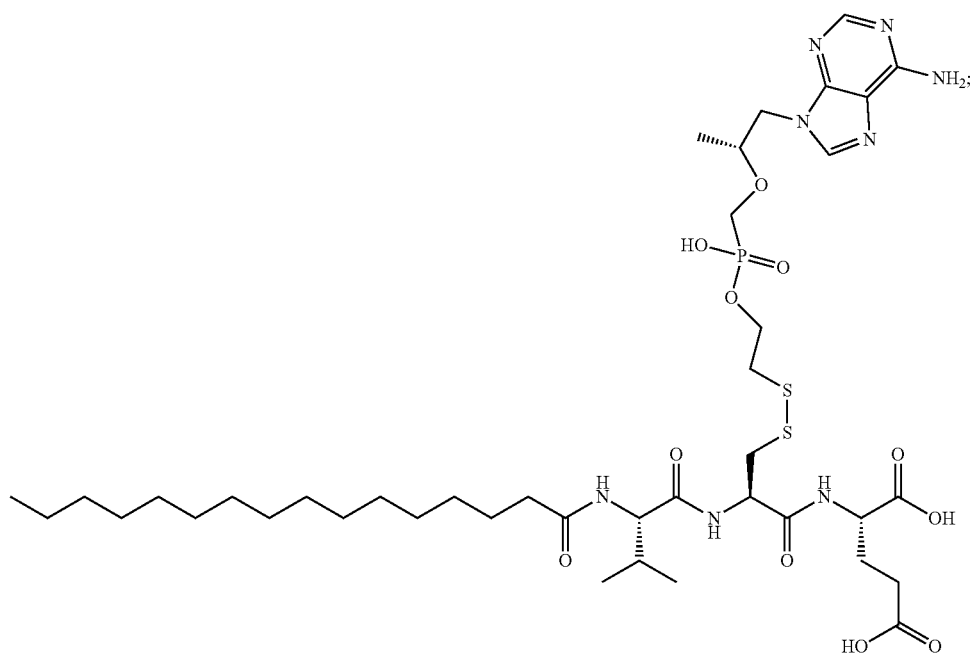

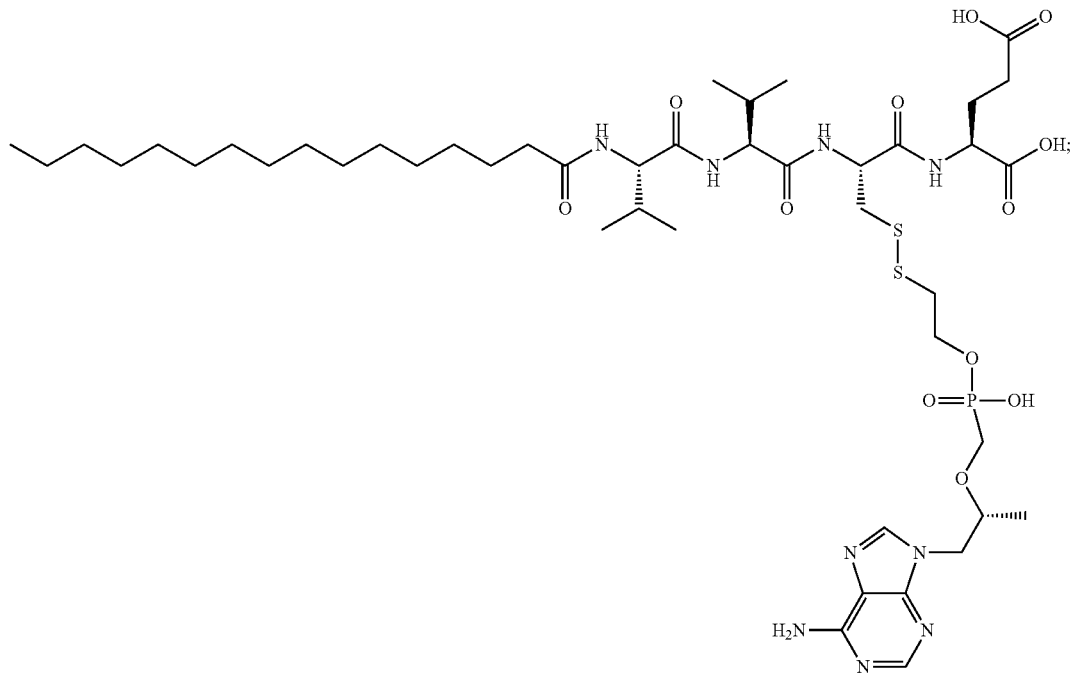
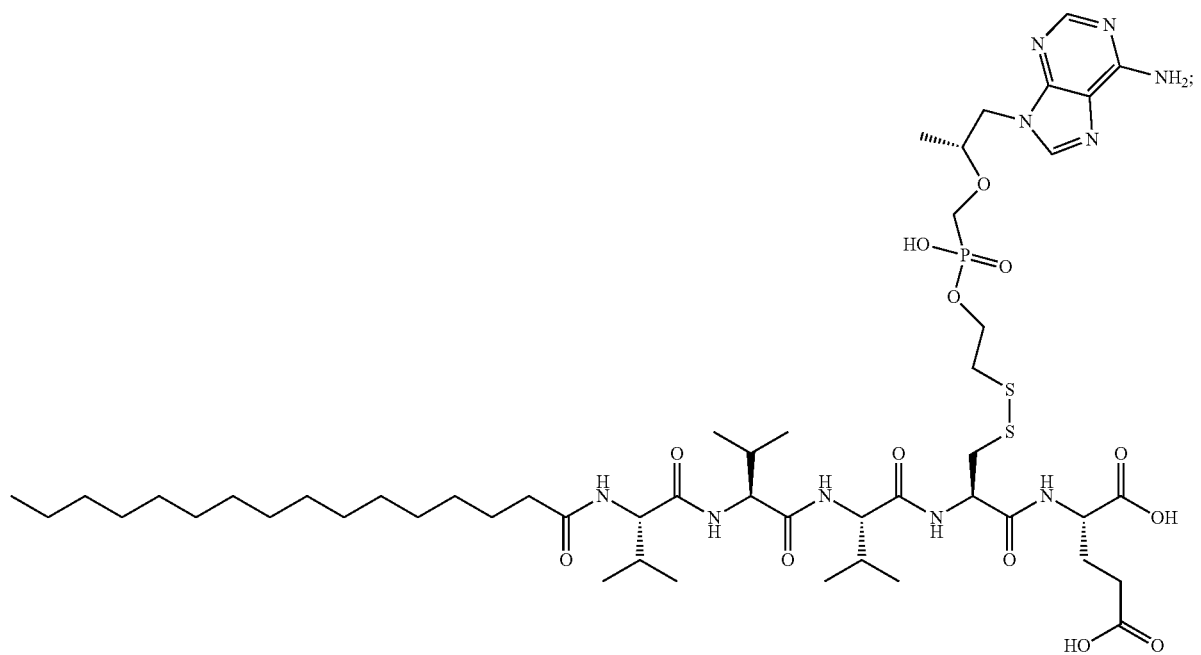

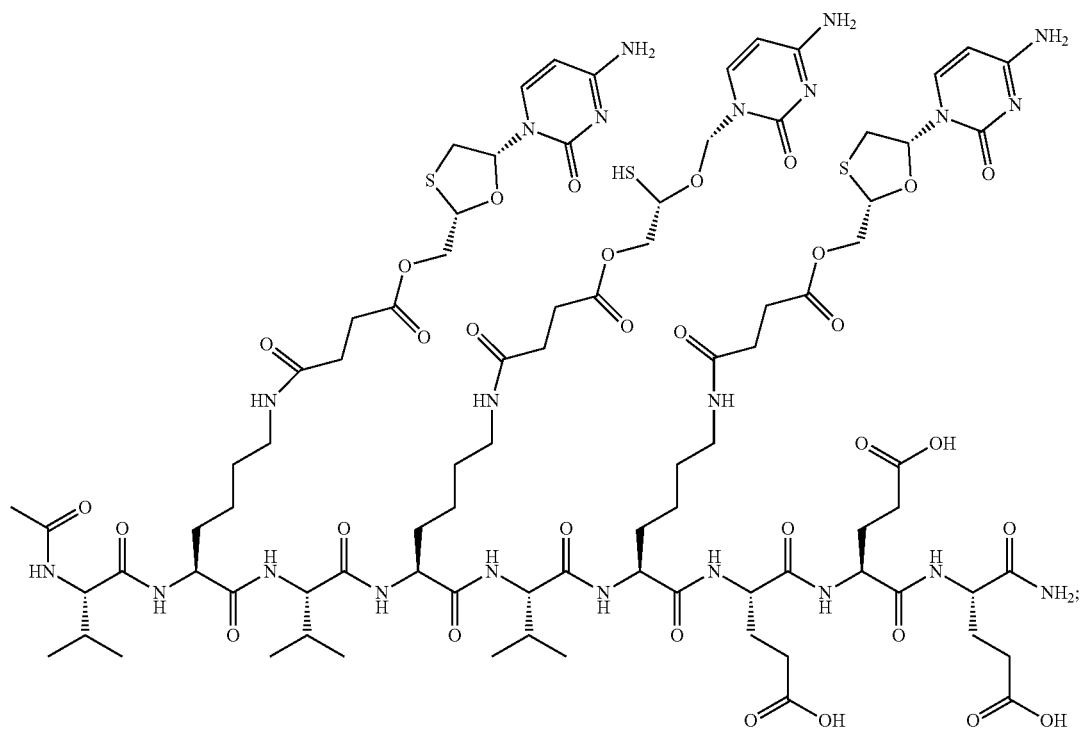
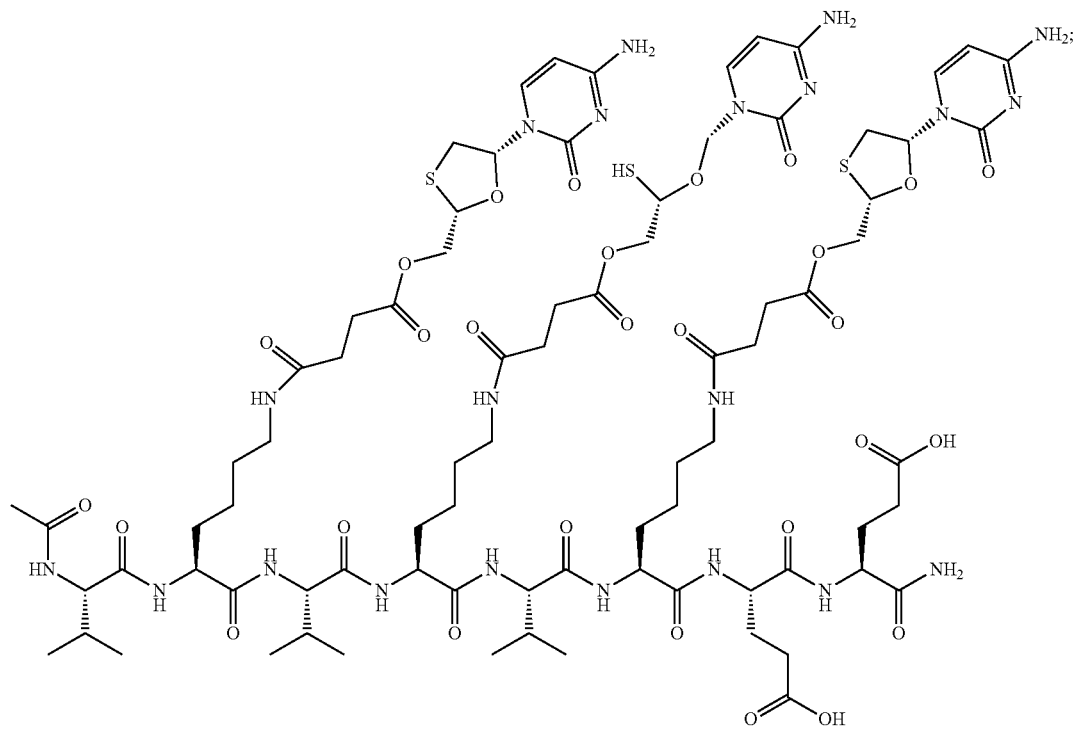

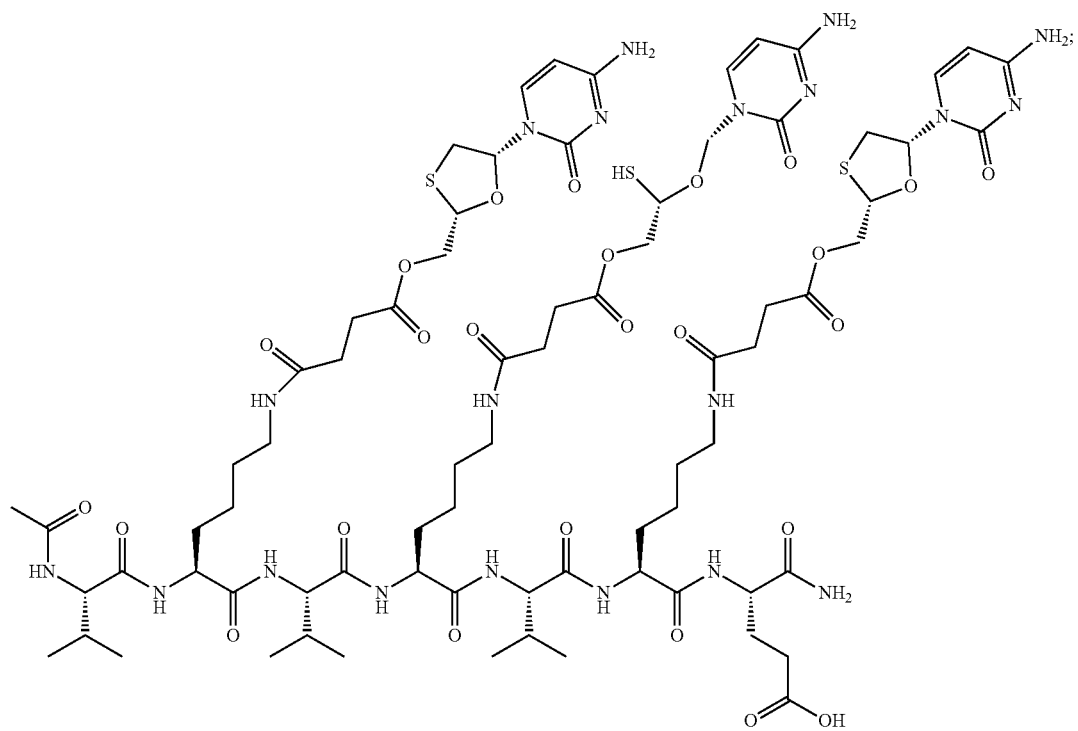
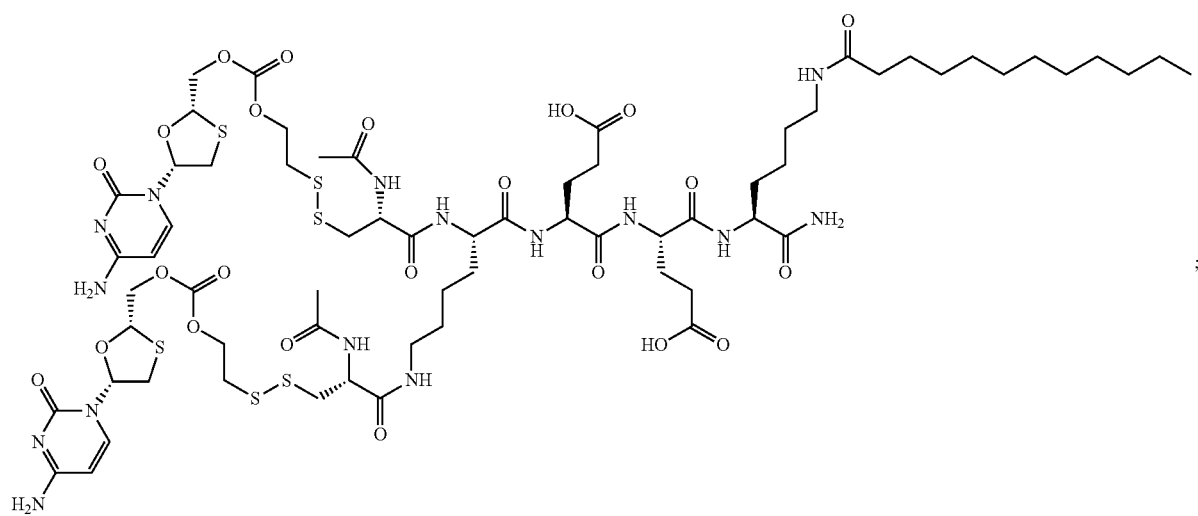

-continued

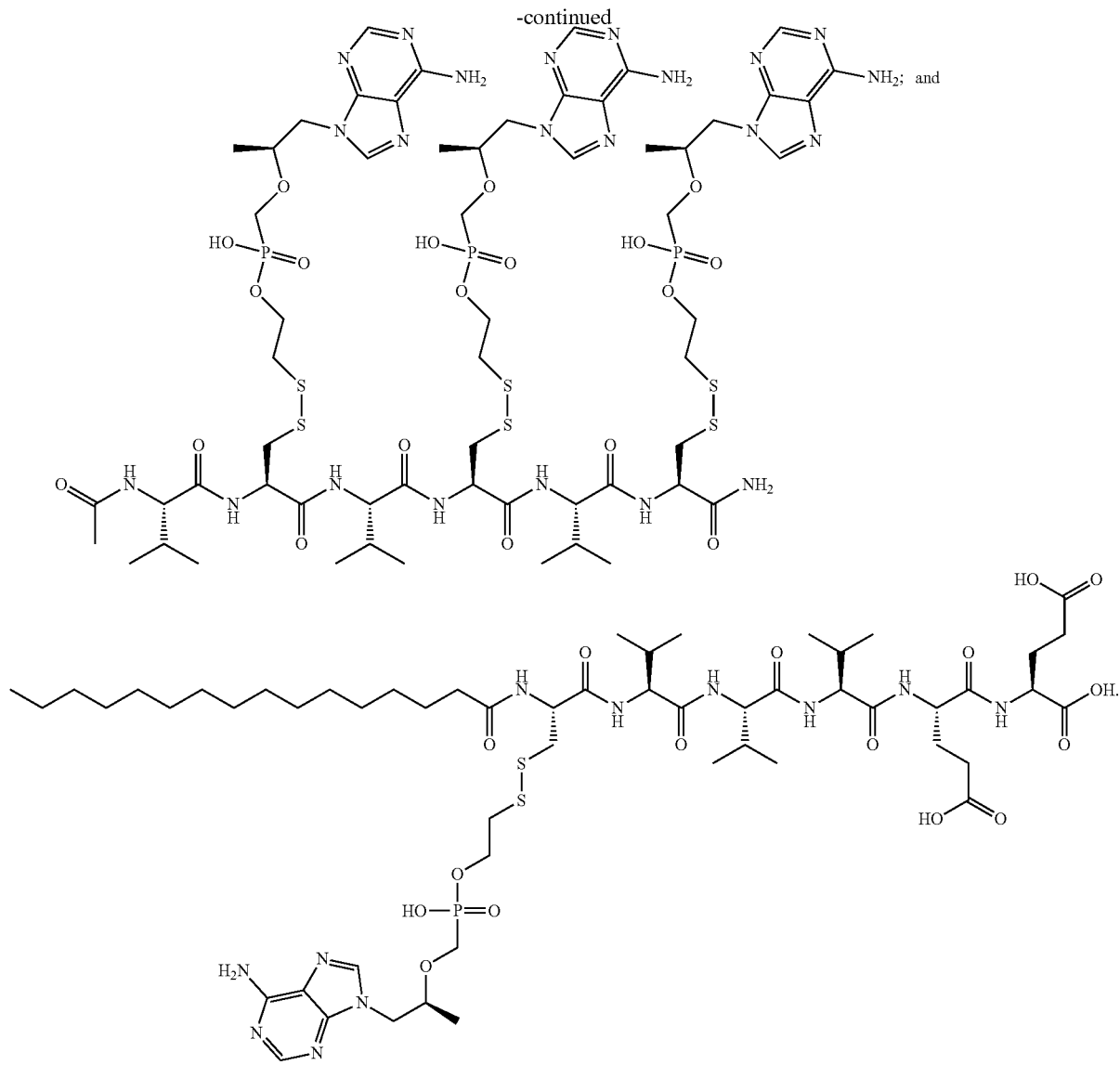

2. The composition of claim 1, wherein the composition further comprises a hydrophobic moiety encapsulated within a hydrophobic core of the composition.

3. A method for treating a viral infection in a subject in need thereof, wherein the method comprises administering to said subject a therapeutically effective amount of a composition of claim 1, and wherein said viral infection is selected from a retroviral infection or a hepatitis B viral infection.

4. The method of claim 3, wherein said viral infection is a chronic viral infection.

5. The method of claim 3, wherein said viral infection is a hepatitis B viral infection.

6. The method of claim 3, wherein said viral infection is a human immunodeficiency virus (HIV) infection.

7. The method of claim 3, wherein the composition is administered by subcutaneous or intramuscular injection.

8. The method of claim 3, wherein the subject has a hepatitis B viral infection or acquired immune deficiency syndrome (AIDS).

* * * * *